(12) United States Patent
Mollenhauer et al.

(10) Patent No.: US 8,017,124 B2
(45) Date of Patent: Sep. 13, 2011

(54) USE OF DMBT1 FOR CAPTURING SULPHATE AND PHOSPHATE GROUP EXPOSING AGENTS

(75) Inventors: Jan Mollenhauer, Heidelberg (DE); Caroline End, Mannheim (DE); Stephanie Blaich, Heidelberg (DE); Gaby Bergmann, Heidelberg (DE); Marcus Renner, Leimen (DE); Stefan Lyer, Heidelberg (DE); Rainer Wittig, Heidelberg (DE); Annemarie Poustka, Heidelberg (DE); Floris Bikker, Utrecht (NL); Antoon Ligtenberg, Amstelveen (NL); Arie Nieuw-Amerongen, Breukelen (NL); Enno Veerman, Volendam (NL)

(73) Assignee: Deutsches Krebsforschungszentrum, Heidelberg (DE)

( * ) Notice: Subject to any disclaimer, the term of this patent is extended or adjusted under 35 U.S.C. 154(b) by 530 days.

(21) Appl. No.: 10/590,657

(22) PCT Filed: Feb. 25, 2005

(86) PCT No.: PCT/EP2005/001994
§ 371 (c)(1),
(2), (4) Date: Aug. 25, 2006

(87) PCT Pub. No.: WO2005/079834
PCT Pub. Date: Sep. 1, 2005

(65) Prior Publication Data
US 2008/0234185 A1     Sep. 25, 2008

(30) Foreign Application Priority Data
Feb. 25, 2004   (EP) .................................. 04004281

(51) Int. Cl.
*A61K 39/00* (2006.01)
*C12Q 1/00* (2006.01)
*C07H 21/04* (2006.01)

(52) U.S. Cl. .... 424/185.1; 424/7.1; 424/7.2; 424/184.1; 424/234.1; 424/277.1; 424/570; 435/4; 530/300; 530/350; 536/23.1; 536/23.5; 536/24.3

(58) Field of Classification Search .................. 424/7.1, 424/7.2, 184.1, 185.1, 234.1, 277.1, 570; 435/4; 530/300, 350; 536/23.1, 23.5, 24.3
See application file for complete search history.

(56) References Cited

U.S. PATENT DOCUMENTS
6,287,605 B1    9/2001  Malamud et al.
6,346,606 B1    2/2002  Mollenhauer et al.

OTHER PUBLICATIONS

Takeshita H. et al., Jpn J. Cancer Res., Sep. 1999, vol. 90, pp. 903-908.
Prakobphol et al., J.Biol Chem., Dec. 2000, vol. 275. No. 51, pp. 39860-39866.
Wu et al., AIDS Res. Hum. Retrovir, 2003, vol. 19, pp. 201-209.
Hartshorn et al., Am. J. Physiol. Lung Cell. Mol. Physiol., Jul. 2003, vol. 285, pp. 1066-1076.
Bikker et al., J. Biol. Chem., 2002, vol. 277, pp. 32109-32115.
Seifter et al., Methods in Enzymology, 1990, vol. 182, 626-646.
Rattan et al. Annals N.Y. Academy of Science, 1992, vol. 663, pp. 48-62.
Lee et al., Nucleric Acids Research, 1979, vol. 6, No. 9, pp. 3073-3091.
Cooney et al., Science, 1988, vol. 241, pp. 456-459.
Beal et al., Science, 1991, vol. 251, pp. 1360-1363.
Okano et al., Journal of Neurochemistry, 1991, vol. 56, No. 2, pp. 560-567.
Saiki et al., Nature, Nov. 1986, vol. 324, pp. 163-166.
Myers et al., Science, Oct. 1985, vol. 230, pp. 1242-1246.
Kang W. et al., Federation of European Biochemical Societies, 2003, vol. 540, pp. 21-25.
Mollenhauer J. et al., Cancer Research, Dec. 2001, vol. 61, pp. 8880-8886.
Madsen et al., Eur. J. Immunnol., 2003, vol. 33, pp. 2327-2336.

*Primary Examiner* — Rodney P. Swartz
(74) *Attorney, Agent, or Firm* — Birch, Stewart, Kolasch and Birch, LLP

(57) ABSTRACT

Disclosed is the use of DMBT1, or of the nucleic acid encoding it, for the manufacture of a medicament for the treatment of a patient suffering from a disease caused by an agent, which possesses at least one accessible sulphate and/or at least one accessible phosphate group, uses of DMBT1 as a diagnostic for diagnosing the susceptibility of an individual to sulphate or phosphate groups, as well as methods for diagnosis, prophylaxis or treatment of diseases caused by an agent which possesses at least one accessible sulphate and/or at least one accessible phosphate group.

24 Claims, 31 Drawing Sheets

FIGURE 1 a

*DMBT1*$^{wt}$

GSESSLALRLVNGGDRCQGRVEVLYRGSWGTVCDDSWDINDANVVCRQLGCGWAMSAPGNAHFGQSSGPIVLDDVRCSGHESYLWSCPHNGWLSHNCGHHEDAGVICSA

SRCR consensus

SRCRP1 (a)
SRCRP2 + 6N (b)
SRCRP2 + 5N (c)
SRCRP2 + 4N (d)*
SRCRP2 + 3N (e)*
SRCRP2 + 2N (f)*
SRCRP2 + 1N (g)*
SRCRP2 (h)*
SRCRP2 + C1 (j)*
SRCRP2 + C2 (j)
SRCRP2 + C3 (k)
SRCRP2 + C5 (l)
SRCRP3 (m)
SRCRP4 (n)
SRCRP5 (o)
SRCRP6 (p)
SRCRP7 (q)

d

USE OF DMBT1 FOR CAPTURING SULPHATE AND PHOSPHATE GROUP EXPOSING AGENTS

The present invention relates to the capturing of agents which possess accessible sulphate or phosphate groups as well as to the treatment of diseases caused by such agents.

Infections, tissue damage, and inflammations are key triggers for cancer development. For example, in the gastrointestinal tract, *Helicobacter pylori* infection, impaired wound healing, and ulcerative colitis are known to be associated with the development of cancer. There are numerous, thus far identified or unidentified agents which are responsible to cause these diseases. Among these agents are microorganisms like bacteria, viruses, protozoa or fungi as well as smaller non-living chemical compounds and compositions. To date, there is no first-line treatment available which enables treating diseases irrespective of the precise nature of the pattern. Thus, it would be desirable to have a substance readily available, which would recognize the molecular structure or component commonly shared by various disease-causing agents, i.e. in a way of pattern recognition, and as such could be used as a pan-acting pharmaceutical for a variety of diseases. Pattern recognition receptors (PRRs) are considered to play a role in pathogen-defense, inflammation, cancer, aspects of tissue homeostasis, and certain developmental processes, but their dual-specificity for non-self and self structures poses unsolved problems.

Consequently, the problem underlying the present invention resides in providing such a pan-acting pharmaceutical.

According to the present invention, the problem is solved by
the use of a polypeptide comprising the sequence of SEQ ID NO:1, or a functional fragment or derivative thereof, or of a nucleic acid comprising the sequence of SEQ ID NO:2, or a functional fragment or derivative thereof, for the manufacture of a medicament for the prophylaxis and/or treatment of a disease caused by an agent,
wherein the agent possesses at least one accessible sulphate and/or at least one accessible phosphate group.

The inventors have surprisingly found that the human protein Deleted in Malignant Brain Tumors 1 (DMBT1, the full-length protein thereof is shown in SEQ ID NO:1) is a dual-specific PRR for non-self (bacterial cell wall components, gp120 of HIV, damage-, inflammation-, and cancer-causing sulfated carbohydrates) and self structures (DNA, phospholipids, cell surface and extracellular matrix carbohydrates), which interacts with accessible sulfate and/or phosphate groups, which are present on numerous compounds, compositions and organisms.

As known in the art, DMBT1 is a scavenger receptor cysteine-rich (SRCR) secreted protein mainly expressed by epithelia and glands. DMBT1 is also known as salivary agglutinin or glycoprotein-340 (gp340). Furthermore, DMBT1 is known to selectively interact with some bacterial pathogens (e.g. Prakobphol et al., 2000, J. Biol. Chem., Vol. 275, pages 39860-39866) and the viruses HIV (Wu et al., 2003, AIDS Res. Hum. Retrovir., Vol. 19, pages 201-209) and influenza A viruses (Hartshorn et al., 2003, Am. J. Physiol. Lung Cell. Mol. Physiol., 2003, Vol. 285, pages 1066-1076), and thus inhibits the infectivity of these virus. The bacteria binding region of DMBT1 has been previously mapped to a 16-amino acid motif located within a SRCR-domain of which 14 are present in DMBT1 (Bikker et al., 2002, J. Biol. Chem., Vol. 277, pages 32109-32115). Thus far, the mechanism of pathogen binding has remained unclear. Wu et al. and Hartshorn et al. (supra) proposed that the recognition of HIV glycoprotein-120 and influenza A viruses relies on DMBT1 carbohydrates.

None of the documents of the prior art gives a hint on a probably general mechanism or pattern recognition according to which DMBT1 does interact with the above described pathogens or other compounds.

The inventors have now found that pattern recognition of DMBT1 is mediated via an 11 amino acid motif that binds sulfate and phosphate groups. In addition, germline deletions in humans quantitatively impair its scavenging activity, as exemplified for *Streptococci, Salmonella, Helicobacter pylori*. It is proposed by the present invention that pattern recognition provides a common mechanistic basis for DMBT1's putative broad functional spectrum, which includes tumor suppression, epithelial differentiation, tissue protection and regeneration, pathogen-defense, and gallstone formation. By acting as dual-specific PRR, DMBT1 may exert a general insulator function against a broad range of pathogens, which predicts a contribution of DMBT1 germline deletions to human susceptibility to infection, inflammation, and cancer. Furthermore, the inventors found that a 40% decrease in level of DMBT1 in male mice correlates with an increased susceptibility and with a deficient protection against dextran sulfate sodium (DSS)-induced tissue damage and inflammation in the colon. Human DMBT1 directly interacts with DSS and carrageenan, the latter being used as stabilizer in human food and suspected to cause inflammation and colorectal cancer. The interaction with DSS and carrageenan is mediated via the DMBT1 binding site for bacterial and viral pathogens described supra. The efficacy of the medicament provided by the present invention is mediated by the interaction of DMBT1 with an accessible sulphate or phosphate group displayed or exposed by the disease-causing agent.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids and that many amino acids, including the terminal amino acids, may be modified in a given polypeptide, either by natural processes, such as processing and other post-translational modifications, but also by chemical modification techniques which are well known to the art. Ellen the common modifications that occur naturally in polypeptides are too numerous to list exhaustively here, but they are well described in basic texts and in more detailed monographs, as well as in a voluminous research literature, and they are well known to those of skill in the art.

Generally, the term "polypeptide" refers to fall length human DMBT1 having the amino acid sequence as depicted in SEQ ID NO: 1, or a functional fragment or derivative thereof.

In the context of the present invention the term "functional fragment or derivative" refers to amino acid sequences which differ from the amino acid sequence of SEQ ID NO:1 in one or more positions and share a high degree of homology to that sequence. Homology means thereby a sequence identity over the overall length of at least 70%, preferably 80%, more preferably 90%. The deviations to SEQ ID NO:1 can originate from deletions, additions, substitutions or insertions. A fragment or derivative is considered "functional", when it is capable of binding to sulphate and/or phosphate groups. One possible test for functionality is provided in the example section (see Methods: "Turbidometric aggregation assays"). Furthermore, "fragment" refers to a peptide of 5, 6, 7, 8, 9, 10, 11, up to 20 amino acids or to a protein of at least 20, 25, 50, 100, or more amino acids. Typically, a fragment comprises at least 8, 10, 12, 14, 16 or more contiguous amino acids of the amino acid sequence of SEQ ID NO: 1. Particularly, the polypeptide refers to a sequence comprising the amino acids GRVEVLYRGSW (SEQ ID NO: 9) which is present several times within SEQ ID NO:1, and multiples thereof, and which represents the 11 amino acid motif that binds sulfate and phosphate groups.

Furthermore, the polypeptide refers to a sequence comprising the amino acids GRVEILYRGSW (SEQ ID NO: 10) and/or GRVEVLYQGSW (SEQ ID NO: 11).

Furthermore, the term "functional derivative" can also mean, that one or more amino acids of the amino acid sequence are chemically modified, depending on the intended use. The chemical modifications can, for example, effect that the polypeptide is stabilized or features other desired physical or biochemical properties. Modifications known to the skilled artisan include, but are not restricted to, acetylation, acylation, ADP-ribosylation, N- and O-glycosylation, amidation, covalent attachment of flavins, lipids, phosphoinositol, crosslinking, disulfide bridge formation, cyclisation, demethylation, hydroxylation, iodination, methylation, myristoylation, proteolytic processing, prenylation, sulfatation, tRNA-mediated attachment of amino acids. Such modifications are known to the person skilled in the art and are described in the literature, for instance Proteins—Structure and molecular properties, 2nd Ed, T. E. Creighton, W.H. Freeman and Company, New York (1993). Many detailed reviews are available on this subject, such as, for example, those provided by Wold, F., Posttranslational Protein Modifications: Perspectives and Prospects, pgs. 1-12 in Posttranslational covalent modification of proteins, B. C. Johnson, Ed., Academic Press, New York (1983); Seifter et al., Analysis for protein modifications and nonprotein cofactors, Meth. Enzymol. 182: 626-646 (1990) and Rattan et al., Protein Synthesis: Posttranslational Modifications and Aging, Ann. N.Y. Acad. Sci. 663: 48-62 (1992).

A "nucleic acid", as used herein, includes all nucleic acids as described below. Generally, a "nucleic acid" can be an "oligonucleotide" which refers to relatively short polynucleotides. Often the term refers to single-stranded deoxyribonucleotides, but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases tropically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily mU form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation. In addition, a nucleic acid which can be used according to the present invention includes polynucleotides referring to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

Generally, the term "nucleic acid" refers to full length DNA encoding human DMBT1 having the nucleic acid sequence as depicted in SEQ ID NO: 2, or a functional fragment or derivative thereof.

In the context of the present invention the term "functional fragment or derivative" of the nucleic acid refers to nucleic acid sequences which differ from the nucleic acid sequence of SEQ ID NO:2 in one or more positions and share a high degree of homology to that sequence. Homology means thereby a sequence identity over the overall length of at least 70%, preferably 80%, more preferably 90%. The deviations to SEQ ID NO:2 can originate from deletions, additions, substitutions, insertions or recombinations of nucleotides. Furthermore, "fragment" refers to contiguous stretch of at least 12 nucleotides. Furthermore, the fragment can be 30, 40, 50, 100, 250 or 500 or more nucleotides in length. The length of the fragment is adjusted according to its intended use. A fragment can, for instance, be used as a primer or probe, which hybridizes under stringent conditions to a stretch of at least 12, 20, 25, 40, 50 or more contiguous nucleotides.

For some purposes it can be advantageous, when the "fragment or derivative" includes a nucleic acid which is complementary to the nucleic acid comprising at least a part of SEQ ID NO:2, and, as such, hybridizes preferably under stringent conditions with a nucleic acid comprising at least part of SEQ ID NO:2. As an example, such a nucleic acid can be used as a probe to detect the DMBT1 gene, or as an antisense nucleic acid in order to inhibit DMBT1 expression, as discussed further below.

Two nucleic acid strands are considered to be 100% complementary to each other over a defined length if in a defined region all A's of a first strand can pair with a T (or an U) of a second strand, all G's of a first stand can pair with a C of a second strand, all T (or U's) of a first strand can pair with an A of a second strand, and all C's of a first strand can pair with a G of a second strand, and vice versa. The degree of complementarity can be, e.g. determined over a stretch of 20 nucleotides, i.e. a 60% complementarity means that within a region of 20 nucleotides of two nucleic acid strands 12 nucleotides of the first strand can base pair with 12 nucleotides of the second strand according to the above ruling, either as a stretch of 12 contiguous nucleotides or interspersed by non-pairing nucleotides, when the two strands are attached to each other over said region of 20 nucleotides. For the purpose of achieving selective hybridization between two complementary strands, the skilled artisan is aware of a variety of hybridization conditions and stringencies (e.g. described in Sambrook et al., A laboratory Manual). The incubation conditions, e.g. time, salt concentrations, temperature, can vary and usually depend on the sequence and length of the prepared nucleic acid and may therefore be adjusted each time. Such conditions are, for example, hybridization in 2×SSC, pH 7.0/0.1% SDS at about 65-69° C. for 18-23 hours, followed by a washing step Kith 2×SSC/0.1% SDS at 50° C. In order to select the stringency, the salt concentration in the washing step can for example be chosen between 2×SSC/0.1% SDS at room temperature for low stringency and 0.2× SSC/0.1% SDS at 50° C. for high stringency. In addition, the temperature of the washing step can be varied between room temperature, ca. 22° C., for low stringency, and 65° C. to 70° C. for high stringency.

For the use of the present invention, the sulphate and phosphate groups of the disease causing agent have to be accessible in order to be efficiently recognized by the polypeptide.

As used herein, the term "accessible" means that the phosphate and/or sulphate group is arranged in a manner which allows for the interaction with the polypeptide of the present invention. A phosphate or a sulphate group can be considered accessible when it is available free from other compounds which may interfere with said interaction. Furthermore, it can be part of a larger, macromolecular structure and still be accessible, provided that the surrounding molecules will not negatively affect said interaction.

In the context of the present invention, the term "agent" refers to any organism, compound or composition, which possesses at least one accessible sulphate and/or at least one accessible phosphate group.

A variety of diseases, in particular infectious or inflammatory diseases, are caused by microorganisms like bacteria, viruses, fungi, protozoa, and the like. On their outer surface these microorganisms may possess sulphated and/or phosphorylated structures which could represent a target for DMBT1.

Thus, in a preferred embodiment of the present invention the agent is a microorganism.

The term "microorganism" refers to a small uni- or multicellular organism with dimension beneath the limits of vision which can be propagated and manipulated in a laboratory. In the context of the present invention, "microorganism" includes viruses, prokaryotes like gram-positive and gram-negative bacteria, cyanobacteria, Mollicutes and unicellular eukaryotes (protozoa) like certain genera of fungi, algae and parasites (e.g. sporozoa). It is known to the skilled artisan that microorganisms as defined supra possess on their surface sulphated and phosphorylated structures and molecules. Examples include lipoteichoic acid (LTA) on the surface of gram-positive bacteria or lipopolysaccharide on the surface of gram-negative bacteria.

Preferably, the microorganism is a bacterium or a virus, the bacteria including the genera *Streptococcus, Staphylococcus, Escherichia, Helicobacter, Salmonella* and *Bacillus*.

In a particularly preferred embodiment, the present invention refers to the use of a polypeptide comprising the sequence of SEQ ID NO:1, or a functional fragment or derivative thereof, or of a nucleic acid comprising the sequence of SEQ ID NO:2, or a functional fragment or derivative thereof, for the manufacture of a medicament for the treatment of a disease caused by an agent, wherein the agent possesses at least one accessible sulphate and/or at least one accessible phosphate group and
wherein the agent is not HIV, influenza A virus, *Streptococcus mutans, Streptococcus gordonii, Streptococcus sobrinus, Streptococcus mitis, Streptococcus oralis Streptococcus intermedius, Streptococcus anginosus, Actinobacter actinomyces, Prevotella intermedia, Peptostreptococcus micros, Moraxella catarrhalis, Streptococcus pyogenes, Streptococcus agalactiae, Streptococcus sanguis, Streptococcus pneumonia, Klebsiella oxytoca, Escherichia coli, Haemophilus influenza, Staphylococcus aureus, Helicobacter pylori* or *Bacteroides fragilis*.

Furthermore, many diseases are caused by small chemical compounds which are present in food, pharmaceutical and cosmetic preparations, and the like. Like microorganisms, these compounds or compositions can display accessible sulphate or phosphate groups, which can represent a target for DMBT1.

Therefore, in another preferred embodiment of the present invention, the agent is a non-living compound or composition.

In the context of the present invention the term "non-living compound or composition" refers to a compound or composition which is distinguished from the microorganism described supra, in that it is not a living organism but can be defined as a "chemical compound". In general, the term "non-living compound or composition" encompass all small compounds and compositions which have at least one accessible sulphate or at leas one accessible phosphate group. In this manner, the compound or composition can also be a sulphate or phosphate group alone. The compound or composition can either be captured without any further substances or be, but not limited to, e.g. a food component, a pharmaceutical component a cosmetic component, or toxic environmental component.

In a preferred embodiment of the present invention, the non-living compound or composition is selected from the group consisting of DSS, sulphated carbohydrates, preferably heparan sulphate, chondroitin sulphate, carrageenan, disodium sulphate, liposomes, phosphate group exposing compounds or compositions, preferably DNA, deoxynucleotides, surfactant phospholipids, sulphated mucins, sodium-, potassium- and calcium phosphate exposing compounds or compositions.

The "medicament" of the present invention is useful for the treatment of a patient suffering from a disease caused by an agent which possesses at least one accessible sulphate and/or at least one accessible phosphate group. The polypeptide or nucleic acid contained in the medicament can be administered alone or in combination with one or more active compounds. In a preferred embodiment, the medicament comprises an effective dose of polypeptide comprising the sequence of SEQ ID NO:1, or a functional fragment or derivative thereof, or a nucleic acid comprising the sequence of SEQ ID NO:2, or a functional fragment or derivative thereof, and a pharmaceutically acceptable carrier. i.e. one or more pharmaceutically acceptable carrier substances and/or additives.

The medicament according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example on the disease to be treated and on its severity.

The manufacturing of the medicament can be carried out in a manner known per se. To this end, the polypeptide comprising the sequence of SEQ ID NO:1, or a functional fragment or derivative thereof or a nucleic acid comprising the sequence of SEQ ID NO:2, or a functional fragment or derivative thereof, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the polypeptide of the present invention and to use the resulting lyophilisates, for example, for preparing preparations for injection or infusion. Suitable carriers for microcapsules, implants or rods are, for example, copolymers of glycolic acid and lactic acid. The medicament can also contain additives, for example fillers, disintegrants, binders, lubricants, wetting agents, stabilizers, emulsifiers, dispersants, preservatives, sweeteners, colorants, flavorings, aromarizers, thickeners, diluents, buffer substances, solvents, solubilizers, agents for achieving a depot effect, salts for altering the osmotic pressure, coating agents or antioxidants. The dosage of the medicament of the polypeptide of the present invention to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, or on whether the therapy is acute or chronic or prophylactic.

In a preferred embodiment, the disease to be treated with the medicament of the present invention is an infectious disease caused, e.g. by bacteria, viruses, fungi or protozoa Infectious diseases include bacterial and mycotic diseases, viral and rickettsial diseases, parasitic diseases, and vector-borne infectious diseases.

Some examples of infectious diseases, to which the present invention is not restricted to, include AIDS, cholera, malaria, Dengue, epidemic dysentery, influenza, poliomyelitis, tuberculosis, Typhoid Fever, Yellow Fever, amoeba disentery, anthrax, lung inflammation, bilharziosis, borreliosis, botulism, BSE, campylobacter, Chagas disease, Creutzfeldt-Jakob disease, diphtheria, Ebola virus disease, Echinococcus infection, cold, fatal familial insomnia, fish tapeworm, typhoid fever, river blindness, meningoencephalitis, athlete's foot, gas gangrene, yellow fever, shingles, tularemia, gastritis, hepatitis, herpes simplex—type 1, herpes simplex—type 2, herpes zoster, dog tapeworm, influenza, Japanese encephalitis, candidiosis, pertussis, bone marrow inflammation, cutane leishmaniosis, kuru, lambliasis, Lassa fever, legionellosis, leprosy, listeriosis, pneumonia, lyme borreliosis, measles, mouth and foot disease, bacterial meningitis, anthrax, inflammation of the middle ear, mononucleosis, mumps, noma, Norwalk virus infection, river blindness, osteomyelitis, paratyphoid fever, mononucleosis, Pityriasis versicolor, smallpox, polio, Reiter syndrome, mad cow disease, bovine tapeworm, Rocky Mountain spotted fever, dysentery, enteric fever, salmonellae paratyphoid fever, salmonellae typhoid fever, SARS, schistosomiasis, sleeping sickness, pig tapeworm, sexually transferable diseases, canker sore, rabies, toxoplasmosis, scrapie, trichomoniasis, trichophytia, Tsutsugamushi fever, trypanosomiasis, tuberculosis, tularemia, typhoid fever, visceral leishmaniosis, West Nile fever, chickenpox, dwarf tapeworm.

In another preferred embodiment, the disease is an acute or chronic inflammation. Examples of inflammatory diseases include, but are not restricted to, caries, endocarditis, periodontitis, tonsillitis, pharyngitis, cellulites, scarlet and rheumatoid fever, gastritis, chronic fatigue syndrome, spondylitis, arthritis, preferably inflammatory bowel disease, more preferably ulcerative colitis.

In another preferred embodiment, the disease is cancer. Examples of cancer types comprise neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeolid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma.

In a particularly preferred embodiment, the cancer is a cancer of the respiratory or alimentary tract, such as lung, gastric or colorectal cancer.

Considering the finding of the present invention, that the polypeptide of the present invention may generally bind to sulphate and phosphate groups, it is feasible to assume that it can be used as a general identifier for such agents.

Therefore, another aspect of the present invention refers to the use of a polypeptide comprising the sequence of SEQ ID NO:1, or a functional derivative or fragment thereof, or of a nucleic acid comprising the sequence of SEQ ID NO:2, or a functional fragment or derivative thereof, for identifying an agent and/or regulating the effective amount of an agent in a sample, the agent possessing at least one accessible sulphate and/or at least one accessible phosphate group.

The term "polypeptide comprising the sequence of SEQ ID NO:1, or a functional derivative or fragment thereof" refers to the definitions given supra. In addition, for the purpose of identifying a disease-causing agent, the "functional derivative" encompasses polypeptides which are labelled in order to facilitate their detection. Suitable and well-known labels for proteins include radioactive labels, hemagglutinin, biotin, c-myc, FLAG-tag, digoxygenin, horseradish peroxidase, green fluorescent protein (GFP) and derivatives thereof, beta-galactosidase, luciferase, and beta-glucuronidase.

The term "nucleic acid comprising the sequence of SEQ BD NO:2, or a functional fragment or derivative thereof" refers to the definitions given supra.

The term "identifying" means analysing, whether a sample contains an agent possessing at least one accessible sulphate and/or at least one accessible phosphate group. As such, the polypeptide of the present invention is used due to its capability of binding to accessible sulphate and phosphate groups. Briefly, the sample is incubated with h a preparation of the polypeptide. It is advantageous, that for the purpose of identifying that the polypeptide is labelled with either of the labelling agents described supra in the context of a "functional derivative". If the labelled polypeptide is subsequently detected via a suitable detection method, depending on the type of label, it may have acquired a higher molecular weight due to a probably bound agent as compared to free polypeptide.

In the context of the present invention "regulating the effective amount" can mean either maintaining or decreasing the effective amount. If the presence of an agent, after being identified by the polypeptide, is desired, no further polypeptide will be added, or, if the polypeptide is already present, it will be depleted from the sample. The latter aspect is described in greater detail below in the context of "varying the amount". An "effective amount" of an agent comprises that amount of an agent which is sufficient and/or required to alter a condition which is prevalent in the absence of the agent.

The term "agent" refers to the definition of an agent given supra.

In a preferred embodiment, the identifying and/or regulating is carried out by using the at least one accessible sulphate and/or at least one accessible phosphate group. The efficacy of the identifying and/or regulating is mediated by the interaction of the polypeptide of the present invention with an accessible sulphate or phosphate group displayed or exposed by the agent present in the sample. Depending on the type of interaction, i.e. whether it is, inter alia, a covalent, non-covalent, transient, permanent, via hydrophobic interactions, and the like, the interaction can be strong and weak.

Another possibility to influence the strength and/or efficiency of the interaction between the polypeptide and the agent can be achieved by varying the amount or the length of the polypeptide. As demonstrated in the example section and already pointed out in the introduction, the interaction of DMBT1 with sulphate/phosphate groups is mediated by a 11-amino acid stretch on DMBT1. Furthermore, an enhanced susceptibility to a sulphate/phosphate group possessing agent if a shortened form of DMBT1, having less binding regions for said agent is observed.

Therefore, in another preferred embodiment, the identifying and/or regulating is carried out by varying the amount and/or the length of the polypeptide.

"Varying the amount and/or the length of the polypeptide" can occur both on the protein level and on the nucleic acid level. If it occurs on the protein level the amount can be increased by just adding and/or supplementing to the sample a suitable amount of the polypeptide, which is required or sufficient to bind at least 50%, at least 60%, at least 70%, at least 80%, preferably at least 95% of agents which possess accessible sulphate and phosphate groups. If DMBT1 should be depleted from a sample in order to maintain a certain amount of sulphate/phosphate group possessing agents, the use of an antibody directed against DMBT1 for immunoprecipitation of DMBT1 can be envisaged. Antibodies include anti-idiotypic antibodies which recognize unique determinants generally associated with the antigen-binding site of an antibody. Potential DMBT1 depleting compounds also include compounds, compositions and proteins which are closely related to ligands of the DMBT1, i.e. a fragment of the ligand, which have lost biological function and when binding to DMBT1, elicit no response. A small molecule which binds to DMBT1, making it inaccessible to ligands such that normal biological activity is prevented for example small peptides or peptide-like molecules, may also be used for inhibition. Particularly useful for depleting DMBT1 will be compounds, compositions and proteins which possess accessible sulphate and/or phosphate groups.

Another possibility is "varying the amount and/or the length of the polypeptide" on the nucleic acid level. For the purpose of increasing the DMBT1 expression the nucleic acid encoding DMBT1 may be introduced into the target cell, as described further below in the context of therapeutic uses and methods. An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of DMBT1. The antisense RNA oligonucleotide hybridizes to the mRNA in vivo and blocks translation of mRNA molecules into DMBT1 (antisense—Okano, J. Neurochem., 56:560 (1991); Oligodeoxynucleotides as Antisense Inhibitors of Gene Expression, CRC Press, Boca Eaton, Fla. (1988)). The oligonucleotides described above can also be delivered to cells such that the antisense RNA or DNA may be expressed in vivo to inhibit production of DMBT1. Furthermore, the expression of DMBT1 can be down-regulated by RNA interference, exploiting double-stranded siRNA which can be synthesized by using the sequence of SEQ ID NO:2.

In a preferred embodiment, regulating the effective amount of an agent includes inactivating and/or capturing said agent.

"Inactivating/capturing" generally refers to diminishing or completely abolishing the activity of the agent which possesses accessible sulphate and/or phosphate groups, as compared to the activity in the absence of the polypeptide or nucleic acid of the present invention. A suitable test system for measuring the activity, and respectively, the decrease of the activity of the agent is provided in the "MATERIAL AND METHODS" section of the present invention ("turbidometric aggregation assays)

For the use of the present invention, which is carried out preferably in vitro, the sample can be any sample which is supposed to contain an agent, which possesses at least one sulphate and/or at least one phosphate group. The sample can for example be a biological, a food-derived, a pharmaceutical or a cosmetic sample.

Another aspect of the present invention is the use of DMBT1, or the nucleic acid encoding it, as a diagnostic tool to detect and quantify the expression of DMBT1 in an individual, and deducing from the expression pattern a potential risk or susceptibility of the individual for an infectious, inflammatory disease or cancer. This can be carried out by analyzing any of a potential patient's body fluid, such as serous effusions (blood), semen, vaginal secretions, saliva, cerebrospinal fluid, sweat, tear fluid, pleural and pericardial fluid, peritoneal fluid, synovial fluid and amniotic fluid. Therefore, this invention is also related to using DMBT1, and respectively the nucleic acid encoding it, to detect polypeptides or complementary polynucleotides, for example, as a diagnostic reagent for a variety of diagnostic purposes as described below.

In this respect, another aspect of the present invention refers to the, preferably in vitro, use of a polypeptide comprising the sequence of SEQ ID NO:1, or a functional fragment or derivative thereof, or of a nucleic acid comprising the sequence of SEQ ID NO:2, or a functional fragment of derivative thereof for the manufacture of a diagnostic for diagnosing the susceptibility of an individual to an agent, wherein the agent possesses at least one accessible sulphate and/or at least one accessible phosphate group.

Some pharmaceutical preparations are contained within or associated with carriers which possess accessible sulphate and/or phosphate groups. Perhaps they are embedded in liposomes or other structures exposing sulphate or phosphate groups. This may lead to the effect that the DMBT1 being present in an individual may bind the pharmaceutical-bearing carrier and, as a consequence, decreasing the amount of a free and effective pharmaceutical. The effective dose of such a pharmaceutical would then have to be increased if the amount of the DMBT1 polypeptide is high or if many sulphate/phosphate binding SRCR domains are present.

Therefore, another aspect refers to the, preferably in vitro, use of a polypeptide comprising the sequence of SEQ ID NO:1, or a functional or fragment derivative thereof, or a nucleic acid comprising the sequence of SEQ ID NO:2, or a functional or fragment derivative thereof, for the manufacture of a diagnostic for determining in an individual the effective dose of a pharmaceutical comprising an agent, wherein the agent possesses at least one accessible sulphate and/or at least one accessible phosphate group.

Furthermore, the invention refers to a method for diagnosing the susceptibility of an individual to an agent which possesses at least one sulphate and/or at least one phosphate group, the method comprising detecting in a sample a polypeptide comprising the sequence of SEQ ID NO:1, a functional fragment or derivative thereof, or a nucleic acid comprising the sequence of SEQ ID NO:2, or a functional or fragment derivative thereof, wherein a shortened polypeptide or a nucleic acid as compared to the full length polypeptide or nucleic acid is indicative of an increased susceptibility.

"Detecting" a shortened DMBT1 associated with a dysfunction as compared to the full-length DMBT1 will provide a diagnostic tool that can add or define a diagnosis of a disease or susceptibility to a disease which results from under-expression over-expression or altered-expression of DMBT1, or alterations of the DMBT1 gene structure. Binding and hybridization assays can be used to detect, prognose, diagnose, or monitor disease (including conditions and disorders) associated with DMBT1. This includes both the detection of the nucleic acid that encodes DMBT1, and the detection of the DMBT1 protein. Appropriate detection methods include biochemical methods such as spectrophotometry, radiography, gel electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion, immunoelectrophoresis, radioimmunoassays (RIAs), enzyme-linked immunosorbent assays (ELISA), immunofluorescence assays, tissue array, and the like.

A shortened or full-length DMBT1 gene may be detected at the DNA level by a variety of techniques. Nucleic acids for diagnosis may be obtained from a patient's cells, such as from blood, urine, saliva, tissue biopsy and autopsy material. The genomic DNA may be isolated after well-known methods and used directly for detection or may be amplified enzymatically by using PCR prior to analysis. PCR (Saiki et al., Nature, 324:163-166 (1986)). RNA or cDNA may also be used in the same ways. As an example, PCR primers complementary to the nucleic acid encoding DMBT1 can be used to identify, and analyze DMBT1 expression and deletions. For example, deletions and insertions can be detected by a change in size of the amplified product in comparison to the normal genotype. Sequence differences between a reference gene and genes having deletions also may be revealed by direct DNA sequencing. In addition cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabelled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)). A deletion may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of at least 15 consecutive bases, and may contain at least 30 or even 50 consecutive bases.

Hybridization techniques are frequently used for detecting nucleic acids and the present invention contemplates all available hybridization techniques, including Southern, Northern and in situ hybridization techniques, dot blot analysis, cDNA arrays. Expression of the DMBT1 mRNA may be detected, for example, by Northern analysis, or by reverse transcription and amplification by PCR. Also contemplated are nucleic acid detection and quantification methods which employ signal moieties that are conjugated to nucleic acid probes, e.g. by incorporation of radioactively labeled nucleotides. Nucleic acids in a sample can be immobilized on a solid support and hybridized to such probes. The signal moiety can be detected directly, for example by fluorescence. Alternatively, the signal moiety may be detected indirectly by its enzymatic activity, for example in an ELISA or other colorimetric assay. Hybridization techniques are usually performed by providing a sample of tissue or cells, contacting the sample with a labeled probe, that binds to said nucleic acid molecule, and determining the presence or amount of the probe bound to said nucleic acid molecule, thereby determining the presence or amount of the nucleic acid molecule in said sample.

Methods to detect the presence and amount of the DMBT1 protein in a sample are well known to the person skilled in the art. Briefly, a sample is provided said sample is contacted with an antibody that immunospecifically binds to DMBT1 and the presence or amount of antibody bound to DMBT1 is determined, whereby the presence or amount of DMBT1 in said sample is determined. Methods to determine the amount and presence of polypeptides comprise, among others, FACS, Western blotting, immunoprecipitation, ELISA, and RIA. It is advantageous if the antibody used for detection is conjugated to a molecule that enables and contributes to the detection. Suitable molecules comprise biotin, horseradish peroxidase, alkaline phosphatase, fluorescein isothiocyanate (FITC), tetramethylrhodamine isothiocyanate (TRITC), diamidinophenylindol (DAPI) and phycoerythrin.

In accordance with the aspect described supra, the present invention refers to a method for determining in an individual the effective amount of a pharmaceutical comprising an agent which possesses at least one accessible sulphate and/or at least one accessible phosphate group, the method comprising detecting in a sample a polypeptide comprising the sequence of SEQ DID NO:1, a functional fragment or derivative thereof or a nucleic acid comprising the sequence of SEQ ID NO:2, or a functional or fragment derivative thereof,
wherein a shortened polypeptide or nucleic acid as compared to the full-length polypeptide or nucleic acid is indicative for a lower effective amount of the pharmaceutical.

The method can be applied to any sample which is suitable for DNA analysis. For example, the sample can be a body fluid, preferably blood, saliva, semen or liquor, which is isolated from the individual according to method known to the person skilled in the art.

According to the present invention, the uses provided herein indicate that DMBT1 can generally act as a potential pan-acting pharmaceutical against diseases caused by agents which possess accessible sulphate and/or phosphate groups.

In line with the provided uses, the invention furthermore refers to a method for the treatment and/or prophylaxis of a disease caused by an agent which possesses at least one accessible sulphate and/or at least one accessible phosphate group, the method comprising contacting the agent with a polypeptide comprising the sequence of SEQ ID NO:1, or a functional or fragment derivative thereof.

The "contacting" typically occurs in an individual who has, for example, been identified as having an increased susceptibility to agents, which possess accessible sulphate or phosphate groups, and, thus, having an increased risk of being affected by a disease caused by such an agent. In order to allow for efficient contacting between an effective dose of DMBT1 and the disease-causing agent in the individual, the available amount of DMBT1 in the individual may be increased by supplementing for additional DMBT1. The expression or the amount of DMBT1 can be increased by several methods known in the art, e.g. as described below.

Preferably, the contacting is carried out by administering to a patient a pharmaceutical preparation containing a polypeptide comprising the sequence of SEQ ID NO:1, or a functional or fragment derivative thereof, or a nucleic acid comprising the sequence of SEQ ID NO:2, or a functional derivative thereof.

In order to increase the DMBT1 expression in a patient, the nucleic acid encoding DMBT1, as defined by SEQ ID NO:2, may be introduced into a cell. For the introduction of DMBT1, respectively the nucleic acid encoding it, into the cell and its expression it can be advantageous if the DMBT1 encoding nucleic acid is integrated in an expression vector. The expression vector is preferably a eukaryotic expression vector, or a retroviral vector, a plasmid, bacteriophage, or any other vector typically used in the biotechnology field. If necessary or desired, the nucleic acid encoding DMBT1 can be operatively linked to regulatory elements which direct the transcription and the synthesis of a translatable mRNA in pro- or eukaryotic cells. Such regulatory elements are promoters, enhancers or transcription termination signals, but can also comprise introns or similar elements, for example those, which promote or contribute to the stability and the amplification of the vector, the selection for successful delivery and/or the integration into the host's genome, like regions that promote homologous recombination at a desired site in the genome. For therapeutic purposes, the use of retroviral vectors has been proven to be most appropriate to deliver a desired nucleic acid into a target cell.

The invention is further illustrated by, but not restricted to the following examples:

EXAMPLE 1

Minimal Sequence of the Bacterial Binding Site of DMBT1

Figure 1:
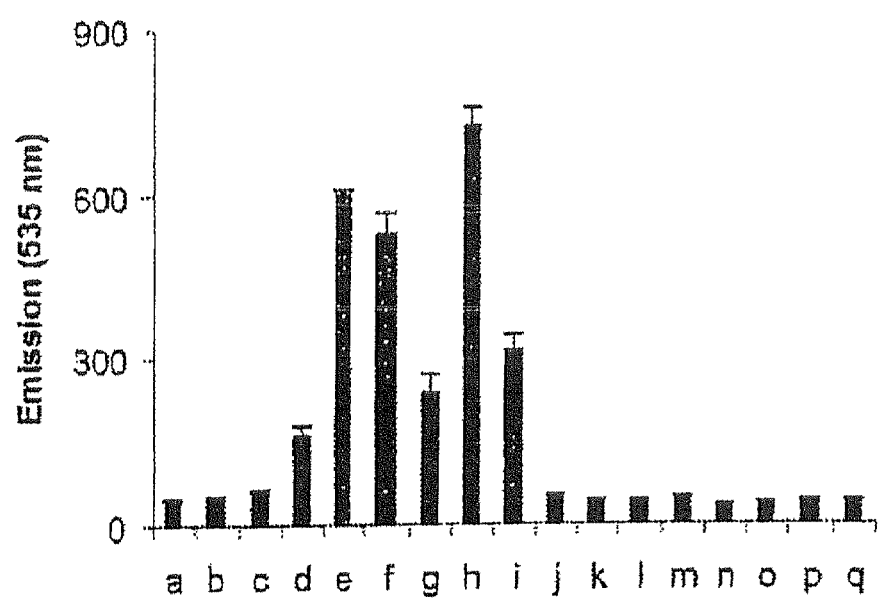
FIG. 1 Definition of the DMBT1 pathogen-binding site. a, Domain structure of the DMBT1-variant presumably expressed from the largest (wild type) DMBT1 allele (DMBT1$^{wt}$) with the position of the synthetic peptides in the consensus sequence (SEQ ID NO: 12) of the 13 amino-terminal SRCR domains depicted below. Peptides in red mediated aggregation and peptides marked with asterisks exerted activity in binding of Gram-positive *S. mutans* and Gram-negative *E. coli* bacteria. The 11 amino acid stretch marked in red in the SRCR consensus is the minimal pathogen-binding site (DMBT1pbs1) predicted from these assays. Pink triangle: leader peptide; blue box: DMBT1-specific motif; red ovals: SRCR domains; orange ovals: SRCR interspersed domains (SIDs); purple boxes: C1r/C1 s-Uegf-Bmp1 (CUB) domains; green oval: *zona pellucida* (ZP) domain; EHD: ebnerin-homologous domain. b, The results from binding analyses with *S. mutans* are shown. Colour and alphabetical codes correspond to these in FIG. 1*a*. Error bars are SEM. c, Confirmation of the minimal binding site DMBT1pbs1. The top panel summarizes the results of binding (B) and aggregation (A) studies with DMBTIpbs1 and amino- and carboxy-terminally truncated variants of the peptide sequence. (+) binding and aggregation activity; (−) no binding and no aggregation activity. The graphs below display the aggregation of Gram-positive *S. gordonii* (purple) and *S. mutans* (red) and of Gram-negative *H. pylori* (dark blue) and *E. coli* (light blue) in the presence (top graph) and absence (bottom graph) of the DMBT1pbs1-peptide. d, Analysis of critical amino acid residues and corresponding motifs in related proteins. The graph at the left displays the impact of amino acid substitution by alanine of the residues depicted on the right. Binding activity to *S. mutans* is expressed as percent compared to DMBT1pbs1, which served as positive control (PC). SRCRP1 without substantial binding activity was included as negative control (NC). Error bars are SEM. Amino acid residues critical for binding are marked in orange. The right panel summarizes the results from DMBT1pbs1-corresponding motifs in other SRCR proteins. (B) and (A) denote group B and group A SRCR proteins. (+) bacterial binding and aggregation activity and (−) no bacterial binding and aggregation activity with both Gram-positive *S. mutans* and Gram-negative *E. coli*. Amino acids diverging from DMBT1pbs1 are marked in blue. Boxed residues are compatible substitutions. h: human; r: rabbit; c: cattle; m: mouse. Note that sequence variations present in the 13 amino-terminal domains of human DMBT1 and in its orthologs in other species are allowed. The motif present in SRCR14 of DMBT1 and, for example, the corresponding motifs of the Mac-2 bp and MARCO did not exert binding or aggregation activity. e, Quantitative and qualitative differences between the DMBT1pbs1-motifs present in the SRCR domains of DMBT1. Motifs present in SRCR1, SRCR2-7, SRCR9-11, and SRCR13 exerted best binding and aggregation activity (results shown for *S. mutans*). While the motif present in SRCR8 and SRCR12 was less active, the motif in the carboxy-terminal SRCR14 exerted no activity at all.
Figure 1:
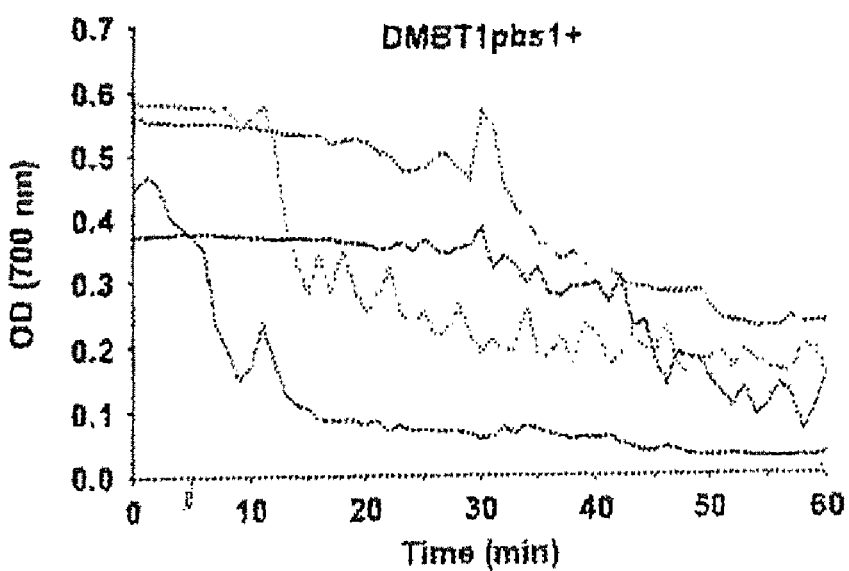
Figure 1:
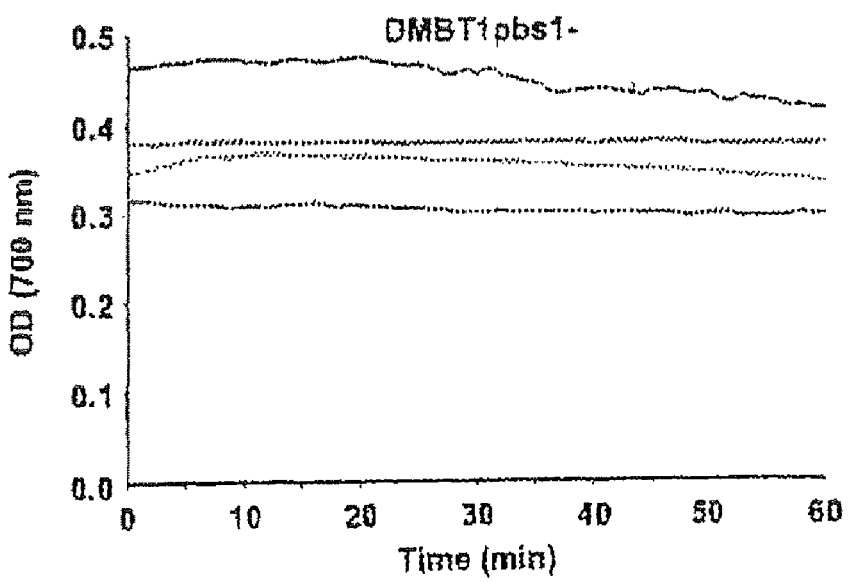
Figure 1:
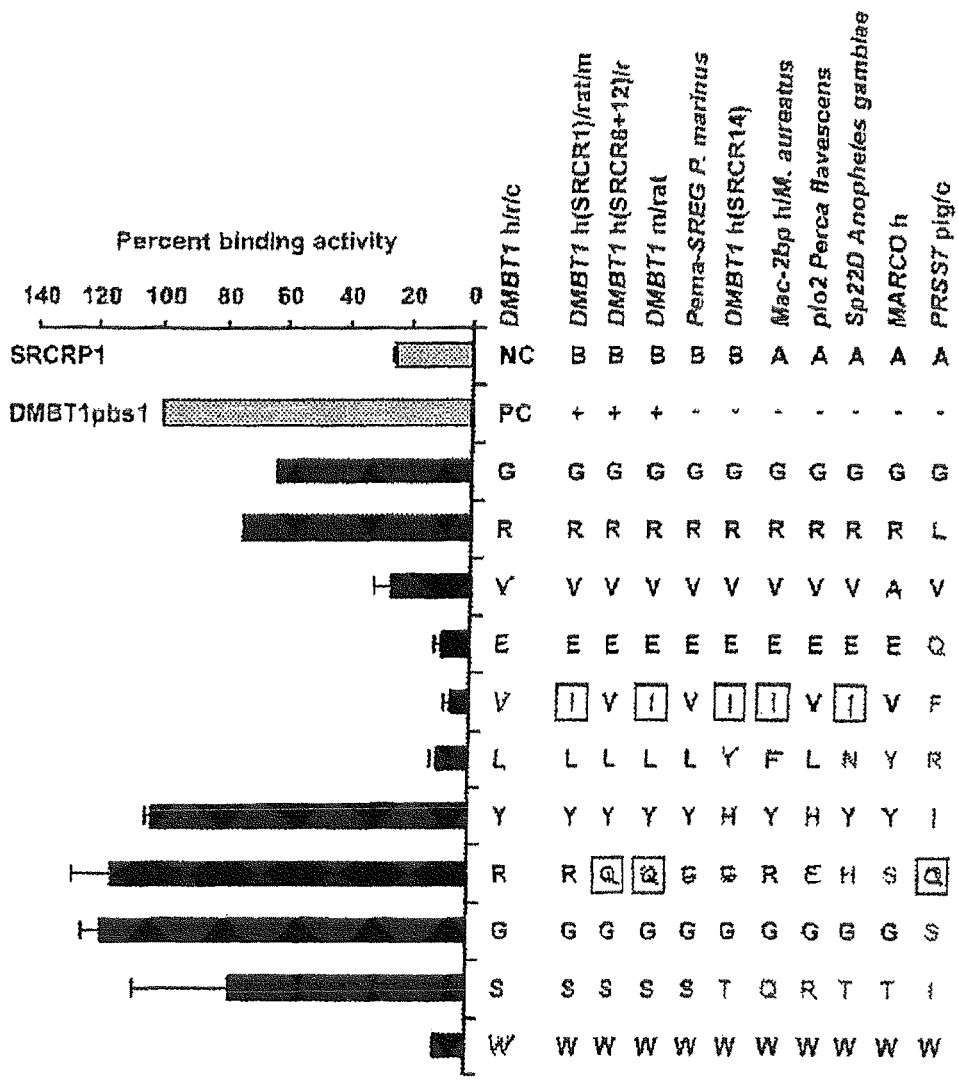
Figure 1:
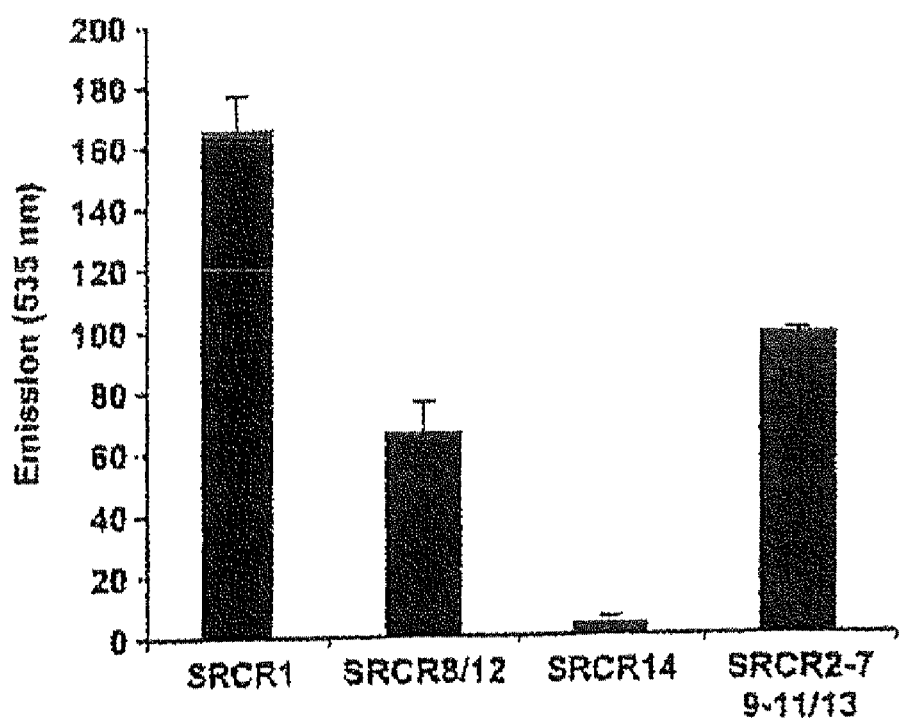
Figure 1:
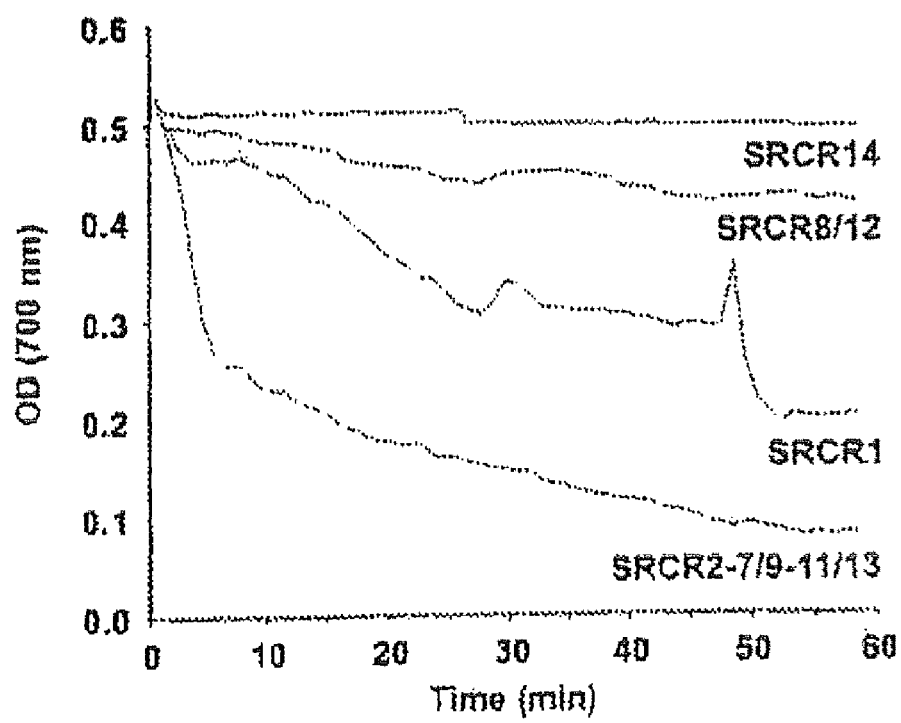

Initially, it was intended to refine in more detail the bacterial binding site of DMBT1, which we previously mapped to a 16 amino acid motif (designated as SRCRP2) present in most of its scavenger receptor cysteine-rich (SRCR) domains. We identified a minimal sequence of 11 amino acids (GRVEVLYRGSW (SEQ ID NO: 9); DMBT1 pathogen-binding site 1; DMBT1pbs1) to be sufficient and necessary for interaction with Gram-positive and -negative bacteria (FIG. 1 a-c). Corresponding motifs present in the 13 amino-terminal SRCR domains of DMBT1 and in its orthologs in other species (mouse, rat, rabbit, cattle) likewise exerted bacterial binding activity, but not these in SRCR14 of human DMBT1 or in other SRCR proteins (FIG. 1d, e). This strongly suggests functional equivalence of DMBT1 and its orthologs, while its fourteenth SRCR domain probably is functionally distinct. Besides DMBT1, only the group A SRCR proteins SR-A and MARCO, which are cell surface receptors on immune cells, is demonstrated to interact with bacteria. While the positively charged RXR motif mediates binding of MARCO to polyanionic substances by electrostatic interactions, we identified the negatively charged motif VEVL (SEQ ID NO: 15) and a terminal tryptophan residue as critical for DMBT1pbs1 (FIG. 1d), pointing to a distinct mode of pathogen-recognition.

EXAMPLE 2

Screening for DMBT1 Ligands

We considered DMBT1pbs1-mediated bacterial aggregation as potentially useful and simple high-throughput competition assay to screen for DMBT1 ligands and to determine its binding specificity. Dextran sulfate sodium (DSS) and its analogue carrageenan, which is broadly used as thickener and stabilizer in human food, exert deleterious effects in the gastrointestinal tract as multiply demonstrated by induction of tissue damage, inflammation, and cancer in animal models.

Figure 2:
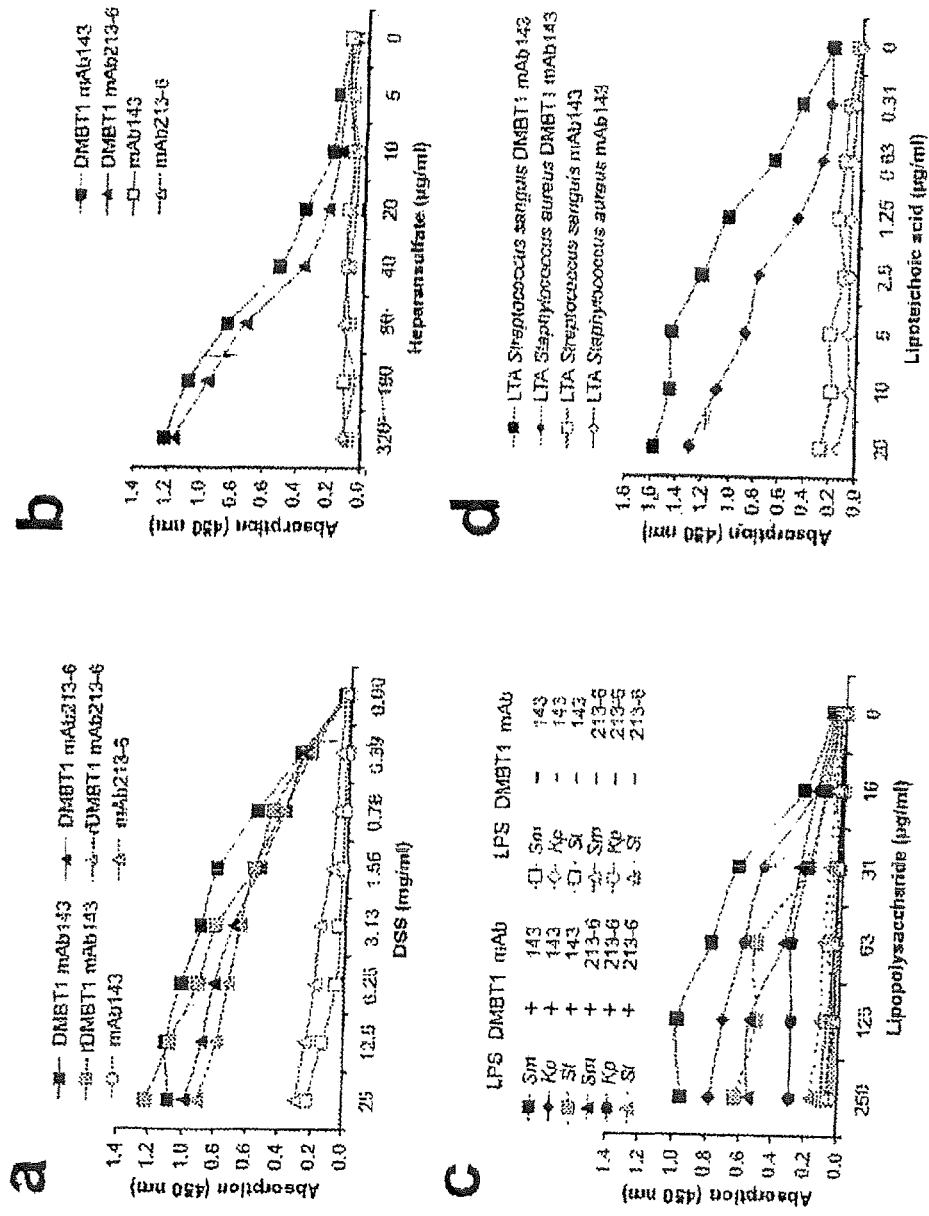
FIG. 2 Confirmation of DMBT1 interaction with candidates retrieved from the high-throughput screen. DMBT1 denotes purified DMBT1 from saliva (also known as salivary agglutinin; DMBT1$^{SAG}$), rDMBT1 is purified recombinant human DMBT1. a, DMBT1 binding to DSS. Note that DMBT1 and rDMBT1 showed virtually identical binding properties. b, DMBT1 interaction with heparansulfate. c, DMBT1 interaction with lipopolysaccharide (LPS) of *Salmonella minnesota* (Sm; corresponds to the Rd1 chemotype in FIG. 4a), *Klebsiella pneumoniae* (Kp), and *Salmonella typhimurium* (St, corresponds to wild type in FIG. 4a). Note that DMBT1 more efficiently bound to LPS from *S. minnesota* chemotype Rd1 than to LPS from wild type *S. typhimurium*. d, DMBT1 binding to lipoteichoic acid (LTA). e, DMBT1 interaction with immobilized DNA. f, Interaction of DNA with immobilized rDMBT1. g, DMBT1 binding to the phospholipid L-phosphatidylcholine. h, Effects of sIgA on DMBT1- and DMBT1pbs1-meditated bacterial binding. *S. mutans* binding was investigated with or without prior preincubation of immobilized DMBT1 or DMBT1pbs1 with 5 µg/ml sIgA, which is a known DMBT1 interaction partner. The presence of sIgA, did neither enhance nor inhibit bacterial binding, indicating interaction with DMBT1 via a site that is distinct from DMBT1pbs1.
Figure 2:
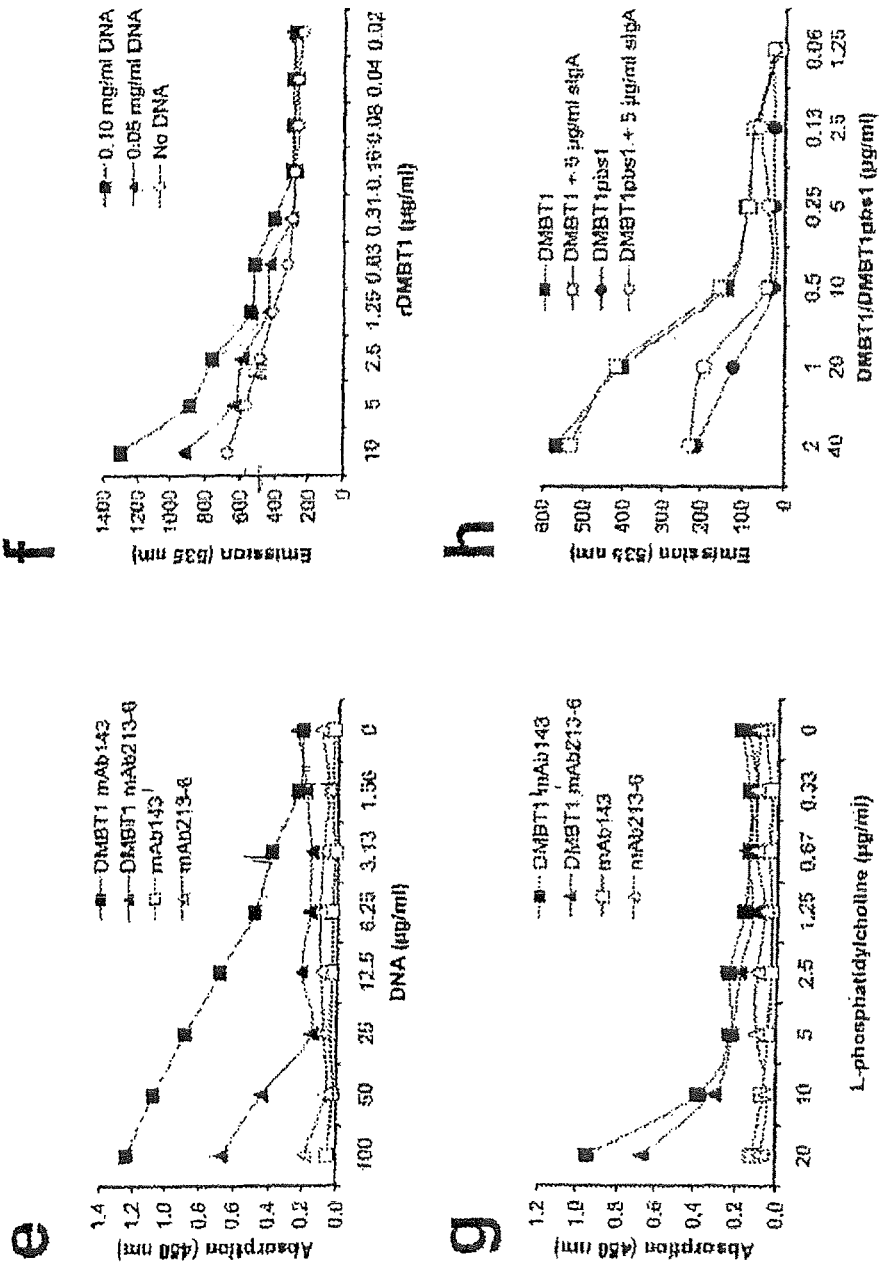
Figure 3:
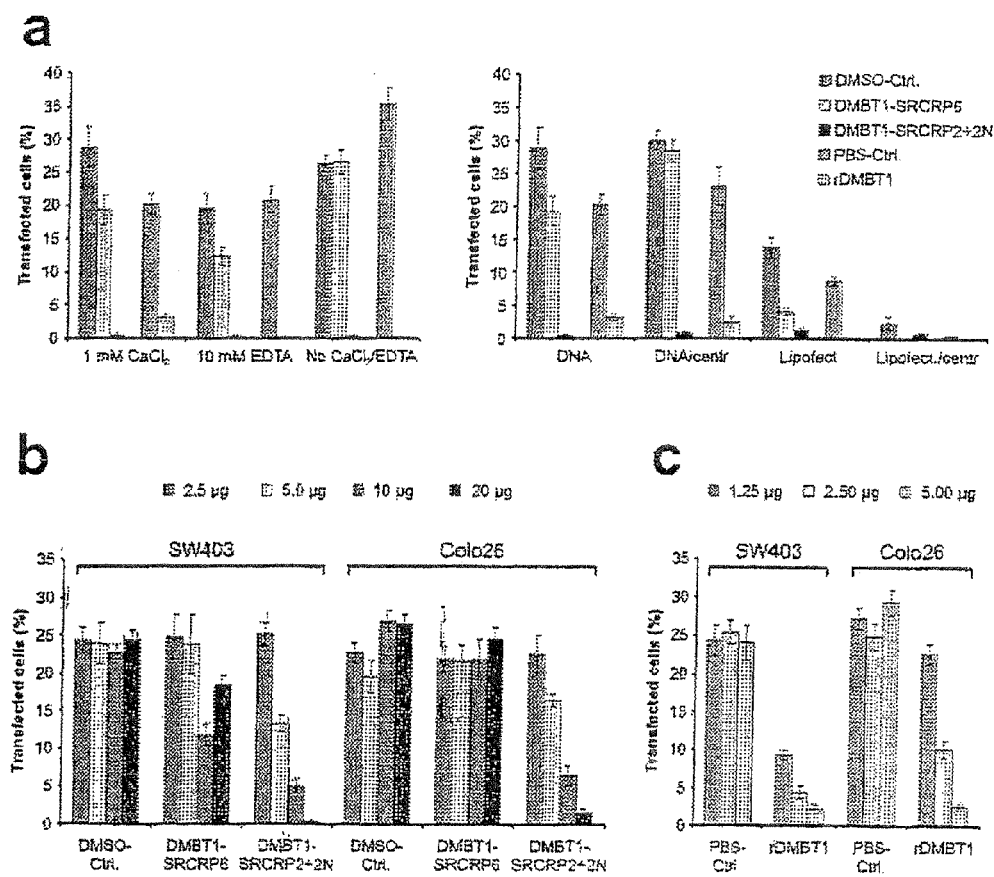
FIG. 3 DMBT1 inhibits liposome-mediated DNA-transfer to mammalian cells by interaction via its pathogen-binding site. Error bars are SEM. a, Determination of the assay conditions. Left panel: 0.5 µg plasmid DNA (pEGFP-N1) was preincubated with the synthetic peptides SRCRP2+2N (containing DBT1pbs1; 20 µg) or SRCRP6 (control; 20 µg), a corresponding volume of 10% DMSO in H$_2$O (DMSO-Ctrl.), with rDMBT1 (5 µg) in PBS or with PBS alone (PBS-Ctrl.) in the presence or absence of 1 mM CaCl$_2$ or 10 mM EDTA, respectively. After addition of Lipofectamine 2000, the cells (SW403) were transfected and the percentage of green fluorescent cells was scored 24 h post transfection. SRCRP2+2N and rDNBT1 exerted strong inhibitory effects compared to controls irrespective of the presence of CaCl$_2$ or EDTA. Subsequent assays were thus carried out without addition of CaCl$_2$ or EDTA. Right panel: SRCRP2+2N and rDMBT1 exerted inhibitory effects regardless of whether the plasmid DNA or the Lipofectamine 2000 (Lipofect) were preincubated DNA/centr. and Lipofect./centr. are experiments in which the samples were centrifuged after preincubation and the supernatants were used for transfection. This particular approach was uninformative for the phospholipids, because centrifugation was unfavorable for Lipofectamine 2000 (right group of columns). Peptide SRCRP6 was included as additional control for unspecific interactions. b and c, Concentration-dependent inhibition of liposome-mediated DNA-transfer by SRCRP2+2N and by rDMBT1 in two mammalian cell lines of colon epithelial origin (SW403: human; Colo26: mouse). Results with preincubation of DNA (without centrifugation) are shown. In DMSO-Ctrl. and PBS-Ctrl. solvent concentrations were used that were matched to the respective peptide and rDMBT1 solutions. d, Exemplary images of the cells 24 h post transfection after DNA-preincubation (magnification: 200-fold). e, Precipitation experiments. Addition of SRCRP2+2N led to visible precipitates after centrifugation (location marked by red broken lines) indicating that co-precipitation of DNA and Lipofectamine, respectively, might have led to a physical depletion from the supernatants that subesequently showed reduced transfection efficacies.
Figure 3:
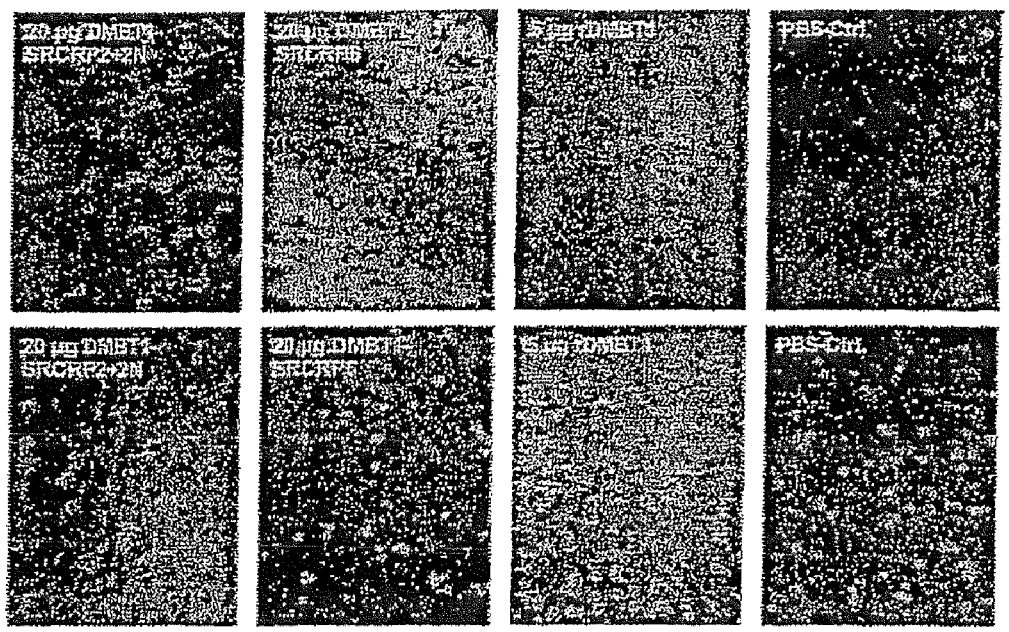
Figure 3:
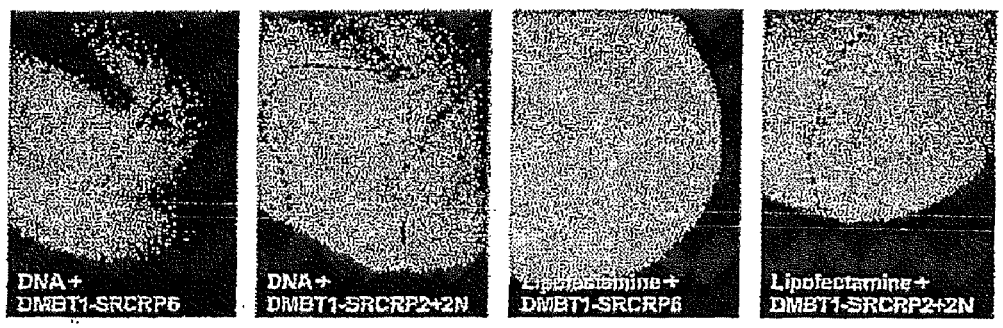

Because Dmbt1$^{-/-}$ mice showed deficient protection against DSS (Bergmann et al., submitted), we initially hypothesized a direct interaction between DMBT1pbs1 and carbohydrate residues. However, in more that 1,000 assays, we identified the sulfate and the phosphate group as DMBT1pbs1 targets (Table 1), which was somewhat unexpected based on the fact that positively charged amino acids were dispensable for binding (FIG. 1d). Potential interaction partners comprised a broad range of sulfated and phosphorylated non-self and self structures (Table 1). All candidate ligands that were subsequently tested using either DMBT1 purified from saliva or recombinantly expressed DMBT1 (rDMBT1) could be confirmed (FIG. 2a-g: Bergmann et al., submitted). Remarkably, sIgA, a known interaction partner of DMBT1 had no impact on DMBT1pbs1-mediated bacterial binding, suggesting a distinct binding site (FIG. 2h). Quantitative inhibition of liposome-mediated DNA-transfer to colon carcinoma cell lines further confirmed interaction with phosphate esters, i.e. DNA and phospholipids (FIG. 3). It indicated that DMBT1 binding might deny access of polyanionic ligands to target cells, which is in line with data obtained from studies of Dmbt1$^{-/-}$ mice (Bergmann et al., submitted).

TABLE 1

Semi-quantitative DMBT1pbs1 high-throughput competition assays

| Substances | Concentration | | pH[a] | Aggregation[b] of S. gordonii | E. coli | Comments[c] | |
|---|---|---|---|---|---|---|---|
| Sulfate groups | | | | | | | |
| Sucrose | 1-500 | mM | co | +++ | +++ | control | no carbo- |
| Maltose | 1-500 | mM | co | +++ | +++ | control | hydr. |
| Glucose | 10-50 | mg/ml | co | +++ | +++ | dextran constituent | binding |
| Dextran sulfate sodium (DSS) | 10-50 | mg/ml | co | − | − | tissue damage/inflammation/ cancer; anti-HIV-drug | defines sulfate group as target structure; |
| Heparan sulfate | 1-5 | mg/ml | co | − | − | role in pathogen-host interaction, cell-surface and ECM | suggests interaction with non-self (DSS, |
| Chondroitin sulfate B | 1-5 | mg/ml | co | − | − | ECM proteoglycan | carrageenan and self structures |
| Degraded lambda-carrageenan | 0.05 | mg/ml | co | ++ | +++ | human food additive, suspected to cause tissue | (e.g. heparansulfate) |
| | 0.1 | mg/ml | co | + | +/++ | damage/inflammation/cancer | |
| | 1-20 | mg/ml | co | +/− | +/− | | |
| Na$_2$SO$_4$ | 1 | mM | co | + | + | control | |
| | 10 | mM | co | +/− | +/− | molarity of sulfate corresponds to the one in 5 mg/ml DSS | |
| | 50-500 | mM | co | − | − | control | |
| Na$_2$SO$_4$/BaOH | 10/1 | mM | co | ++ | ++ | control, Ba$^{2+}$ precipitates SO$_4^{2-}$ | |
| Na$_2$SO$_4$/BaOH | 10/10 | mM | co | +++ | +++ | control, Ba$^{2+}$ precipitates SO$_4^{2-}$ | |
| Na$_2$SO$_4$/BaOH | 10/25 | mM | co | +++ | +++ | control, Ba$^{2+}$ precipitates SO$_4^{2-}$ | |
| BaOH | 5-50 | mM | co | +++ | +++ | control, rules out effects of OH$^-$ | denies unspecific |
| NaOH | 5-50 | mM | co | +++ | +++ | control, rules out effects of OH$^-$ | interaction with |
| NaCL | 1-100 | mM | co | +++ | +++ | control, rules out effects of Cl$^-$ | anions |
| | 500 | mM | co | + | + | control, minor effect of purely electrostatic interactions | |
| KNO$_3$ | 1-100 | mM | co | +++ | +++ | control, rules out interactions with NO$^{3-}$ | |
| | 500 | mM | co | + | + | control, minor effect of purely electrostatic interactions | |
| Chemical carcinogens | | | | | | | |
| Azoxymethane (AOM) | 1-500 | mM | co | +++ | +++ | promotes colon carcinogenesis | no or |
| N-nitrosodiethylamine (DEN) | 1-50 | mM | co | +++ | +++ | promotes liver and esophageal carcinogenesis | poor binding |
| | 100-500 | mM | co | ++ | ++ | | |
| Bacterial cell wall components | | | | | | | |
| LTA (*Streptococcus sanguis*) | 1 | mg/ml | co | − | − | phosphate ester | defines |
| LTA (*Staphylococcus aureus*) | 1 | mg/ml | co | − | − | phosphate ester | bacterial cell |
| LPS (*Escherichia coli*) | 1 | mg/ml | co | − | − | contains phosphorylated carbohydrates | wall comp. as target |
| LPS (*Klebsiella pneumoniae*) | 1 | mg/ml | co | − | − | contains phosphorylated carbohydrates | |
| Phosphate groups | | | | | | | |
| DNA | 5 | μg/ml | co | +/− | +/− | released by apoptotic/necrotic | suggests interaction with |
| DNA | 10-40 | μg/ml | co | − | − | cells, intact DNA-fragments | structures that can be self or |
| dNTP-Mix | 1-8 | mM | co | ++ | ++ | absorbed in by the | non-self (e.g., preserved DNA- |
| dATP | 1-8 | mM | co | ++ | ++ | gastrointestinal tract represent a | fragments from nutrition, phospate esters |
| dTTP | 1-8 | mM | co | ++ | ++ | potential threat, because of | tri bacterial cell wall |
| dCTP | 1-8 | mM | co | ++ | ++ | potential integration into the host | components, phopholipids of |
| dGTP | 1-8 | mM | co | ++ | ++ | cell genome; 5 μg/ml circular plasmid DNA corresponds to 0.015 mM phopshate groups | viral envelopes) |
| CUROSURF ™ (pig surfactant phospholipids) | 1-10% | v/v | co | +/− | +/− | surfactant substitute for premature neonates; equals to | |

TABLE 1-continued

Semi-quantitative DMBT1pbs1 high-throughput competition assays

| Substances | Concentration | pH[a] | Aggregation[b] of S. gordonii | E. coli | Comments[c] |
|---|---|---|---|---|---|
| | | | | | 8 mg/ml phospholipids (mainly phosphatidylcholine) |
| Na$_3$PO$_4$ | 1 mM | co | ++ | ++ | defines phosphate group as |
| | 2-10 mM | co | +/− | +/− | target structure |
| | 50-500 mM | ch | | | |
| K$_2$HPO$_4$ | 1 mM | co | ++ | ++ | |
| | 2-10 mM | co | +/− | +/− | |
| | 50-500 mM | ch | | | |
| KH$_2$PO$_4$ | 1-10 mM | co | + | + | |
| | 50-500 mM | ch | | | |
| Further controls | | | | | |
| Glutamine | 1-250 mM | co | +++ | +++ | no interaction with carboxyl or amide group |
| Aprolinin | 1-5 mg/ml | co | +++ | +++ | no unspecific interaction with proteins |

[a]denotes whether addition of substance in respective solvent resulted in constant pH within allowed range (co) or changed pH (ch) beyond the optimal thresholds (see methods section);
[b]aggregation compared to matched controls, which semi-quantitatively depicts the capacity of the substances to compete for DMBT1pbs1-mediated bacterial aggregation; the range is from (++): no difference in aggregation compared to control to (−): complete inhibition of aggregation under assay conditions (for details refer to methods section);
[c]comments include specification of the respective substances, experimental ratio for their utilization and/or possible implications of the results.

EXAMPLE 3

Binding of Dmbt1 to Bacterial Surface Compounds

Figure 4A:
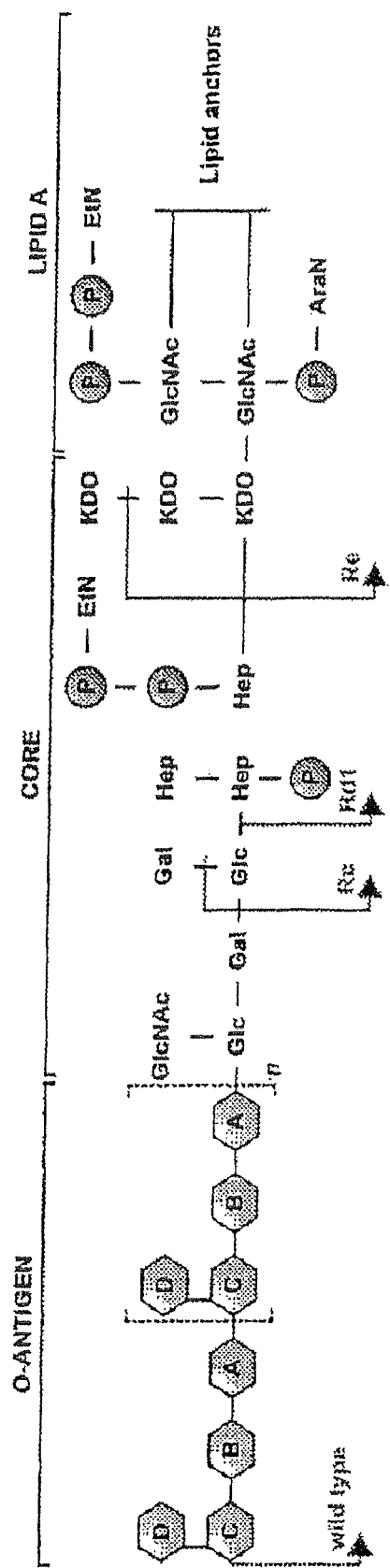
FIG. 4 DMBT1s bacterial scavenging efficacy depends on the accessability and availability of phosphorylated carbohydrates and is impaired by germline deletions. a, Schematical presentation of the LPS structure of *Salmonella*. A-D: carbohydrate residues; AraN: 4-amino-L-arabinose; EtN: ethanolamine; Gal: D-galactose; Glc: D-glucose; GlcNAc: N-acetyl-D-glucosamine, Hep: L-glycero-D-manno-heptose; KDO: 2-keto-3-deoxy-manno-octonate; P: phosphate; Rc, Rd1, and Re are incomplete forms present on the different chemotypes. b, Enhanced binding of the Rd1 and Re chemotype to DMBT1 and the DMBT1pbs1-containing peptide DMBT1-SRCRP2. wt: wild type. c, Differential binding to *Salmonella typhimurium* wt and Rd1 of DMBT1 partially purified from two different donors. Column diagrams depict the comparison of binding efficacies of the highest DMBT1 concentrations used (40 nM). d, Schematical presentation of the exon-intron structure within the relevant region of DMBT1 with resulting RsaI restriction fragment sizes depicted below. Only the sizes of the fragments that hybridize with the probe DMBT1/sr1sid2 are depicted SR: exons coding for scavenger receptor cysteine-rich domains (red boxes); SD: exons coding for SIDs (black bars). The hypothetical configurations of the proteins are depicted below. In the carboxy-terminal part of the protein resulting from the deleted allele, it cannot be discerned between a loss of either SR9, SR10 or SR11. Only one of the possibilities is shown. e, Top panel: Southern blot analysis of the DMBT1 genomic configuration in four individuals (A-D) selected from the panel. Band sizes and exons locating on the restriction fragments are depicted at the left. Bottom panel: Western blot analysis of DMBT1 protein sizes in the partially purified and concentration-adjusted saliva samples of the four probands. The arrowhead denotes the position of the 220-kDa marker band. f, Comparison of the pathogen-binding efficacies of partially purified DMBT1 obtained from the four donors. Column diagrams depict the comparison of binding efficacies of the highest DMBT1 concentrations used (40 nM). All error bars are SEM.
Figure 4:
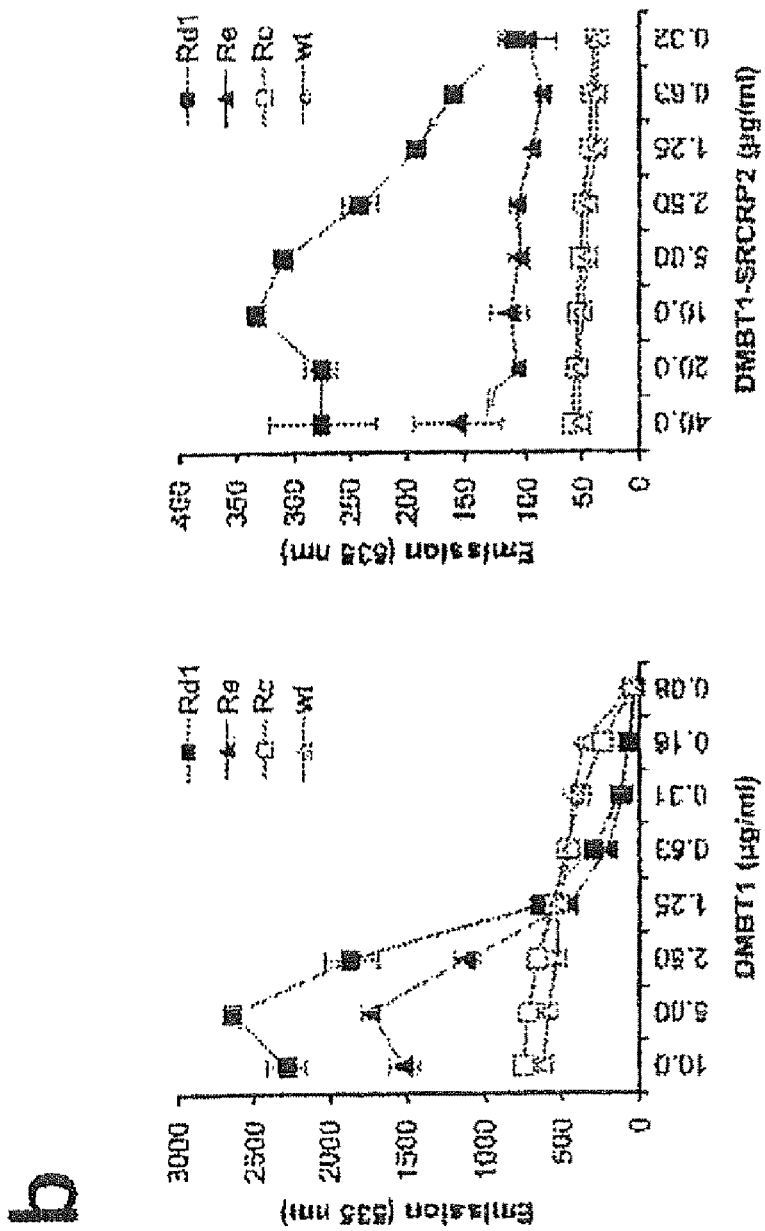
Figure 4:
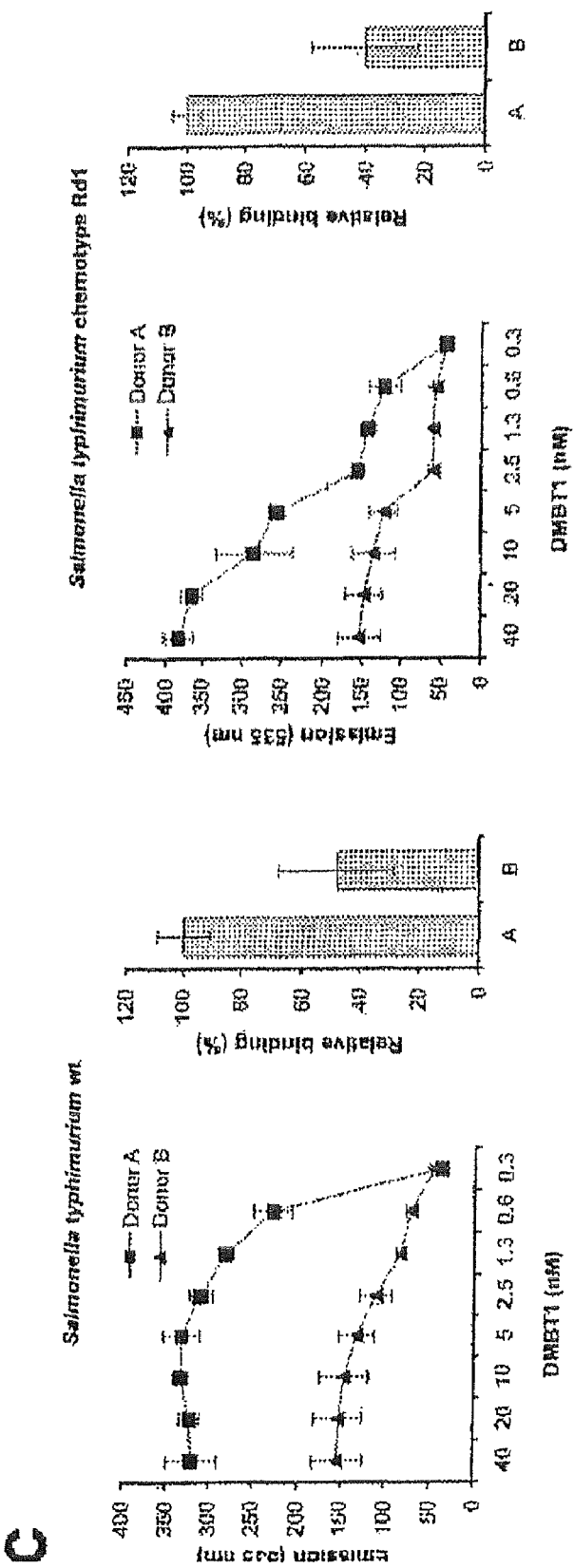
Figure 4:
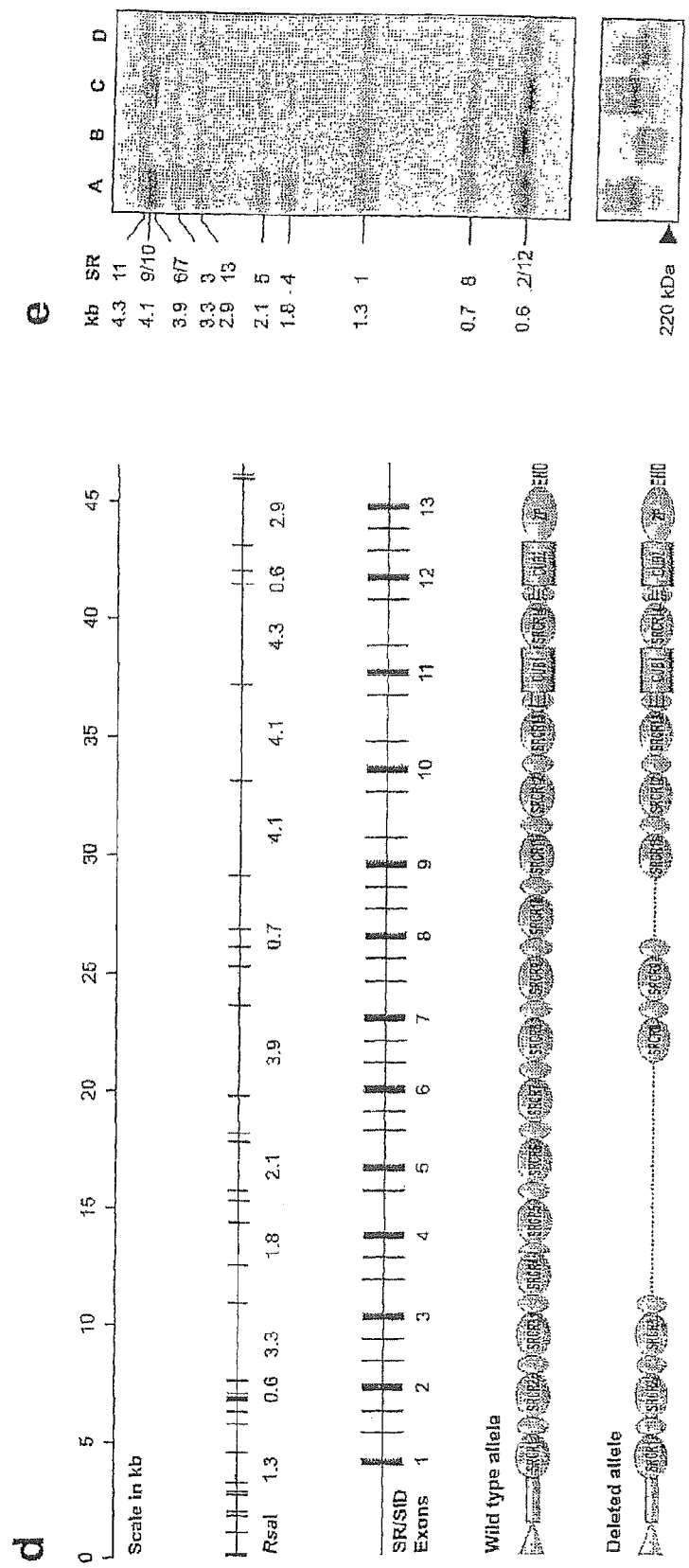
Figure 4:
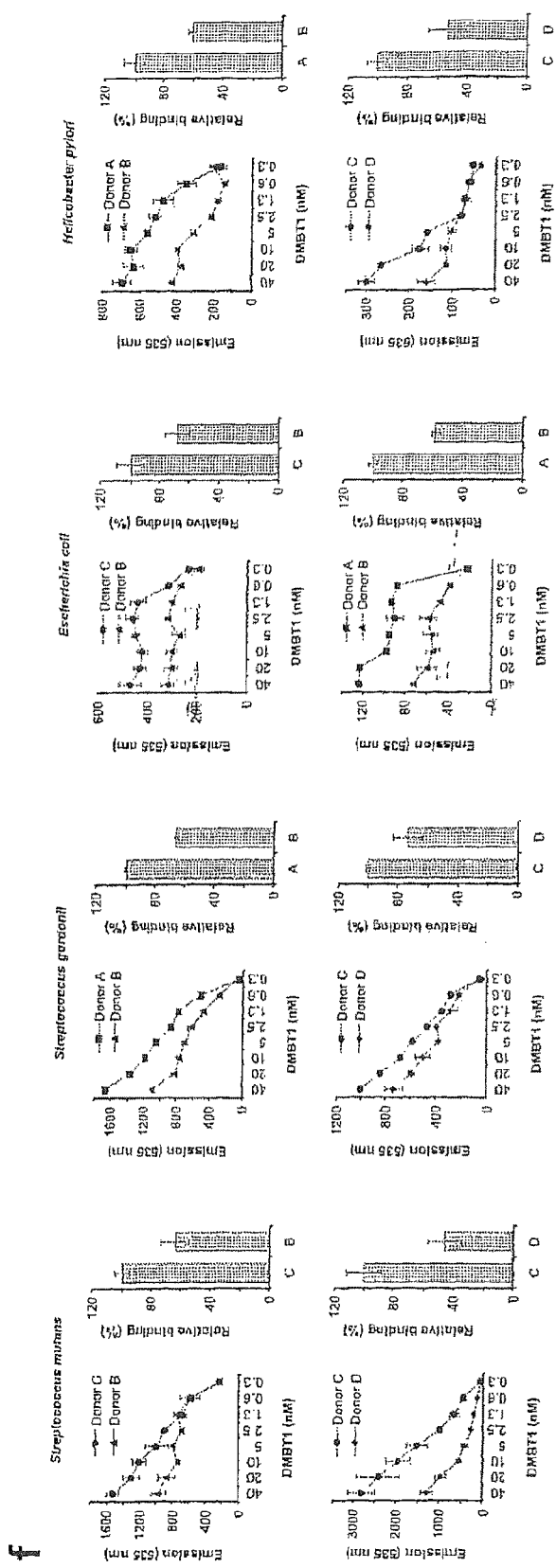

Phosphate groups are an ubiquitous and virtually invariant motif in bacterial surface structures, i.e. in lipoteichoic acid (LTA) of Gram-positive and in lipopolysaccharide (LPS) of Gram-negative bacteria. Both LTA and LPS exerted competitive effects (Table 1) and showed binding to DMBT1 (FIG. 2c,d). DMBT1 displayed stronger binding to LPS of *Salmonella minnesota* chemotype Rd1, which exposes phosphorylated carbohydrates at its surface, than to LPS of *Salmonella typhimurium* (FIG. 2c). Studies of further *Salmonella typhimurium* chemotypes clearly demonstrated that binding by DMBT1 depends on the accessability and availability of phosphorylated residues (FIG. 4a,b). We conclude that the SRCR domains of DMBT1 are fundamentally global pattern recognition domains for sulfate and phosphate groups presented in the context of both nonself (DSS, carrageenan, LPS, LTA) and self structures (DNA, phospholipids, cell surface and extracellular matrix carbohydrates).

EXAMPLE 4

Binding to Potential Targets is Less Efficient with Truncated DMBT1

Figure 5:
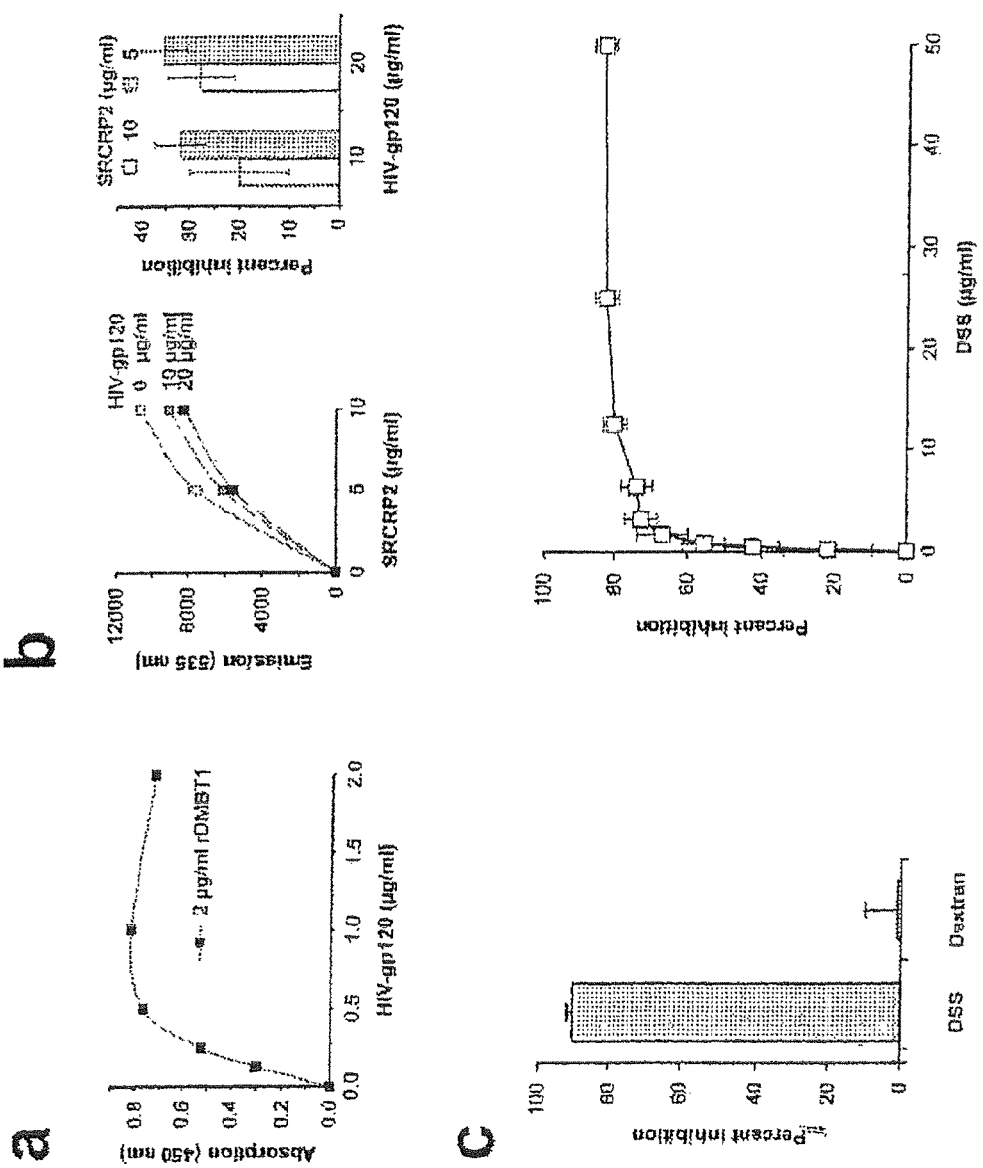
FIG. 5 DMBT1 interaction with HIV-gp120 includes pattern recognition by DMBT1pbs1. All error bars are SEM. a, Quantitative rDMBT1 (2 µg/ml) binding to recombinant HIV-gp120 immobilized on ELISA plates. b, DMBT1pbs1 exerts HIV-gp120 binding activity. Left panel: peptide SRCRP2 (containing DMBT1pbs1) was immobilized on ELISA plates and bacterial binding (*S. gordonii*) was quantified in the absence and presence of different concentrations of HIV-gp120. Right panel: mean percent inhibition from two to three independent duplicate experiments. c, Effects DSS and dextran on rDMBT1 binding to HIV-gp120. Left pal. rDMBT1 (2 µg/ml) was incubated with immobilized recombinant HIV-gp120 (1 µg/ml) in the presence of either 100 µg/ml DSS or 100 µg/ml dextran. Values are means of three independent experiments and are expressed as percent inhibition compared to incubation with rDMBT1 alone. DSS but not dextran, which lacks the sulfate groups, exerted an inhibitory effect Right panel: the same experimental setup as before except that rDMBT1 was preincubated with serial dilutions of DSS. Values are means of five independent experiments.

Partially purified DMBT1 obtained from different donors displayed remarkable differences in binding efficacies for *Salmonella typhimurium* (FIG. 4c), which, according to the previous data (FIG. 2h), was unlikely to rely on variable amounts of sIgA that might have been present in the preparations. Compared to donor A, donor B showed less binding efficacy, a decreased protein size in Western blot analyses, and genetic analyses revealed that donor A was homozygous for the DMBT1 wild type allele, while donor B was homozygous for a germline deletion eliminating 5 of the 13 (40%) pattern recognition (SRCR) domains (FIG. 4c-e). Screening of a panel of 200 normal individuals identified 2 additional carriers of the shortened allele (overall frequency 3/200 or 1.5%), of which one was available for obtaining saliva samples. Decreased DMBT1 protein size consistently correlated with the germline deletion and led to an about 30-60% decreased binding efficacy for all bacterial pathogens tested (FIG. 4e,f). DMBT1 was previously shown to interact with HIV and influenza A Virus and to inhibit viral infectivity in vitro, but recognition of HIV gp120 was proposed to rely on DMBT1-attached carbohydrates. Moreover, DMBT1 obtained from different donors displayed differential efficacies in inhibition of HIV infection in vitro. Our studies demonstrated that sulfate recognition by DMBT1pbs1 is of importance for gp120 binding and that DMBT1 germline deletions lead to a decreased gp120 binding (FIG. 5).

EXAMPLE 5

Proposed Applications and Goals for Using DMBT1 as a General Pattern Recognition Receptor for Disease-Causing Agents It is demonstrated by the present invention that the putative tumor suppressor DMBT1 is a PRR for compellingly simple molecular patterns, i.e. sulfate and phosphate groups. Although the pattern recognition site in DMBT1 differs from the one in MARCO, their ligand binding spectrum is very similar and overlaps with other PRRs that likewise interact with sulfated and phosphorylated agents. We thus consider it likely that sulfate and phosphate residues might also represent target structures for other PRRs. PRRs are multifunctional proteins playing a role in pathogen-defense and processes of normal tissue function, but how PRRs distinguish between non-self and self structures in order to not elicit undesired immune responses is an unsolved problem. For DMBT1 pattern recognition could at least provide a first common mechanistical basis that leads together its various functions. Noteworthily, also gallstones contain target sites for DMBT1 interaction, i.e. calciumphosphate, so that DMBT1's potential role in lithogenesis could rely on pattern recognition simply resembling its action in bacterial aggregation. As ECM protein, it may interact with sulfated carbohydrates such as heparansulfate, which could be of importance for its putative functions in epithelial differentiation, determination of cell polarity, wound healing, and liver regeneration. However, DMBT1 is also secreted to the mucus and to the body fluids at virtually any relevant site of pathogen-contact. Pattern recognition explains the broad pathogen-binding specificity of DMBT1 and simultaneously provides a mechanism by which it might be fixed in protective mucous layers. The latter could include interactions with surfactant phospholipids, sulfated mucins and/or surface patterns such as sulfated membrane-associated proteins. Pathogens may use sulfated structures for the attachment to target cells. Many bacteria utilize heparansulfate for attachment and HIV's gp120—also a sulfated glycoprotein—requires sulfated tyrosine residues on its co-receptor CCR5 for infection. An intriguing possibility is that the dual specificity of DMBT1 means that one of its function is to act as a general insulator. At the one hand it might bind to pathogen structures to deny their contact to target cells. On the other hand it might bind to structures on the target cells in order to mask them for the pathogens. Initial support is lent by inhibition of viral infection in vitro in the absence of accessory proteins and immune cells as well as by our in vitro experiments (FIG. 3).

Studies with Dmbt1$^{-/-}$ mice support the relevance of DMBT1-mediated protection in vivo, because the mice showed enhanced susceptibility to DSS-induced tissue damage and inflammation (Bergmann et al., submitted). Importantly, male Dmbt1$^{+/+}$ mice a priori showed 40% decreased Dmbt1 levels in the distal colon, a less efficient Dmbt1 recruitment, and a more severe susceptibility to DSS than female Dmbt1$^{+/+}$ mice. In the present report, we show that DMBT1 germline deletions in humans result in a 30-60% decreased binding efficacy for bacterial pathogens and for gp120 of HIV. We thus propose that DMBT1 germline deletions produce a leakiness within a primary defense system, which may modulate human susceptibility to infection, inflammation and, consequently, cancer types induced by pathogens that are DMBT1 ligands. *Helicobacter pylori*-induced gastritis and gastric cancer is a prime candidate, especially because similar relationships are intensely discussed for the DMBT1-related molecules MUC1 and MUC6. Beyond that, however, also impacts on disease induced by nutritional additives, e.g. carrageenans, and on liposome-mediated DNA- and drug-delivery to epithelial cells should be taken into consideration. Inclusion of DMBT1 in comprehensive epidemiological studies will be of great importance to determine the extent of its possibly broad effects on human health and disease.

EXAMPLE 6

Generating Dmbt1 Knockout Mice

Figure 6:
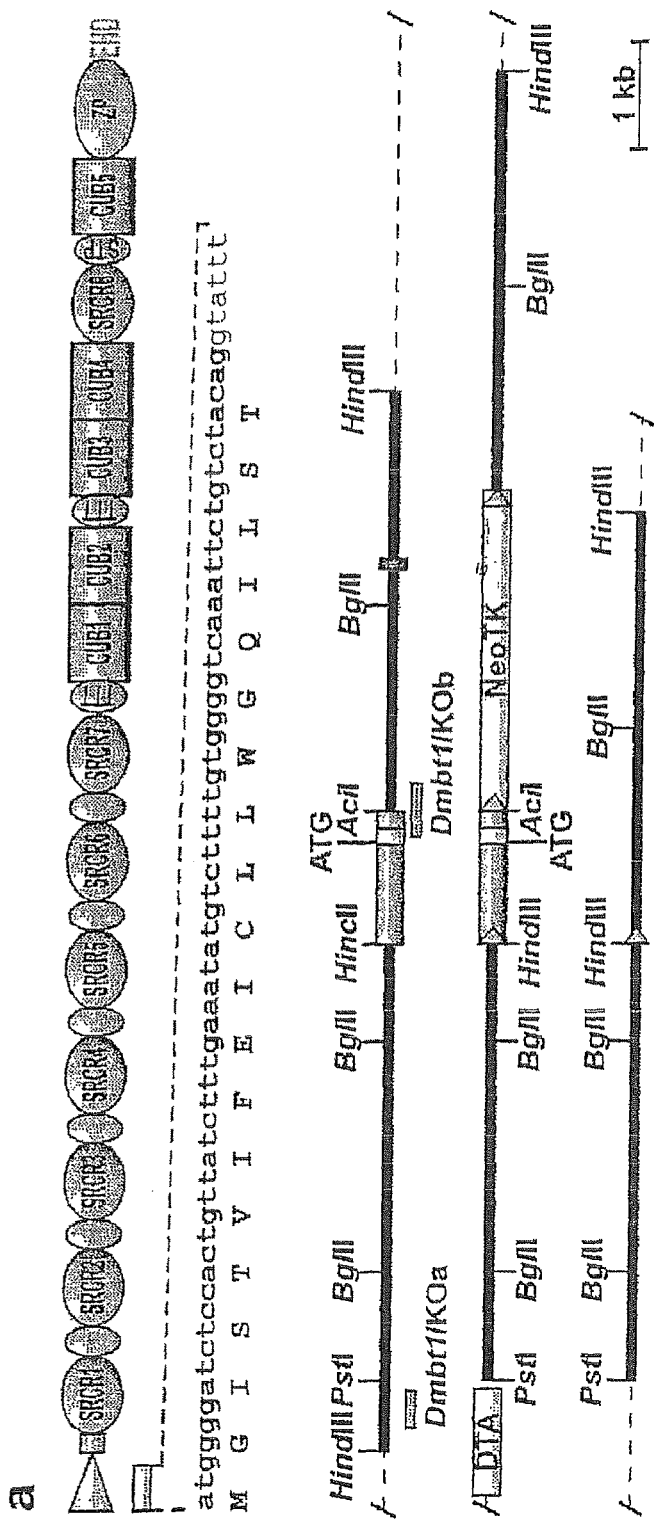
FIG. 6 Generation of Dmbt1$^{-/-}$ mice. a, Schematic presentation of the domain organization of mouse Dmbt1 (top line). The pink triangle represents the leader peptide. The pink box below denotes the part of the leader peptide encoded by exon 1 with the genomic (SEQ ID NO: 13) (bold letters: exonic sequence; normal letters: intronic sequence) and the amino acid sequence (SEQ ID NO: 14) depicted below. Blue box: small sequence without homology encoded by exon 2; SRCR: scavenger receptor cysteine-rich domain; CUB: C1r/C1s-Uegf-Bmp1 domain; ZP: *zona pellucida* domain; EHD: Ebnerin-homologous domain. Orange ovals indicate SRCR interspersed domains (SIDs); TTT and STP are threonine and serine-threonine-proline-rich domains, respectively. Following lines: schematical presentation of the wild type allele as contained in genomic subclone Dmbac1c1, the targeting construct, and the knockout allele after Cre-mediated recombination. Red box: targeted 1224-bp region containing exon 1 (pink box) as well as about 900 bp of the promoter region; blue box: exon 2; yellow boxes: selection cassettes; yellow triangles: LoxP sites; gray boxes: probes used for the identification of ES-cells with homologous recombination (Dmbt1/KOa) and for the identification of ES cells and mice carrying the knockout allele (Dmbt1/KOb). b, Southern blot analysis of mouse genomic DNA with probe Dmbt1/KOb demonstrated the wild type 4.1-kb BglII fragment in Dmbt1$^{+/+}$ mice, while Dmbt1$^{-/-}$ displayed the deleted 2.9-kb BglII fragment, and Dmbt1$^{+/-}$ mice were heterozygous for the two alleles. c, Northern blot analysis of small intestine RNA with probe DMBT1/8 kb-3.8 (top panel) and a β-actin probe (bottom panel). The expected size of the Dmbt1 transcript is 6.6 kb. d, Western blot analysis of protein extracts from mouse small intestines with polyclonal anti-DIVIBT1$^{GP340}$ (upper panel) and anti-DMBT1$^{SAG}$ (lower panel). Arrowheads mark the position of the 210-kDa marker band. e, RNA in situ hybridization and f, immunohistochemical analysis (anti-DMBT1$^{SAG}$) of distal duodenum sections of Dmbt1$^{+/+}$ and Dmbt1$^{-/-}$ mice.
Figure 6:
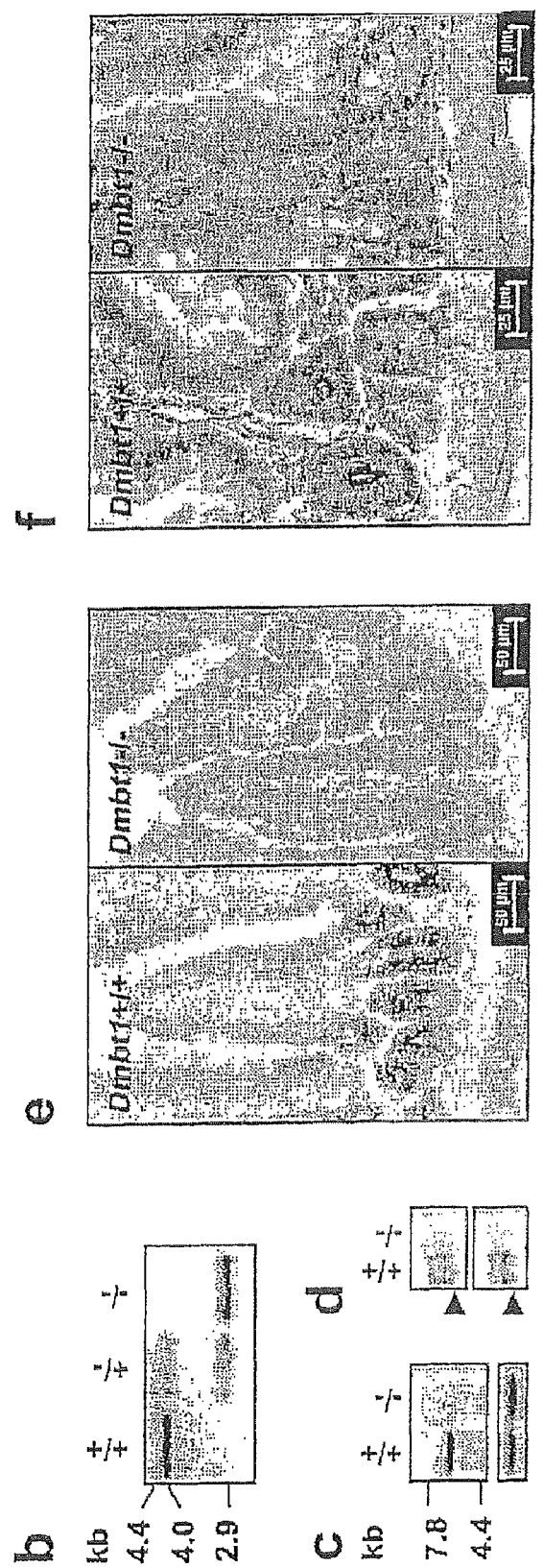

In order to investigate the DMBT1 functions in vivo, we generated mice homozygously deficient for Dmbt1 (also known as Crp-ductin) by targeting a genomic 1224-bp HincII/AciI fragment. It comprised parts of the promoter, the 5'-utr, and exon 1, which contains the start codon and the coding sequence for major parts of the signal peptide required for secretion (FIG. 6a). Analysis of mouse genomic DNA corded the predicted BglII fragments of 4.1 kb and 2.9 kb for the wild type and the knockout allele, respectively (FIG. 6b). Absence of the corresponding transcript and protein from the small intestine of Dmbt1$^{-/-}$ mice confirmed the functional inactivation of Dmbt1 (FIG. 6c-f). Dmbt1$^{+/-}$ and Dmbt1$^{-/-}$ mice were viable and macroscopical and histological inspection of major organs at the age of 8 and 22 weeks did not reveal obvious differences compared to Dmbt1$^{+/+}$ mice (n=3 per group and time point).

EXAMPLE 7

Expression Pattern of DMBT1

Figure 7:
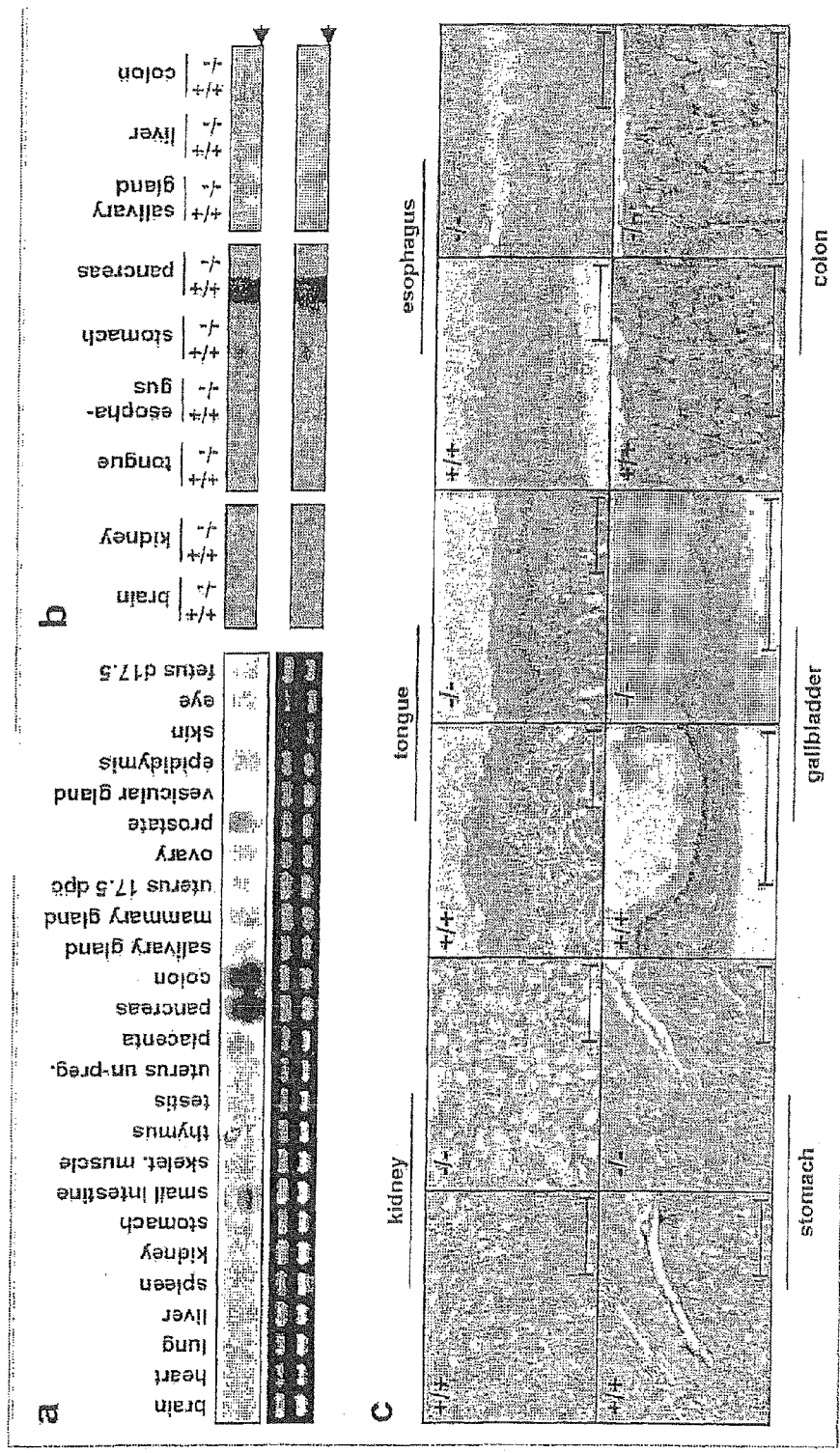
FIG. 7 Expression analyses in mouse tissues. a, Exemplary results from Northern blot analyses (upper panel; probe: DMBT1/hfl2-2.1). For size comparison refer to the 6.6-kb transcript of the small intestine. All three hybridization probes that were used (see methods section) produced identical results. The 28S and 18S bands of the corresponding RNA gels are shown in the panel below. b, Western blot analysis of Dmbt1$^{+/+}$ and Dmbt1$^{-/-}$ mouse tissues with anti-DMBT1$^{GP340}$ (top panel) and anti-DMBT1SAG (bottom panel). Arrowheads indicate the position of the 220-kDa marker bands; Note that the left panel shows results from a ten-fold longer exposure than the middle and right panel. c, Exemplary results from immunohistochemical studies with anti-DMBT1$^{SAG}$ in adult tissues of Dmbt1$^{+/+}$ and Dmbt1$^{-/-}$ mice. Scale bars represent 100 µm. Dmbt1 expression was not detectable by any of the methods in tissues with multilayered epithelia, such as skin, esophagus, and tongue. The kidney and 17.5 day-old mouse fetuses showed faint signals with only one of the four methods used (Western and Northern blotting, respectively) suggesting low expression levels close to the detection limits of the methods. Note the luminal secretion by the monolayered epithelia of the cardiac portion of the glandular stomach, the gallbladder, and the colon, which resembles the mode of secretion of human DMBT1 in the respective tissues.

Previous studies linked DMBT1 to possible functions in triggering differentiation in kidney, adult multilayered and fetal epithelia Analyses by immunohistochemistry, RNA in situ hybridization Northern and Western blotting demonstrated that these tissues showed poor or no Dmbt1 expression in mice (FIG. 7 and not shown). By human adult monolayered epithelia and glands DMBT1 is secreted to the mucous layer and/or to body fluids. The expression pattern of Dmbt1 was well conserved in gastrointestinal tract tissues with monolayered epithelia, such as the stomach, small intestine, colon, and gallbladder (FIG. 6c-f, FIG. 7a-c and not shown). Immunohistochemical analyses demonstrated luminal Dmbt1 secretion to the mucous layer as observed for human DMBT1 (FIG. 7c). We thus concluded that DMBT1 functions in humans and mice are likely to be conserved in the gastrointestinal tract.

EXAMPLE 8

Susceptibility of DMBT1-Knockout and Wild Tripe Mice to Sulfate Group Exposing Disease Causing Agents Because we hypothesized that DMBT1 is part of the protective mucous layer, which is of importance for defense against infection-, inflammation- and cancer-inducing pathogenic stimuli, we challenged the mice with dextran sulfate sodium (DSS). DSS induces tissue damage, acute/chronic colitis, and finally colorectal carcinomas and therefore is also a model for damage- and inflammation-induced cancer. Its structural analogue, carrageenan, is widely used as thickener, stabilizer, and texturizer in human food and is suspected to cause ulcers, inflammation, and colorectal cancer. We first treated the mice for seven days with 5.0% DSS. To confirm and extend the data, we initially intended a treatment with 2.5% DSS for 10 days. For reasons depicted below we reduced 2.5% DSS-treatment to eight days followed by two days of recovery during the course of the experiment (FIG. 8a).

Figure 8:
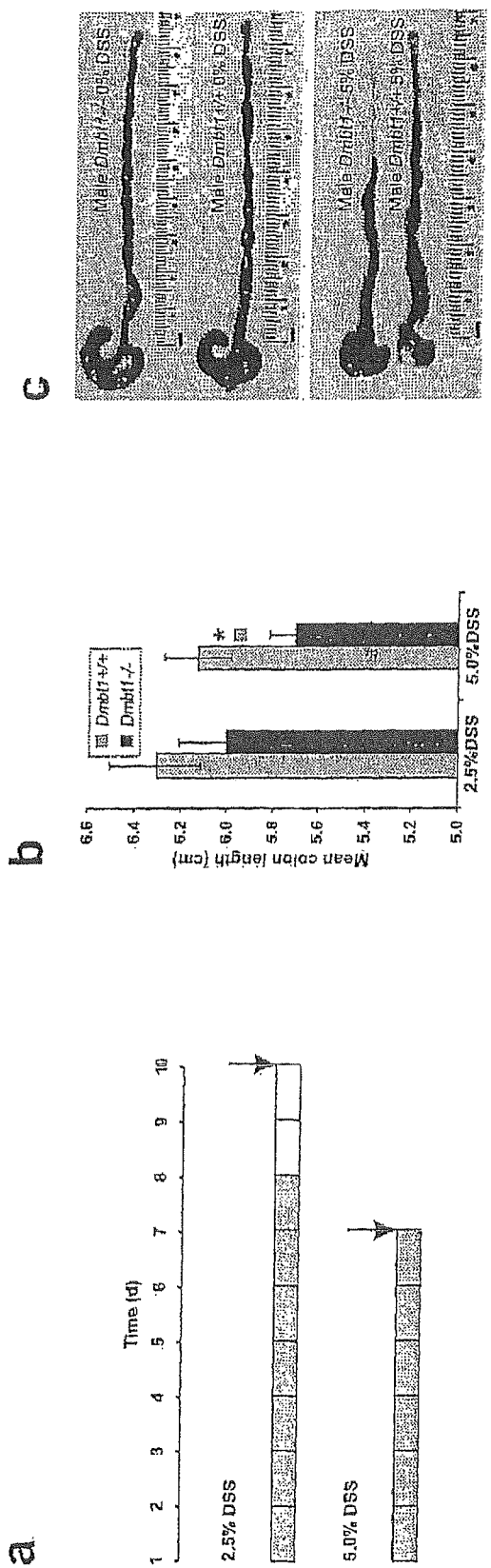
FIG. 8 Deficient protection of Dmbt1$^{-/-}$ mice against tissue damage and inflammation. a, Treatment schemes for the 2.5% DSS (top) and the 5.0% DSS (bottom) experiment Gray boxes: DSS-administration; white boxes: normal drinking water without DSS; arrows: time point of analysis. Animal numbers are given in the methods section. b, Mean colon lengths after DSS-treatment. c, Exemplary images of the mouse colon without (0.0% DSS) and after (5.0% DSS) DSS-treatment, respectively. d, Body weight losses upon DSS-treatment. Administration of 2.5% DSS led to significantly increased body weight losses in Dmbt1$^{-/-}$ mice. Comparison of the relative weight losses (right panel) suggested that dose increase to 5.0% DSS overcame Dmbt1-mediated protection in vivo and resulted in saturation effects. e, Mean percentage of mucosal area affected by damage and inflammation in the distal colon. f, Mean histopathological (HP) scores in the distal colon. ES: epithelial damage score; IS: inflammation score; GS: granulocyte score; LS: lymphocyte score. g, Comparison of mean combined damage scores of distal (DI) and proximal (PR) coli in the two experiments. DSS-treatment specifically produced significant differences in the distal colon. Significantly enhanced scores in the proximal coli of the 5.0% DSS experiment were consistent with the experimental design shown in FIG. 8*a*. The time lag with which the DSS reaches the distal part explains why increased scores are observed at 2.5% DSS, although 5.0% DSS produced more severe weight losses ($P \leq 0.0001$ for both genotypes). All error bars are standard errors of the mean (SEM). Statistical significant results are indicated by (*) for $P \leq 0.05$, () for $P \leq 0.01$, (*) for $P \leq 0.001$, and (****) for $P \leq 0.0001$, followed by the symbol/color code for the respective group under comparison.
Figure 8:
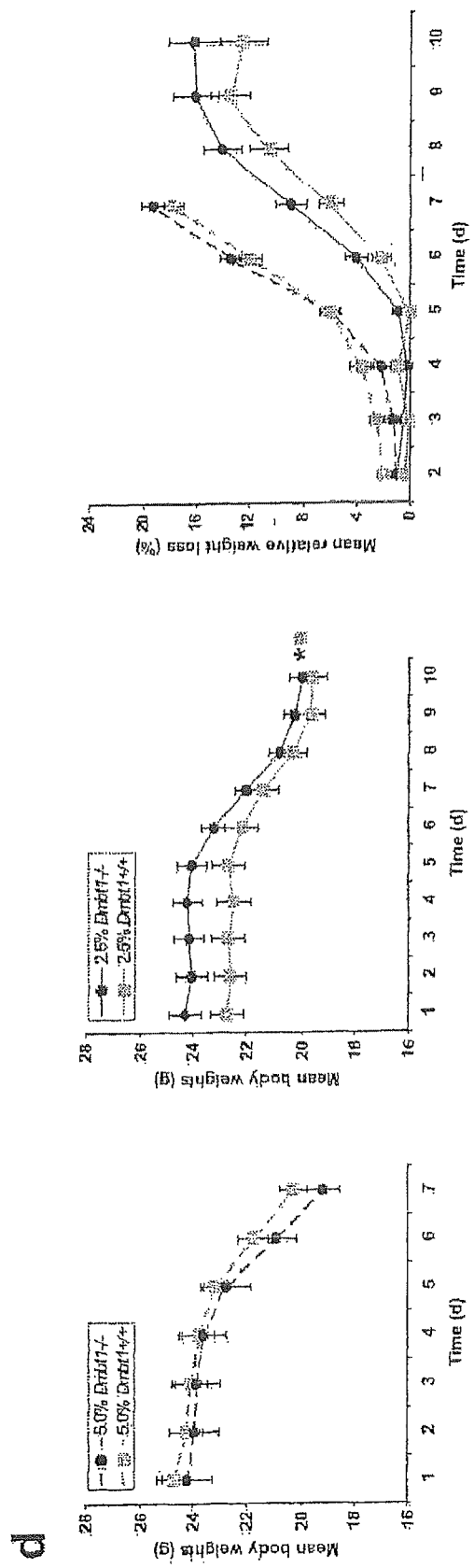
Figure 8:
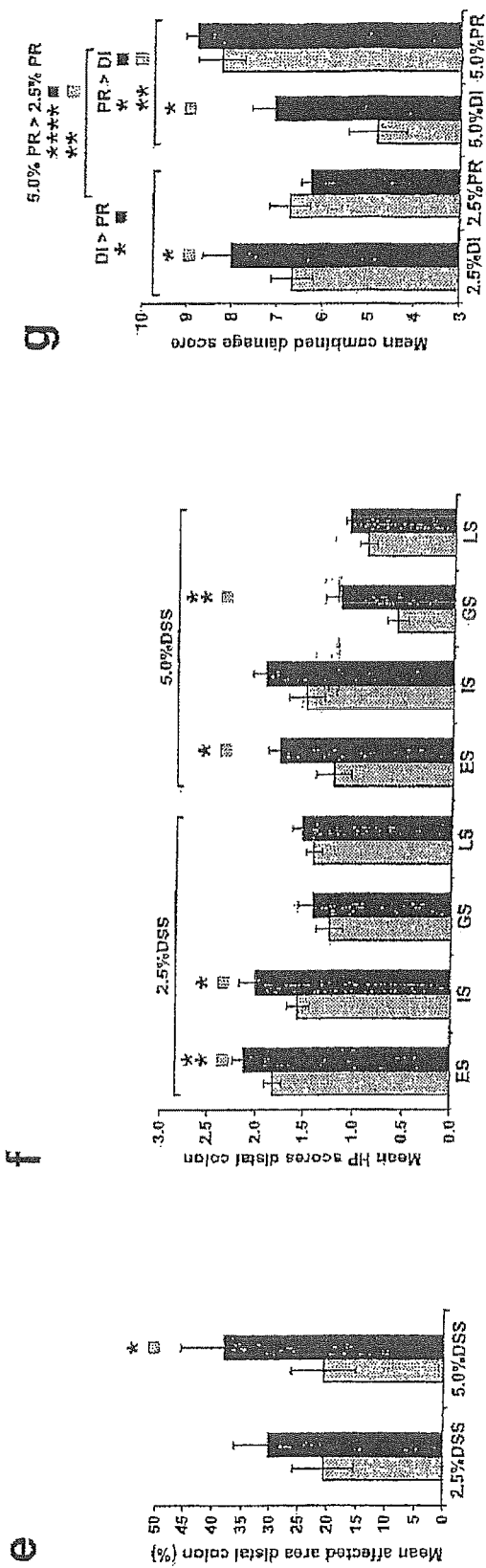

Dmbt1$^{-/-}$ mice were more severely affected by tissue damage, inflammation, and macroscopic symptoms (weight. loss, colon length reduction) with various parameters reaching statistical significance (FIG. 8b-g). Reduction of differences between body weight losses by dose increase to 5.0% DSS (FIG. 8d) pointed to a possible stoichiometric component. Significant differences were obtained for the distal but not for the proximal colon (FIG. 8g). Setting the time point of analysis during the course of treatment (5.0% DSS) produced higher scores in the proximal than in the distal colon. In contrast, after two days of recovery (2.5% DSS) higher scores were obtained for the distal than for the proximal colon (FIG. 8g). This pointed to spatiotemporal effects, which are in accordance with the chronological order of DSS passage through the colon.

Figure 9:
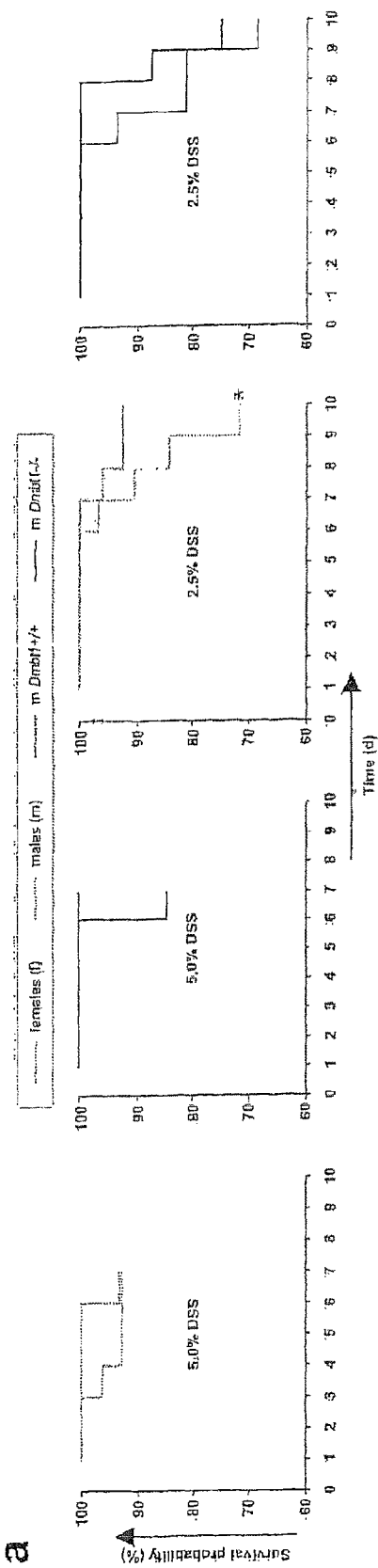
FIG. 9 General gender differences in protection against DSS-induced tissue damage and inflammation. a, Kaplan-Meier plots of survival probabilities in the relevant groups. A significantly enhanced male mortality was observed only during the prolonged observation interval of the 2.5% DSS experiment with no significant differences between Dmbt1$^{-/-}$ and Dmbt1$^{+/+}$ males. b, Male weight losses were significantly enhanced in both experiments, but differences compared to females were more pronounced at 2.5% DSS as also indicated by the plot of the relative weight losses (right panel). c, Colon lengths. Improved female protection is supported by a correspondingly less colon length reduction at 2.5% DSS. d-f, Histopathological scores. Enhanced male susceptibility to DSS challenge was not reflected by corresponding significant differences at the level of histopathological changes, which is in accordance with two previous studies, using lower[26] or higher[27] animal numbers. All error bars are standard errors of the mean (SEM). Abbreviations and symbols that indicate statistical significance were chosen in accordance to FIG. 8.
Figure 9:
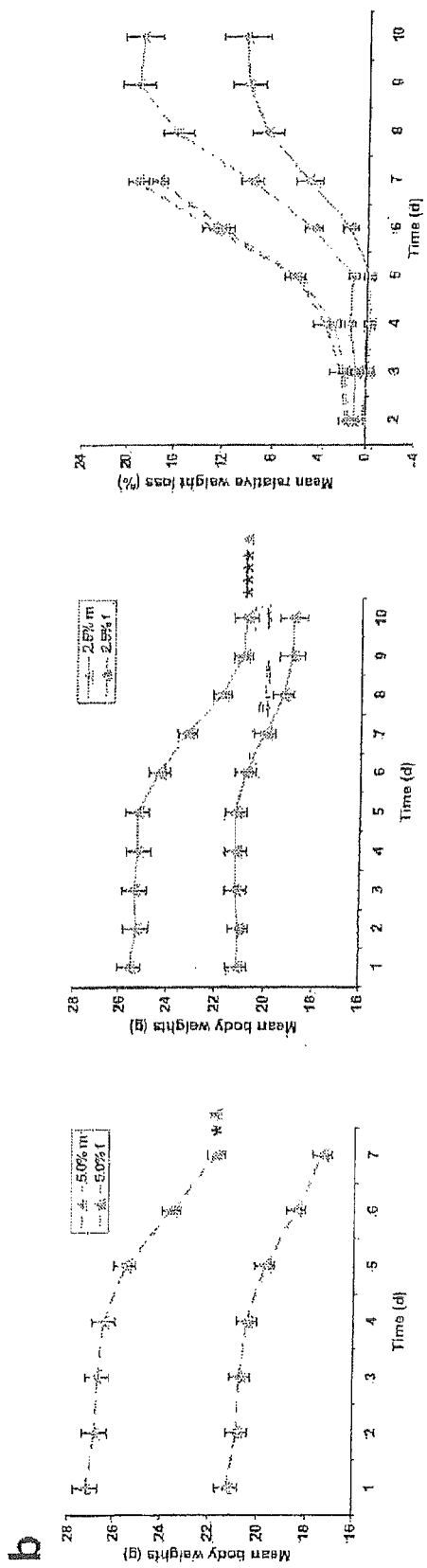
Figure 9:
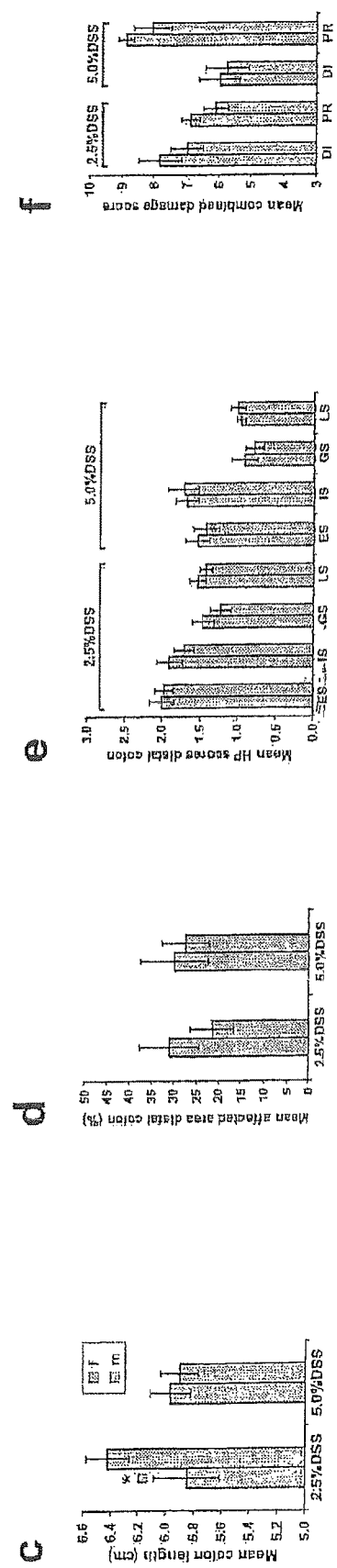

At day 8 of the treatment with 2.5% DSS, we noted an increased mortality of male mice, which continued despite of DSS substitution by normal drinking water (FIG. 8a). Analyses of survival probabilities pointed to an overall enhanced male susceptibility to DSS (FIG. 9a). Support was lent by correspondingly increased male weight loss and colon length reduction (FIG. 9b,c), but no correlating significant differences were observed at the level of histopathological changes (FIG. 9d-f). This resembled the results of; to our knowledge, the only two previous studies that discriminated between effects on males and females in the DSS-model.

Figure 10:
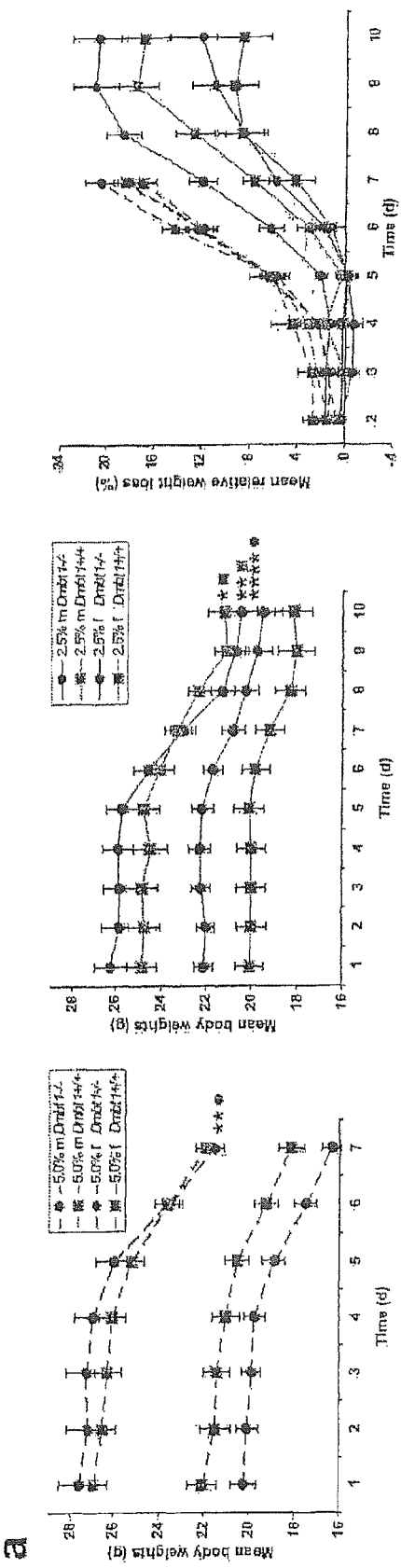
FIG. 10 Dmbt1$^{-/-}$ specific gender differences in protection against DSS-induced tissue damage and inflammation. a, Plots of weight losses in Dmbt1$^{-/-}$ and Dmbt1$^{+/+}$ mice broken down to gender. The distribution of significant differences between the absolute body weight curves (left and middle panel) pointed to complex relationships, which are easier accessible when considering the plots of the relative body weight losses (right panel). Compared to Dmbt1$^{+/+}$ females, Dmbt1$^{+/+}$ males showed significantly enhanced weight losses at 2.5% DSS (middle panel) supporting pre-existing gender differences in the susceptibility to DSS[26,27]. Compared to the respective age- and gender-matched wild type littermates, Dmbt1 g males but not Dmbt1$^{-/-}$ females showed significantly increased weight losses. Consequently, the gap between males and females became greater, as indicated by a P-value of $\leq 0.0001$ (middle panel) and the increase of the gap between the curves in the right panel. Dose increase to 5.0% DSS eliminated most differences except for the most prominent one between Dmbt1$^{-/-}$ males and females (P$\leq$0.01; left and right panel). The data demonstrated that differences in male gender provided the major contribution to the weight loss differences between genotypes. b, Colon lengths. Similar trends were reflected at the level of this parameter, but did not reach statistical significance after correction for multiple testing. c-e, Histopathological analyses in Dmbt1$^{-/-}$ and Dmbt1$^{+/+}$ mice broken down to gender. Statistical significant differences (P-values corrected for multiple testing) were observed for female but not for male mice. The fact that differences between Dmbt1$^{-/-}$ and Dmbt1$^{+/+}$ mice were more pronounced in female than in male gender demonstrated that females provided the major contribution to the genotype differences in histopathological scores. The numerical values indicated that this image probably emerged, because the scores reached saturation for most parameters in all groups except for the female Dmbt1$^{+/+}$ mice, which showed less severe histopathological changes. Note that female knockout mice approached the levels obtained for male mice, but did not show this property in regard to weight losses. All error bars are standard errors of the mean (SEM). Abbreviations and symbols that indicate statistical significance, were chosen in accordance to FIG. 8.
Figure 10:

Subgroup analyses demonstrated that differences between female mice provided the major contribution to differences in histopathological changes between Dmbt1$^{-/-}$ and Dmbt1$^{+/+}$ mice. In contrast, the major contribution to differences in weight losses and colon length reductions came from male Dmbt1$^{-/-}$ mice (FIG. 10a-e). In conclusion, only considering genotype differences represents an inappropriate simplification. The degree of susceptibility to DSS is male Dmbt1$^{-/-}$>male Dmbt1$^{+/+}$>female Dmbt1$^{-/-}$/>female Dmbt1$^{+/+}$ mice. In this order also the staggered onset of histopathological changes and, consequently, saturation effects would occur, i.e. earliest in male Dmbt1-1 and latest in female Dmbt1$^{+/+}$ mice, which is compatible with the data (FIG. 10c-e). The major contribution of female Dmbt1$^{-/-}$ mice to the histopathological scores is caused by the less severe changes in wild type females, which is based on an improved female protection against DSS (FIG. 9b-f and FIG. 10a-e).

Figure 11:
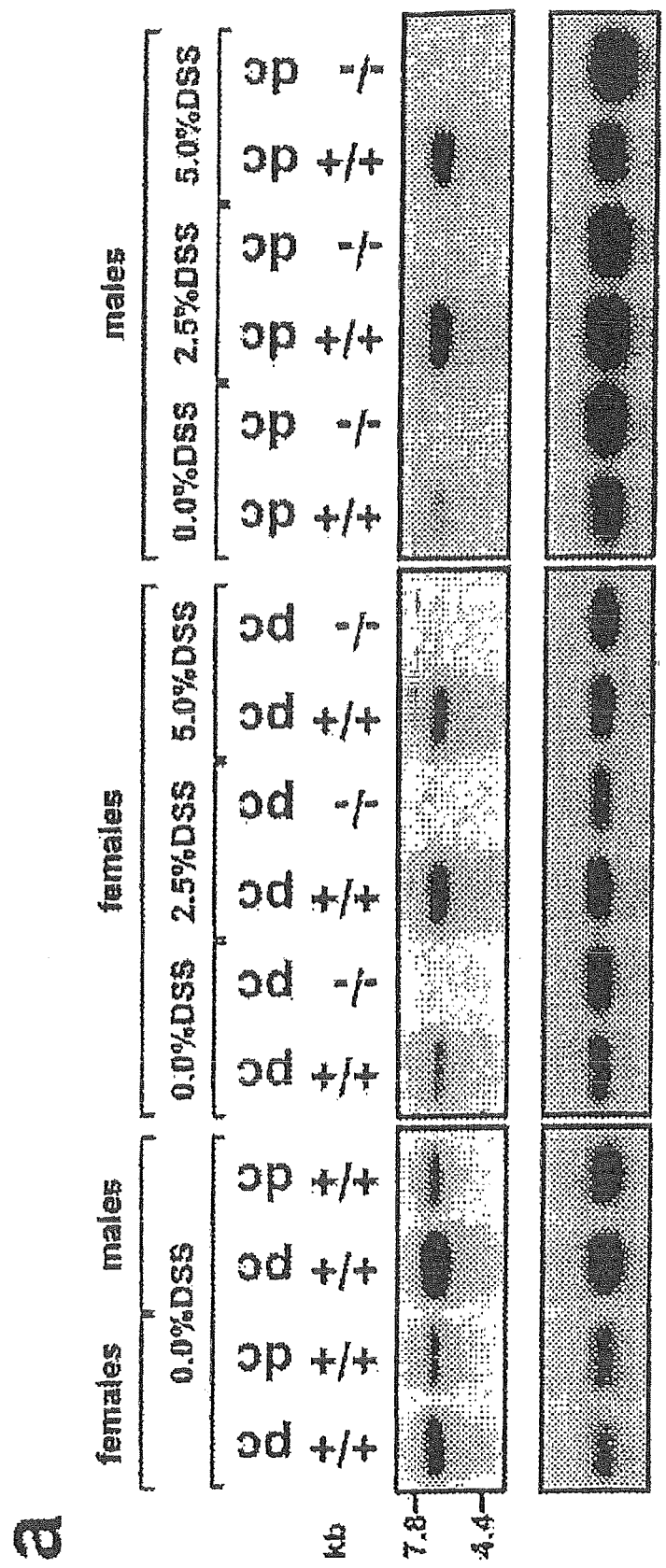
FIG. 11 Dmbt1 expression in the colon and direct interaction with DSS and carrageenan. a, Northern blot analyses of pooled total RNA (n=3) with probe DMBT1/8 kb-3.8 (top panels) and a β-actin probe (bottom panels). pc: proximal colon; dc: distal colon. Left panel: direct comparison of the Dmbt1 expression levels in the coli of age-matched untreated (0.0% DSS) Dmbt1$^{+/+}$ mice. Middle and right panel: exemplary results from proximal and distal coli of female and male mice, respectively, treated with 0.0%, 2.5%, or 5.0% DSS. b, Quantitative analysis of Dmbt1 expression levels in the colon of untreated mice. The ratio of Dmbt1:β-actin was determined from two independent Northern blot experiments. Error bars are SEM. The proximal colon shows higher Dmbt1 expression levels than the distal colon, resembling the expression levels in the human colon[13]. Compared to females, males on average showed about 14% reduced expression levels in the proximal colon (pc) and an about 40% reduction in the distal colon (dc). c, Quantitative analysis of Dmbt1 expression after DSS challenge. The Dmbt1:β-actin ratios are expressed as percent referred to the respective age-, gender-, and tissue-matched untreated (0.0% DSS) samples. Dmbt1 expression consistently was upregulated in a dose-dependent manner. The enhanced induction in the female proximal colon after treatment with 2.5% DSS resulted from one animal that displayed a very strong response as revealed by analyses of unpooled tissues. In all other cases, the animals showed equivalent responses. Note also that DSS-induced damage leads to a depletion of colon epithelial cells by crypt losses and ulcers, so that the increase of Dmbt1 expression is underestimated. d, Direct comparison of the Dmbt1 expression levels in the different groups. For the calculation of the adjusted ratios see methods section. The data point to a maximal transcriptional mobilization of Dmbt1 in all groups when 5.0% DSS is used. e, Inhibitory effects of DSS on human recombinant DMBT1 (rDMBT1) mediated *Streptococcus gordonii* aggregation. f, Inhibitory effects of DSS on bacterial aggregation mediated by the synthetic peptide DMBT1-SR-CRP2, which comprises the DMBT1 pathogen binding site[17]. g. Inhibitory effects of degraded lambda carrageenan (LC) on human rDMBT1-mediated bacterial aggregation. h, Inhibitory effects of degraded lambda carrageenan on bacterial aggregation mediated by DMBT1-SRCRP2. i, Binding of human rDMBT1 to immobilized DSS. j, Binding of human rDMBT1 to immobilized degraded lambda carrageenan. Error bars represent SEM. rDMBT1 binding was detected using a monoclonal antibody. rDMBT1+: 10 μg/ml recombinant DMBT1; rDMBT1−: negative control without addition of rDMBT1.
Figure 11:
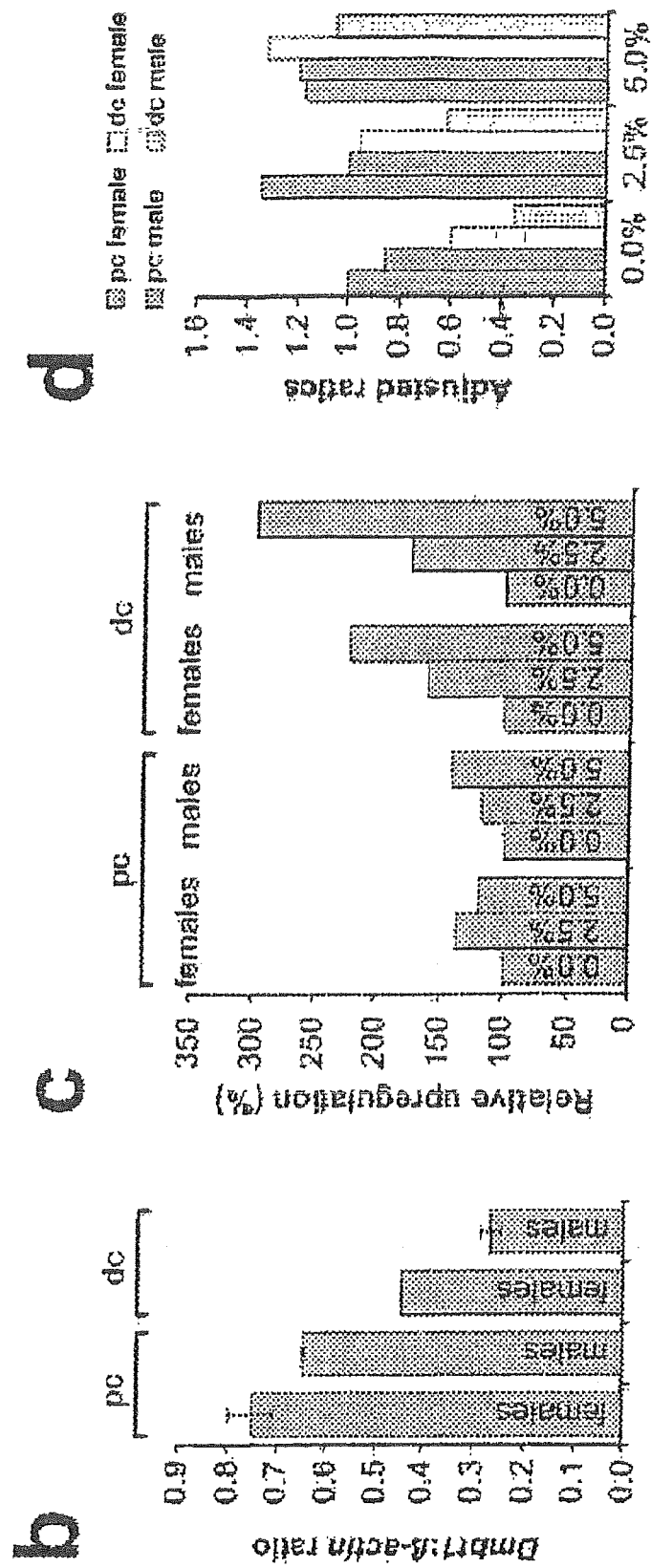
Figure 11:
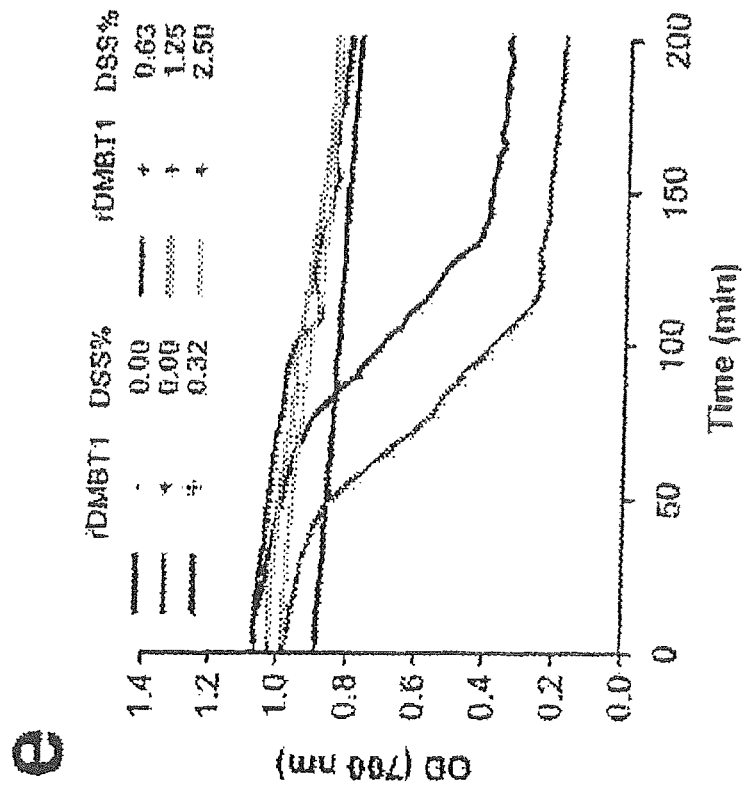
Figure 11:
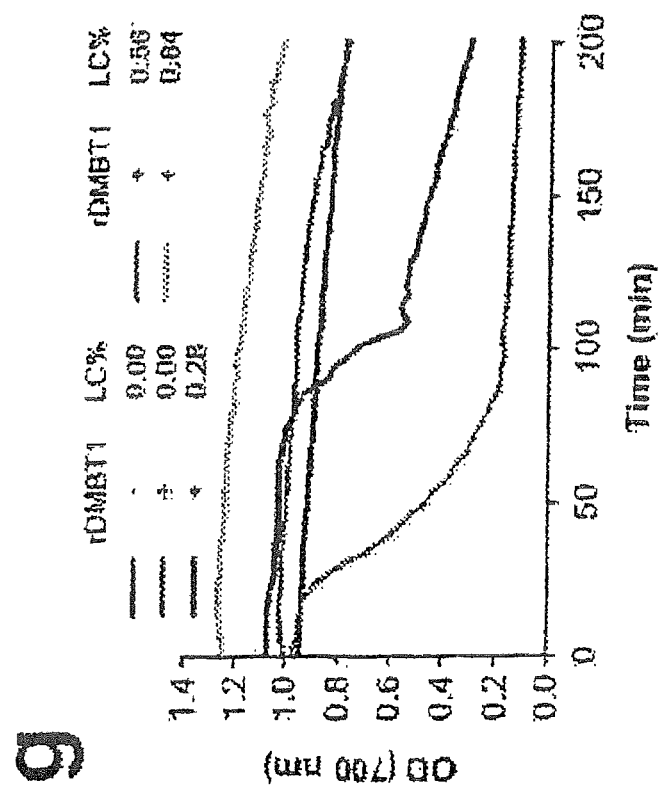
Figure 11:

Compared to females, male wild type mice showed reduced Dmbt1 expression levels in the proximal and distal colon (average reduction: 14% and 40%, respectively) in the unchallenged state (FIG. 11a,b) and the differences were still prevalent after challenge with 2.5% DSS (FIG. 11c,d). We conclude that differences in Dmbt1 levels could contribute to the gender differences in DSS susceptibility, but that other factors may also play a role. Otherwise female and male Dmbt1-1 mice would be expected to show equal relative weight losses. Because the gap reproducibly even increased at the level of this dynamic and therefore more sensitive parameter (FIG. 10a), we further conclude that Dmbt1 inactivation is more critical for male gender.

Consistently, DSS challenge led to a dose-dependent upregulation of Dmbt1 expression levels (FIG. 11a,c), which appeared to reach maximum values in each group when using 5.0% DSS (FIG. 11d). These data together with the equalization of weight losses upon dose increase to 5.0% DSS and the luminal localization of the protein raised the possibility that Dmbt1/DMBT1 might directly interact with pathogenic agents such as DSS and thereby exerts its protective effects. Mouse and human DMBT1 are functionally equivalent in regard to their interaction with some bacterial pathogens. Competition and binding studies in vitro demonstrated that human DMBT1 directly interacted with both DSS and the structurally related carrageenan via its recently identified binding site for bacterial pathogens (FIG. 11e-j). Together with the previous results these data strongly suggest that the number of available DMBT1 binding sites in relation to the pathogen dose is crucial for protection and that our in vivo data can be projected from pathogenic sulfated polysaccharides to bacterial pathogens.

EXAMPLE 9

Proposed Implications for DMBT1's Role in Defense Against Disease Causing Agents In summary, we report on the generation and analysis of Dmbt1 knockout mice and demonstrate that Dmbt1 mediates protection against tissue damage and acute inflammation in vivo. The situation can be projected to humans, because mouse and human DMBT1 show the same expression patterns and modes of secretion in the gastrointestinal tract Furthermore, human DMBT1 interacts not only with DSS, as was predictable from the animal experiments, but also with carrageenan. Both agents represent paradigms for substances leading. to the development of colorectal cancer via tissue damage and inflammation. As food compound, carrageenan is of specific relevance for human health and disease. Functional equivalence of mouse, and human DMBT1 in regard to their. binding properties is supported by recent studies (Bicker et al., submitted). DSS and carrageenan interaction involves the DMBT1 binding site for bacterial pathogens. In a parallel study, we identify DMBT1 as a pattern recognition receptor for both sulfate and phosphate residues present in DSS/carageenan and in bacterial cell wall components, respectively (Biker et al., submitted). This lends further support for our assumption that the present in vivo data can be projected to DMBT1's role in defense against bacterial pathogens. In the afore-mentioned study, we also demonstrate that DMBT1 germline deletions in humans, which reduce the number of pathogen binding sites by 40%, result in a correspondingly decreased scavenging activity, e.g. for *Helicobacter pylori* (Bier et al., submitted). The 40% reduction of Dmbt1 expression levels in the distal colon of male mice results in a comparable situation and may contribute to enhanced male DSS susceptibility. Moreover, Dmbt1 inactivation had a more pronounced effect in male mice. Thus, DMBT1 could represent a factor that contributes to the male preponderance among the ulcerative colitis patients suggested by many studies. Ulcerative colitis is associated with an increased risk for colorectal cancer. Therefore, DMBT1 could provide a link between the emergence of complex diseases (infection, inflammation, cancer), gender effects, nutritional (carrageenan) and genetic factors (DMBT1 germline deletions). Taken together, we propose DMBT1 as a protective factor, whose impaired function is predicted to have an impact for susceptibility to infection, tissue damage, inflammation, and, consequently, also the downstream development of cancer. Rather than studies of loss of heterozygosity and mutations in cancer cells comprehensive analyses of DMBT1 polymorphism are required to elucidate its role in environmentally induced diseases including certain cancer types.

1. Materials and Methods (Referring to Examples 1 to 5)
Synthetic Peptides.

Synthetic peptides were obtained from Eurogentec, Belgium (purity at least 85%). The peptides were dissolved in DMSO, diluted 1:10 in $H_2O_{bidest}$ in order to obtain stock solutions of 1 mg/ml in 10% DMSO, aliquoted, and stored at −20° C. until use.
Purification of Salivary DMBT1.

Salivary DMBT1 (salivary agglutinin; DMBT1$^{SAG}$; hereafter referred to as DMBT1) was obtained from parotid saliva of healthy volunteer donors collected with Lashley cups. For confirmatory experiments of DMBT1 interaction partners, initial studies with *Salmonella* strains, and HIV studies we used DMBT1 purified to about 95% homogeneity by the procedure described before. The concentration was determined by the BCA Protein Assay Kit (Pierce) according to the instructions of the manufacturer. For interindividual comparisons, we used partially purified DMBT1, because co-precipitating sIgA did not affect pathogen-interactions (FIG. 2h). For partial purification, 50 ml parotid saliva was incubated for 0.5 to 1 h in ice water, in order to promote the formation of a precipitate. After centrifugation for 20 min (4° C.; 5,000 g), the pellet was resuspended in 1.0 to 2.5 ml PBS. In order to determine the DMBT1 concentrations within the samples, serial dilutions of the preparations were compared to serial dilutions of purified recombinant DMBT1 (rDMBT1) by ELISA and the adjusted concentrations were confirmed by Western blotting (see below).
Expression and Purification of Recombinant DMBT1.

Detailed protocols on molecular cloning, the generation of stably transfected cell lines and the purification of human recombinant DMBT1 (rDMBT1) will be published elsewhere (End et al., in preparation) or are available from the authors upon request. Briefly, the largest known DMBT1 open reading frame corresponding to the DMBT1/8 kb.2 variant (EMBL Accession no. AJ243212) was cloned into the pT-REx-DEST30 vector (Invitrogen) under the control of a tetracycline-inducible promoter. The plasmid was transfected into the cell line T-REx-CHO (Invitrogen), which constitutively expresses the Tet-repressor protein, using Fugene 6 (Roche Diagnostics). Stable transfectands were selected by addition of 1 mg/ml G418 and 0.001 mg/ml blasticidin. Subcloning was done by low-density plating (20 cells per 50 cm$^2$) and picking of single colonies after 15 d under selection pressure. Clone CHO-DMBT1/8 kb.2-T3 displayed highest expression levels upon induction with 10 µg/ml tetracycline for 48 h and predicted transcript and protein size in Northern blot and Western blot analyses using probe DMBT1/8 kb-3.8 and the monoclonal antibody anti-DMBT1h12 under the conditions descried before. For the production of rDMBT1, cells were grown in DMEM/F12 with 10 µg/ml tetracycline for 48 h, the supernatants were collected, diluted 1:3 in buffer A (20 mM Tris-HCl; 10 mM EDTA, pH 8.0), and filtered by 0.22 µm bottle top filters prior to loading on an 1 ml anionexchanger column (ResourceQ™; Amersham Biosciences). Proteins were eluted with a linear gradient (0.00-0.04 M NaCl in 16 ml buffer A; flow rate 1 ml/min). rDMBT1 containing fractions were pooled and loaded on a Sephacryl S-300 High Resolution (Amersham Biosciences) gel permeation chromatography column (d=2.6 cm; h=57 cm). Proteins were eluted with a linear flow rate of 15 cm/h PBS. Finally, rDMBT1 containing fractions were pooled and monitored for purity (about 90-95%) and integrity on silver-stained protein gels. The protein concentration was determined using the BCA Protein Assay Kit (Pierce) according to the instructions of the manufacturer.

Preparation of Bacteria.

*Streptococcus mutans* (Ingbritt), *Streptococcus gordonii* (HG 222 and DSM20568), *Escherichia coli* (F7 and OM36-1), and *Helicobacter pylori* (ATCC 43504) were gown and processed as described earlier. *Salmonella typhimurium* (strain SF1399: wild type; strain SF1195: Rc chemotype; strain SF1567: Rd1 chemotype; strain SF1398: Re chemotype) were kindly provided by Dr. Ben Appelmelk from the Free University of Amsterdam, The Netherlands, and were grown and processed as previously described for *E. coli*. The bacteria were diluted in the buffers depicted previously to a final OD$_{700}$ of 0.5 or 1.0 corresponding to about 0.5 and 1.0×10$^9$ cells/ml respectively.

Turbidometric Aggregation Assays.

For quantitative measurements of bacterial aggregation, we added 200 µl peptide stock solution (1 mg/ml in 10% DMSO) diluted with 300 µl TBS containing 0.1% v/v Tween 20 and 1 mM CaCl$_2$ (TBS-TC) to 500 µl of the respective bacterial suspensions to obtain final peptide concentrations of 200 µl. As controls, we used bacterial suspensions, to which 200 µl 10% (v/v %) DMSO in H$_2$O and 300 µl TBS-TC were added. Bacterial aggregation was monitored by measuring the optical density at 700 nm in intervals of 1 min for 1 h in a spectrophotometer (UVICON 930, Kontron Instruments). For the semi-quantitative high-throughput competition assays, we first determined the allowed pH range for DMBT1pbs1-mediated aggregation of *S. gordonii* and *E. coli* by using TBS-TC adjusted with either HCl or NaOH. The pH range from 6.0 to 7.5 did not affect aggregation, while pHs below or above deccelerated the process. Accordingly, only substance concentrations that did not change the pH beyond the allowed range were scored (Table 1). For sulfated agents, we additionally ascertained inhibitory effects in the absence of 1 mM CaCl$_2$. For monitoring competitive effects, we pre-incubated 20 µl of the DMBT1pbs1 stock solution (20 µg) with 20 µl of the respective substance solutions in 48-well microtiter plates at room temperature (RT) for 2 min. As reference served 20 µl 10% (v/v) DMSO solution in H$_2$O mixed with 20 µl of the solvents of the respective substances. Afterwards, 100 µl of *S. gordonii* or *E. coli* (resuspended in TBS-TC or TBS-T, respectively, for the calcium-free assays) solution was added simultaneously to each well using a multichannel pipette. Bacterial aggregation was compared to the reference by visual inspection over a time course of 10 min. The scoring system was: (+++) no difference in aggregation compared to reference. (++) moderate inhibition of aggregation over the entire time course or maximal aggregation delayed by 1-5-min compared to reference; (+) strong inhibition of aggregation over the entire time course or maximal aggregation delayed by 5-10 min compared to reference; (−) complete inhibition of aggregation after 10 min. Each experiment was at least done in triplicate.

Binding Studies.

For the peptide binding studies we used, unless otherwise indicated, 20 µg/ml peptide in a total volume of 100 µl (dilution in coating buffer, 100 mM carbonate buffer, pH 9.6) for the coating of high affinity ELISA plates (Microlon, Fluotrac 600; Greiner). When immobilizing rDMBT1, purified, partially purified DMBT1 or substances to be tested, we applied serial dilutions in coating buffer onto the plates. Coating was done at 4° C. for 16 h and was followed by three washes with PBS-T with 1 mM CaCl$_2$ (PBS-TC). For the analysis of bacterial binding to immobilized peptides or protein, we incubated the wells with 100 µl bacterial solution at 37° C. for 2 h. After removal of unbound bacteria, 100 µl of SYTO-9 solution (Molecular Probes), which is a cell-permeable fluorescent DNA dye, was added, plates were incubated in the dark for 15 min and after three washes with PBS-TC, fluorescence was measured by determination of the emission at 535 nm with a microtiter plate reader (488 n=excitation; Fluostar Galaxy, BMG Laboratories). DNA binding to immobilized DMBT1 was analyzed by using the same plasmid (LPS-free preparation) as used for the competitive aggregation and transfection assays (see below). Bound DNA was detected analogous to detection of bacteria except for using SYTQ-13 as dye. In inverse assays, we coated serial dilutions of the candidate substance onto microtiter plates (Microlon, F-Form; Greiner). After incubation at 4° C. for 16 h and three washes with TBS-TC, rDMBT1 or DMBT1 (10 µg/ml in TBS-TC) were added to each well and incubated at 37° C. for 1 h The plates were then washed three times with 200 µl TBS-TC, incubated at 37° C. for 1 h with the DMBT1-specific mouse monoclonal antibodies anti(A2) gp-340 (Hyb213-6; Antibody-Shop), and, mAb143 (kindly provided by Dr. D. Malamud) diluted 1:10,000 in TBS-TC, washed again five times with TBS-TC, and incubated at 37° C. for 1 h with a rabbit anti-mouse IgG-HRP conjugate (Jackson; dilution 1:10,000 in TBS-TC). Subsequent to three washes with TBS-TC 100 µl substrate (125 µg/ml 3,3',5,5'-Tetramethyl-benzidine; 125 µg/ml in 0.1 M citrate buffer pH 4.5 with 0.05% (v/v) H$_2$O$_2$) were added, and after incubation at RT for 10-15 min, the reaction was stopped by addition of 50 µl 2 M HCl. The intensity of the dye reaction was measured by absorption at 450 nm in an ELISA reader (EL800; Bio-Tec Instruments Inc.). Each ELISA plate contained duplicate rows with serial dilutions incubated with rDMBT1 or DMBT1. As control served duplicate rows treated in the same manner, except for omitting rDMBT1 and DMBT1. Each experiment was at least done in triplicate.

ELISA Assay for DMBT1 Quantification.

In order to determine the DMBT1 concentrations in partially purified samples obtained from different donors, serial dilutions of the samples and of purified rDMBT1 and/or purified DMBT1 in coating buffer were coated onto high affinity microtiter plates (Greiner-F, Polysorp, Nunc) at 37° C. for 2 h. The plates were washed with TBS-TC as described above and subsequently incubated at 37° C. for 1 h with a 1:500 dilution of the mouse monoclonal antibody anti-DMBT1h12. After washing, the plates were incubated at 37° C. for 1 h with a rabbit anti-mouse IgG-HP conjugate (dilution 1:2,000 in TBS-TC; DAKO A/S Denmark). Subsequent to three washes with TBS-TC, 100 µl substrate (3,3',5,5'-Tetramethyl-benzidine; 125 µg/ml in citrate buffer pH 4.5 with 0.05% (v/v) $H_2O_2$) were added, the reactions were stopped, and the intensities of the dye reaction was measured as described above. Comparison to purified rDMBT1/DMBT1 references delivered the concentrations of DMBT1 in partially purified parotid saliva samples. Because anti-DMBT1h12 recognizes a non-repetitive and non-variable epitope (amino acids 26-40 referred to EMBL Accession no. AJ243212), the approach enabled us to adjust wild type DMBT1 variants and variants with germline deletions irrespective of the presence of variable numbers of epitopes to equimolar amounts, which was confirmed by a second ELISA and Western blotting (see below and FIG. 4e)

Specification of Tested Substances.

Sucrose, maltose, dextrose, and the various salts tested were standard reagents obtained from Merck or Sigma. The DSS was the same as used in animal experiments. which revealed an increased susceptibility of $Dmbt1^{-/-}$ mice to DSS-induced tissue damage and inflammation ($M_r$=36-50 kDa; ICN Biomedicals Aurora; Bergmann et al., submitted). The following substances were obtained from Sigma with catalogue numbers in brackets: heparansulfate (H-7640), chondroitinsulfate B (C-3788), azoxymethane (A-9517), N-nitrosodiethlylamine (N-0258), *streptococcus sanguis* LTA (L-3765), *Staphylococcus aureus* LTA (L-2515), *Escherichia coli* LPS (L-3012), *Klebsiella pneumoniae* LPS (L-1770), *Salmonella typhimurium* LPS (L-6511), *Salmonella minnesota* LPS (chemotype Rd1; L-9391), L-α-phosphatidylcholine (P-279), CUROSURF™ with 80 mg/ml phospholipids from pig surfactant (54 mg/ml phosphatidylcholine and 30-5 mg/ml D-palmitoylphosphatidylcholine; overall: 99% polar phospholipids and 1% proteins) was obtained from Dey (Napa; Italy), and sIgA was purchased from Sigma. The dNTPs and the dNTP-Mix were from Roche Diagnostics. The DNA used in all experiments was the 4.7-kb plasmid pEGFP-N1 from Clontech.

Assays for Inhibition of Liposome-Mediated DNA-Transfer.

We used the colon cancer cell lines SW403 (human) and Colo26 (mouse) for analyzing inhibition of liposome-mediated DNA-transfer to mammalian cells. Twenty-four h prior to transfection, $0.5 \times 10^5$ cells per well were seeded in 500 µl RPMI (SW403) or DIM (Colo26) cell culture medium containing 10% v/v FCS on 24-well plates. For competitive assays, peptide and rDMBT1 solutions of various concentrations were filled up with sterile $H_2O_{bidest}$ to 40 µl. As controls served concentration-matched DMSO (for the peptides) and PBS (for rDMBT1) solutions. For preincubation of DNA, 9 µl Opti-MEM (Invitrogen) and 1 µl (0.5 µg) of the 4.7-kb pEGFP-N1 reporter plasmid (Clontech) were added to the peptides, rDMBT1, and the controls. After incubation at 37° C. for 30 min, 48 µl Opti-MEM and 2 µl Lipofectamine 2000 (Invitrogen) were added. The samples were then added to the wells after incubation at RT for 30 min. When preincubating phospholipids, we added 8 µl Opti-MEM and 2 µl Lipofectamine 2000 to the 40 µl of the peptide, rDMBT1, and control solutions, followed by preincubation at 37° C. for 30 min as descended above. Afterwards, 49 µl Opti-MEM and 1 µl (0.5 µg) pEGFP-N1 plasmid DNA were added, and subsequent to incubation at RT for 30 min, the mixture was pipetted onto the cells. When including centrifugation steps, the first incubation (37° C. for 30 min) was followed by centrifugation (13,000 rpm, +4° C. for 15 min) and the supernatants were processed further as described above. The cells were incubated with the samples at 37° C. for 24 h in a $CO_2$ incubator. Afterwards, image acquisition was done using an Axiovert 25 microscope (Zeiss; Germany). Per well we randomly selected five areas at 200-fold magnification and scored the percentage of EGFP-expressing cells. Mean values and standard errors of the means (SEMs) were calculated from at least two independent experiments.

Western Blot Analyses.

Protein samples were separated on a Pharmacia Phast system (Pharmacia-LKB; Uppsala; Sweden) using 4-15% polyacrylamide gradient gels by denaturing SDS-PAGE under non-reducing conditions, transferred to nitrocellulose membranes (Schleicher and Schuell), and DMBT1 was detected by the mAb anti-DMBT1h12 using the conditions described before. By Western blotting, we confirmed protein sizes in and equalization of the samples containing partially purified DMBT1 (FIG. 4e).

Genetic Analyses.

Studies of the genomic configuration of DMBT1 were approved by the responsible ethics committee at the University Heidelberg, Germany. Blood samples were collected from 200 healthy volunteers (ethnic background: Caucasian) and genomic DNA was extracted from peripheral blood leukocytes by standard procedures. We used 20 µg RsaI-digested DNA and probe DMBT1/sr1sid2 for an initial Southern blot screen of the DMBT1 configuration in this panel under the conditions depicted elsewhere.

2. Material and Methods (Referring to Examples 6 to 9)

Molecular Cloning.

Starting from a 10-kb HindIII mouse genomic fragment subcloned into pBluescript SK(−) (Dmbt1c1; FIG. 1a), a 4.1-kb PstI/HincII fragment was cloned 5' to a LoxP site utilizing the preceding HindIII recognition site to give rise to the left homology arm. The 1224-bp HincII/AciI fragment was amplified from Dmbt1c1 using primers introducing a 5' SpeI and a 3' XbaI site (Dmbt1/KOcf1: 5'-GCA CTA GTG GCA AGG TAA AGG AGG CAA G-3'(SEQ ID NO: 3); Dmbt1/KOcf1: 5'-TGT CTA GAC CTT CAC CGA ACG ACT CC-3' (SEQ ID NO: 4) and subsequently inserted 3' to the LoxP site. A 4.0-kb AciI/BamHI fragment (the latter site locating within the vector sequence) from Dmbt1c1 was separately subcloned 3' to a NeoTK cassette flanked by two LoxP sites to give rise to the right homology arm. The insert was then excised and cloned 3' to the HincII/AciI fragment. A diphtheria toxin A (DTA) cassette under the control of the MCI promoter allowing for negative selection of non-homologous recombinants was cloned 5' to the left homology arm to give rise to the final targeting construct (FIG. 1a).

Generation of Dmbt1 Knockout Mice.

Twenty-five µg linearized plasmid DNA of the targeting construct was transfected into $1 \times 10^7$ E14.1 mouse ES-cells by electroporation using standard conditions. Southern blot screens of 240 G418-resistant ES-cell clones using probe dmbt1/KOa (340-bp PCR product amplified with primers Dmbt1/KOaf1: 5'-CCC AGT GTC AGT GAG CTT AG-3' (SEQ ID NO: 5) and Dmbt1/KOar1: 5'-GCT CAA CAA CTG CTA CCA TAC-3' (SEQ ID NO: 6); FIG. 1a), yielded 3 clones heterozygous for the new 4.7-kb HindIII fragment representing the targeted allele. Single integration into the authentic site was further confirmed by hybridization with a Neo probe. Transient transfection of $3 \times 10^6$ cells of ES cell clone 2 with 5 µg Cre-recombinase encoding plasmid DNA and Southern blot analysis (probe: Dmbt1/KOb; FIG. 1a) of 126 subclones delivered 13 clones heterozygous for the 2.9-kb BglII fragment representing the knockout allele (FIG. 1a). Sixty-nine C57BL/6 blastocyst injections and embryo-transfer to pseudopregnant foster mothers yielded 10 highly chimaeric males (>90% coat chimaerism). Three of four males mated with C57BL/6 females displayed germline transmission of the knockout allele. By intercrosses of heterozygous F1 mice we obtained homozygous mutant F2 Dmbt1$^{-/-}$ mice at expected Mendelian frequencies. Mouse tail biopsies were used for genotyping with probe Dmbt1/KOb (480-bp PCR product amplified with primers Dmbt1/KObf1: 5'-CTT TTG TGG GGT CAA ATT CTG TC-3' (SEQ ID NO: 7') and Dmbt1/KObr1: 5'-CTG TTG GTC CCT TGA CCT G-3' (SEQ ID NO: 8)) by Southern blotting as shown in FIG. 1b.

Northern Blot Analyses.

For systematic expression analyses in mouse tissues, Northern blots containing 20 µg total RNA (BioCat) were utilized. Probes DMBT1/sr1sid2 (5'-end up to SID2), DMBT1/hfl2-2.1 (3'-end), and DMBT1/8 kb-3.8 (SID7 to ZP) were each used at three different hybridization temperatures (55° C., 60° C., 65° C.) under the conditions described before[3] and delivered identical results. For comparative analyses between Dmbt1$^{+/+}$ and Dmbt1$^{-/-}$ tissues, total RNA was prepared with the RNeasy kit (Qiagen) according to the instructions of the supplier. A total of 4.5 µg RNA (comprising a pool of 1.5 µg RNA each from colon tissues of three mice) was separated by denaturing RNA gel electrophoresis according to standard procedures. Integrity of the RNA was monitored by methyleneblue staining after Northern blotting and by hybridization of β-actin probe. Dmbt1 transcripts were detected via the P$^{32}$-labeled probe DMBT1/8 kb-3.8 (hybridization temperature: 60° C.). For the quantitative analysis of Dmbt1 expression levels, signal intensities on Northern blots hybridized with the radioactively labeled DMBT1/8 kb-3.8 and β-actin probes were determined using the Storm 860 PhosphorImager (Molecular Dynamics). The Dmbt1:β-actin ratios and percentage of expression referred to the respective reference present on the same Northern blot were subsequently calculated. For a direct comparison of Dmbt1 expression levels analyzed on separate Northern blots, we used the signal ratio obtained from the proximal colon of untreated females as reference to which the expression levels in the other untreated pools were adjusted to. We then multiplicated these values with the respective factors of upregulation to obtain the adjusted ratios in FIG. 6d. This allowed for monitoring in which treatment, tissue and gender the highest expression levels are obtained Western Blot Analyses.

Protein samples were prepared from mouse tissues snap-frozen in liquid nitrogen. After homogenization using a Micro-Dismembrator S (B. Braun; Germany) the samples were dissolved in RIPA lysis buffer (1×PBS, 1% V/V, Nonidet P-40, 0.5% w/v sodiumdeoxycholate, and 0.1% w/N SDS) containing protease inhibitors (Complete; Roche Diagnostics; Germany). Nucleic acids were fragmented by addition of 1 µl benzonase and incubation on ice for 1 h. The protein concentration was determined using the BCA Protein Assay Kit (Pierce) according to the instructions of the manufacturer. For Western blot studies, 15 µg of the protein samples were separated on 4-20% gradient gels (Novex) by denaturig SDS-PAGE under non-reducing conditions and transferred to PVDF membranes (Immobilon-P; Millipore). Membranes were blocked with 5% (w/v) skim milk powder at 4° C. overnight. For detection of mouse Dmbt1 we used polyclonal rabbit antisera (diluted 1:100 in 5% (w/v) skim milk powder) raised against the salivary variant (anti-DMBT1$^{SAG}$)[33] and the respiratory tract variant of DMBT1 (anti-DMBT1$^{GP340}$)[34]. After incubation at room temperature (RT) for 2 h. the membranes were washed three times in PBS with 0.1% v/V Tween 20 (PBS-T) for 10 min, incubated at RT for 1 h with a mouse anti-rabbit-IgG-POD conjugate (dilution 1:100; Santa Cruz) followed by another three washes with PBS-T for 10 min each. For signal detection, we used a chemoluminescence detection kit (Amersham) as recommended by the supplier.

RNA In Situ Hybridization.

A 0.4 kb fragment of human DMBT1 (SID5 to SID6) was subcloned into the pCRII-TOPO vector (Invitrogen). One µg XhoI or BamHI-linearized plasmid DNA was transcribed in vitro using SP6 polymerase (antisense stand) or T7 polymerase (sense strand), respectively, in the presence of digoxygenin-labeled UTP. Paraformaldehyde-fixed (4% w/v in PBS) paraffin-embedded tissue sections (3-4 µm) were deparaffinized by xylol and a decreasing ethanol series (100-70%), afterwards washed twice for 5 min in DEPC-H$_2$O and incubated at 4° C. for 10 min in 4% w/v, paraformaldehyde in PBS. After three washes with PBS, the sections were incubated at 37° C. for 30 min with Proteinase K (10 µg/ml in TE pH 8.0), washed once with PBS, treated with 0.1 M triethanolamine (pH 8.0) containing 1/400 volume acetic acid anhydride at RT for 20 min, washed twice with PBS, and subjected to an increasing ethanol series (70-100%). The slides were prehybridized with hybridization solution (50% v/v formamide; 0.2 M DTT; 0.33 M NaCl, 10% w/v DSS; 1/50 volume Denhardts reagent; 1 mM EDTA pH 8.0; 20 mM Tris-HCl pH 7.4; 0.5 mg/ml tRNA; 0.1 mg/ml salmon sperm DNA) at 47° C. for 2 h in a humid chamber. Subsequently, the sections were incubated with hybridization solution with 8 ng/µl of denatured digoxigenin-labeled RNA probe at 47° C. for 20 h in a humid chamber, washed with 2×SSC at 47° C. for 30 min, with 50% formamide containing 0.5×SSC at 47° C. for 1 h, with 50% formamide containing 0.1×SSC at 47° C. for 30 min, with 0.2×SSC at RT for 10 min, with buffer 1 (100 mM Tris-HCl pH 7.4; 150 mm NaCl) at RT for 10 min and incubated at RT for 30 nm in Blocking Solution (Roche Diagnostics; used as recommended by the supplier). Afterwards, the sections were incubated with sheep-anti-DIG-AP (Roche Diagnostics) diluted 1:500 in Blocking Solution at RT for 2 h in a humid chamber, washed two times 15 nm in with buffer 1, for 2 min with buffer 3 (pH 9.5; containing 100 mM Tris-HCl pH 7.4, 100 mM NaCl, 50 mM MgCl$_2$) and incubated at RT for 2-3 h in a dark humid chamber with 100 µl staining solution per section (buffer 3 with 0.45 µl NBT and 0.35 µl BCIP). After two washes at RT for 15 n in buffer 4 (pH 8.0; containing 100 mM Tris-HCl pH 7.4, 10 mM EDTA pH 8.0) and PBS, respectively, the sections were conserved using an aqueous mounting medium (Crystal mount; Biomeda)

Immunohistochemical Analyses.

Paraformaldehyde-fixed (4% w/v in PBS) paraffin-embedded tissue sections (34 µm) were prepared and analyzed with polyclonal anti-DMBT1$^{SAG}$ (1:100) using the protocol previously described for the monoclonal antibody anti-DMBT1h12 and a hematoxyline counterstaining.

DSS Treatment.

Age-matched Dmbt1$^{-/-}$ and wild type Dmbt1$^{+/+}$ littermates (9-12 weeks old) obtained from heterozygous breedings were kept under pathogen-free standardized conditions. The mice obtained 2.5% DSS (w/v; M$_r$=36-50 kDa; ICN Biomedicals Aurora) in drinking water (n=16 and n=13 for Dmbt1$^{+/+}$ males and females, respectively; n=16 and n=14 for Dmbt1$^{-/-}$ males and females, respectively) at day 1 for 8 days and were sacrificed at day 10 or 5% DSS for 7 days and were immediately sacrificed (FIG. 3a; n=17 and n=14 for Dmbt1$^{+/+}$ males and females, respectively; n=13 and n=14 for Dmbt1$^{-/-}$ males and females, respectively). All animal experiments were approved by the Regierungspräsidium Karlsruhe, Germany.

Biometrical and Histopathological Analyses.

Body weights were monitored daily and colon lengths were measured immediately after organ resection from the end of the cecum to the rectum. Afterwards, the cecum was removed and the colon was cut in the middle to separate the proximal and distal part, respectively. Two longitudinal 3-4 µm sections every 120 µm of the paraformaldehyde-fixed and paraffin-embedded tissues were used for hematoxyline/eosin staining. Histopathological inspection of 14-18 sections per proximal and distal colon. respectively, of each animal was independently done by two pathologists blinded for genotype and gender of the mice. For histopathological scoring of epithelial damage and inflammation we applied conventional colitis scoring schemes (range 0-3; ref. 35). In addition, percentage of affected epithelial area (damage and inflammation) and granulocyte/lymphocyte infiltration (0: no, 1: low, 2: intermediate. 3: high number of infiltrating cells) was semi-quantitatively scored. The combined damage score (CDS) was calculated by addition of epithelial damage, inflammation, granulocyte, and lymphocyte scores with the percentage of affected area divided by 33.3, so that the latter value was equalized to the other scoring systems. This resulted in a theoretical range from 0 (no damage) to 15 (maximum damage).

Statistical Analyses.

Statistical analysis of mouse mortality was carried out by comparison of survival probabilities using the two-tailed log-rank test. Body weight losses were analyzed utilizing a linear mixed-effects-model for time-dependent data[36] using the absolute body weight values at the days of DSS treatment, i.e. day 1-8 for 2.5% DSS and day 1-7 for 5.0% DSS. Time-dependency was modeled using a second order polynomial. Colon length were compared by two-tailed Mann-Whitney U-tests. Statistical evaluation of histopathological scores was carried out using the two-tailed Mann-Whitney U-test, except for comparisons between the distal and proximal colon within the 2.5% DSS and 5.0% DSS experiment, respectively. Here, we used pair wise comparison by the two-tailed Wilcoxon signed rank test. To correct for the family-wise Type I error rate (FWER), P-values were adjusted for multiple testing using the Holm procedures[37]. "Families" were defined by the four comparisons Dmbt1$^{-/-}$ males versus Dmbt1$^{+/+}$ males, Dmbt1$^{-/-}$ females versus Dmbt1$^{+/+}$ females, Dmbt1$^{-/-}$ males versus Dmbt1$^{-/-}$ females, and Dmbt1$^{+/+}$ males versus Dmbt1$^{+/+}$ females. Additionally, the FWER was corrected for the four comparisons of the mean combined damage scores between distal and proximal colon for treatment with 2.5% and 5.0% DSS and between treatment with 2.5% DSS and 5.0% DSS for distal and proximal colon P-values $\leq$0.05 were considered as statistically significant.

Synthetic peptides. The synthetic peptide DMBT1-SR-CRP2 (NH$_2$-QGRVEVLYRGSWGTVC-COOH (SEQ ID NO: 16); purity >85%) comprising the pathogen-binding site of DMBT1 was obtained from Eurogentec (Belgium) and resuspended to a final concentration of 1 mg/ml in H$_2$O$_{bidest}$ containing 10% v/v DMSO.

Recombinant Expression and Purification of Human DMBT1.

Detailed protocols on molecular cloning, the generation of stably transfected cell lines and the purification of human recombinant DMBT1 (rDMBT1) will be published elsewhere (End et al., in preparation) or are available from the authors upon request Briefly, the largest known DMBT1 open reading frame corresponding to the DMBT1/8 kb.2 variant (EMBL Accession no AJ243212) was cloned into the pT-REx-DEST30 vector (Invitrogen) under the control of a tetracycline-inducible promoter. The plasmid was transfected into the cell line T-REx-CHO (nitrogen), which constitutively expresses the Tet-repressor protein, using Fugene 6 (Roche Diagnostics). Stable transfectands were selected by addition of 1 mg/ml G418 and 0.001 mg/ml blasticidin. Subcloning was done by low-density plating (20 cells per 50 cm$^2$) and picking of single colonies after 15 d under selection pressure. Clone CHO-DMBT1/8 kb.2-T3 displayed highest expression levels upon induction with 10 µg/ml tetracycline for 48 h and predicted transcript and protein size in Northern blot and Western blot analyses using probe DMBT1/8 kb-3.8 and the monoclonal antibody anti-DMBT1h12 under the conditions described before[12]. For the production of rDMBT1, cells were grown in DMEM/F12 containing 10 µg/ml tetracycline for 48 h, the supernatants were collected, diluted 1:3 in buffer A (20 mM Tris-HCl; 10 mM EDTA, pH 8.0), and filtered by 0.22 µm bottle top filters prior to loading on an 1 ml anion-exchanger column (ResourceQ™, Amersham Biosciences). Proteins were eluted with a linear gradient (0.00-0.04 M NaCl in 16 ml buffer A; flow rate 1 ml/min). rDMBT1 containing fractions were pooled and loaded on a Sephacryl S-300 High Resolution (Amersham Biosciences) gel permeation chromatography column (d=2.6 cm; h=57 cm). Proteins were eluted with a linear flow rate of 15 cm/h PBS. Finally, purified rDMBT1 containing fractions were pooled and monitored for purity (about 90-95%) and integrity on silver-stained protein gels. The protein concentration was determined using the BCA. Protein Assay Kit (Pierce) according to the instructions of the manufacturer.

Preparation of Bacteria.

*Streptococcus gordonii* (strain: DSM90568) was cultured under anaerobic conditions as described before[17], harvested by centrifugation at 3,000 g, washed twice with PBS containing 10 mM EDTA and once with PBS and finally resuspended in PBS to a final OD$_{700}$ of 2.0 corresponding to about 2.0×10$^9$ cells/ml, respectively.

Turbidometric Competition Assays.

Competition assays were carried out in a final volume of 500 µl at RT. *Streptococcus gordonii* (250 µl in PBS) was mixed with 100 µl synthetic peptide DMBT1-SRCRP2 diluted 1:1 in PBS (final concentration in the assay: 100 µg/ml) or 100 µl purified rDMBT1 in PBS (final concentration in the assay: 15 µg/ml) and 150 µl of the respective competitor stock solutions, so that the final concentrations ranged from 0.32% to 2.50% (w/v) DSS and 0.28% to 0.84% (w/h) degraded carrageenan. Samples with 0.0% competitor served as controls. The samples were placed in a spectrophotometer (Anthelie; SECOMAN, France) and the OD$_{700}$-value was measured in intervals of 3 minutes. Each experiment was at least done in triplicate. For the DSS competition studies, we used the same DSS as in the animal experiments (M$_r$=36-50 kDa; ICN Biomedicals Aurora). High molecular weight lambda carrageenan was obtained from Sigma (Taufkirchen; Germany). Prior to use, 5% (w/v) carrageenan was dissolved in 0.1 M HCl and incubated at 60° C. for 3 h to achieve acid hydrolysis, which yields degradation products of about 20-40 kDa[38]. Afterwards, the pH was adjusted to 7.0 by addition of 0.1 M NaOH and the solution was passed through a sterile filter.

Binding Assays.

DSS was serially diluted in coating buffer (100 mM carbonate buffer, pH 9.6) to obtain final concentrations of 2.5% to 0.02% (w/v). One hundred μl of the samples were applied onto ELISA plates (Microlon, F-Form; Greiner, Germany) and coating was done at 4° C. for 16 h. Acid hydrolyzed and pH-adjusted lambda carrageenan was serially diluted with the solvent (approximately 50 mM HCl and 50 mM NaOH) to obtain concentrations ranging from 2.8% to 0.0055% (w/A) and coating of ELISA plates was done at 37° C. for 2 h. After coating and three washes with TBS containing 0.1% (v/v) Tween 20 (TBS-T), rDMBT1 (10 μg/ml in TBS-T) was added to each well and incubated at 37° C. for 1 h. The wells were then washed five times with 200 μl TBS-T, incubated at 37° C. for 1 h with the DMBT1-specific mouse monoclonal antibody anti(A2) gp-340 (Hyb213-06; Antibody-Shop; dilution 1:10,000 in TBS-T), washed again five-times with TBS-T, and incubated at 37° C. for 1 h with a rabbit anti-mouse IgG-HRP conjugate (Jackson; dilution 1:10,000 in TBS-T). Subsequent to five washes with TBS-T, 150 μl substrate (125 μg/ml 3,3', 5'-Tetramethyl-benzidine; in 0.1 M citrate buffer pH 4.5 with 0.05% (v/v) $H_2O_2$) were added, and after incubation at RT for 10-15 min the reaction was stopped by addition of 50 W 2 M HCl. The intensity of the dye reaction was measured at 450 nm in an ELISA reader (EL800; Bio-Tec Instruments Inc.). Each ELISA plate contained duplicate rows with serial dilutions incubated with rDMBT1. As control served duplicate rows with serial dilutions of DSS and lambda carrageenan treated in the same manner, except for omitting rDMBT1. Each experiment was at least done in triplicate.

The invention claimed is:

1. A method for identifying an agent possessing at least one accessible sulphate and/or at least one accessible phosphate group and/or regulating the effective amount of the said agent in a sample comprising the steps of:
  a) incubating a sample with a polypeptide comprising the sequence of SEQ ID NO:1, or a functional derivative or fragment thereof, or of a nucleic acid comprising the sequence of SEQ ID NO:2, or a functional derivative or fragment thereof; and,
  b) identifying the complex comprising the agent possessing at least one accessible sulphate and/or phosphate group and the polypeptide/nucleic acid as defined in step a).

2. The method according to claim 1, wherein the identifying and/or regulating is carried out by using the at least one accessible sulphate and/or at least one accessible phosphate group.

3. The method according to claim 1, wherein the identifying and/or regulating is carried out by varying the amount and/or the length of the polypeptide or of the nucleic acid.

4. The method according to claim 1, wherein regulating the effective amount of an agent includes inactivating and/or capturing said agent.

5. The method according to claim 1, wherein the agent comprises an agent being a microorganism.

6. The method of claim 5, wherein said microorganism is a bacterium or a virus, the bacteria including the genera *Streptococcus, Staphylococcus, Escherichia, Helicobacter, Salmonella* and *Bacillus*.

7. The method of claim 1, wherein said agent comprises an agent being a non-living compound or composition.

8. The method of claim 7, wherein said non-living compound or composition is selected from the group consisting of DSS, sulphated carbohydrates, preferably heparan sulphate, chondroitin sulphate, carrageenan, disodium sulphate, phosphate group exposing compounds or compositions, preferably DNA, deoxynucleotides, surfactant phospholipids, sulphated mucins, sodium-, potassium- and calcium phosphate exposing compounds or compositions.

9. The method according to claim 1, wherein the sample is a biological, a food derived, a pharmaceutical or a cosmetic sample.

10. A method for diagnosing the susceptibility of an individual to an agent which possesses at least one sulphate and/or at least one phosphate group, the method comprising detecting in a sample a polypeptide comprising the sequence of SEQ ID NO:1, a functional fragment or derivative thereof, or a nucleic acid comprising the sequence of SEQ ID NO:2, or a functional fragment or derivative thereof, wherein a shortened polypeptide or a shortened nucleic acid as compared to the full-length polypeptide or nucleic acid as defined by SEQ ID NO: 1 or SEQ ID NO: 2 is indicative of an increased susceptibility.

11. The method according to claim 10, wherein the sample is a body fluid, preferably blood, saliva, semen or liquor, which is isolated from the individual.

12. The method according to claim 10, wherein the agent comprises an agent being a microorganism.

13. The method of claim 12, wherein said microorganism is a bacterium or a virus, the bacteria including the genera *Streptococcus, Staphylococcus, Escherichia, Helicobacter, Salmonella* and *Bacillus*.

14. The method of claim 10, wherein said agent comprises an agent being a non-living compared or composition.

15. The method of claim 14, wherein said non-living compound or composition is selected from the group consisting of DSS, sulphated carbohydrates, preferably heparan sulphate, chondroitin sulphate, carrageenan, disodium sulphate, phosphate group exposing compounds or compositions, preferably DNA, deoxynucleotides, surfactant phospholipids, sulphated mucins, sodium-, potassium- and calcium phosphate exposing compounds or compositions.

16. A method for determining in an individual the effective amount of a pharmaceutical comprising an agent which possesses at least one accessible sulphate and/or at least one accessible phosphate group, the method comprising detecting in a sample a polypeptide comprising the sequence of SEQ ID NO:1, a functional fragment or derivative thereof, or a nucleic acid comprising the sequence of SEQ ID NO:2, or a functional fragment or derivative thereof,
  wherein a shortened polypeptide or a shortened nucleic acid as compared to the full-length polypeptide or nucleic acid as defined by SEQ ID NO:1 or SEQ ID NO:2 is indicative for a lower effective amount.

17. The method of claim 16, wherein the sample is a body fluid, preferably blood, saliva, semen or liquor, which is isolated from the individual.

18. The method according to claim 16, wherein the agent comprises an agent being a microorganism.

19. The method of claim 18, wherein said microorganism is a bacterium or a virus, the bacteria including the genera *Streptococcus, Staphylococcus, Escherichia, Helicobacter, Salmonella* and *Bacillus*.

20. The method of claim 16, wherein said agent comprises an agent being a non-living compound or composition.

21. The method of claim 20, wherein said non-living compound or composition is selected from the group consisting of DSS, sulphated carbohydrates, preferably heparan sulphate, chondroitin sulphate, carrageenan, disodium sulphate, phosphate group exposing compounds or compositions, preferably DNA, deoxynucleotides, surfactant phospholipids, sulphated mucins, sodium-, potassium- and calcium phosphate exposing compounds or compositions.

22. An in vitro method for binding an agent which possesses at least one accessible sulphate group and/or at least one accessible phosphate group, the method comprising contacting the agent with an amino acid motif comprising 11 contiguous amino acids derived from a polypeptide comprising the sequence of SEQ ID NO:1.

23. The method according to claim 22, wherein the 11 contiguous amino acids possess a sequence selected from the sequences GRVEVLYRGSW (SEQ ID NO: 9), GRVEILYRGSW (SEQ ID NO: 10) and GRVEVLYQGSW (SEQ ID NO: 11).

24. The method according to claim 23, wherein the 11 contiguous amino acids possess the sequence GRVEVLYRGSW (SEQ ID NO: 9).

* * * * *

```
                        SEQUENCE LISTING

<160> NUMBER OF SEQ ID NOS: 8

<210> SEQ ID NO 1
<211> LENGTH: 2413
<212> TYPE: PRT
<213> ORGANISM: Homo sapiens

<400> SEQUENCE: 1

Met Gly Ile Ser Thr Val Ile Leu Glu Met Cys Leu Leu Trp Gly Gln
1               5                  10                  15

Val Leu Ser Thr Gly Gly Trp Ile Pro Arg Thr Thr Asp Tyr Ala Ser
            20                  25                  30

Leu Ile Pro Ser Glu Val Pro Leu Asp Pro Thr Val Ala Glu Gly Ser
        35                  40                  45

Pro Phe Pro Ser Glu Ser Thr Leu Glu Ser Thr Val Ala Glu Gly Ser
    50                  55                  60

Pro Ile Ser Leu Glu Ser Thr Leu Glu Ser Thr Val Ala Glu Gly Ser
65                  70                  75                  80

Leu Ile Pro Ser Glu Ser Thr Leu Glu Ser Thr Val Ala Glu Gly Ser
                85                  90                  95

Asp Ser Gly Leu Ala Leu Arg Leu Val Asn Gly Asp Gly Arg Cys Gln
            100                 105                 110

Gly Arg Val Glu Ile Leu Tyr Arg Gly Ser Trp Gly Thr Val Cys Asp
        115                 120                 125

Asp Ser Trp Asp Thr Asn Asp Ala Asn Val Val Cys Arg Gln Leu Gly
    130                 135                 140

Cys Gly Trp Ala Met Ser Ala Pro Gly Asn Ala Trp Phe Gly Gln Gly
145                 150                 155                 160

Ser Gly Pro Ile Ala Leu Asp Asp Val Arg Cys Ser Gly His Glu Ser
                165                 170                 175

Tyr Leu Trp Ser Cys Pro His Asn Gly Trp Leu Ser His Asn Cys Gly
            180                 185                 190

His Gly Glu Asp Ala Gly Val Ile Cys Ser Ala Ala Gln Pro Gln Ser
        195                 200                 205

Thr Leu Arg Pro Glu Ser Trp Pro Val Arg Ile Ser Pro Pro Val Pro
    210                 215                 220

Thr Glu Gly Ser Glu Ser Ser Leu Ala Leu Arg Leu Val Asn Gly Gly
225                 230                 235                 240

Asp Arg Cys Arg Gly Arg Val Glu Val Leu Tyr Arg Gly Ser Trp Gly
```

```
                    245                 250                 255
Thr Val Cys Asp Asp Tyr Trp Asp Thr Asn Asp Ala Asn Val Val Cys
                260                 265                 270

Arg Gln Leu Gly Cys Gly Trp Ala Met Ser Ala Pro Gly Asn Ala Gln
            275                 280                 285

Phe Gly Gln Gly Ser Gly Pro Ile Val Leu Asp Asp Val Arg Cys Ser
        290                 295                 300

Gly His Glu Ser Tyr Leu Trp Ser Cys Pro His Asn Gly Trp Leu Thr
305                 310                 315                 320

His Asn Cys Gly His Ser Glu Asp Ala Gly Val Ile Cys Ser Ala Pro
                325                 330                 335

Gln Ser Arg Pro Thr Pro Ser Pro Asp Thr Trp Pro Thr Ser His Ala
            340                 345                 350

Ser Thr Ala Gly Pro Glu Ser Leu Ala Leu Arg Leu Val Asn Gly
        355                 360                 365

Gly Asp Arg Cys Gln Gly Arg Val Glu Val Leu Tyr Arg Gly Ser Trp
370                 375                 380

Gly Thr Val Cys Asp Asp Ser Trp Asp Thr Ser Asp Ala Asn Val Val
385                 390                 395                 400

Cys Arg Gln Leu Gly Cys Gly Trp Ala Thr Ser Ala Pro Gly Asn Ala
                405                 410                 415

Arg Phe Gly Gln Gly Ser Gly Pro Ile Val Leu Asp Asp Val Arg Cys
            420                 425                 430

Ser Gly Tyr Glu Ser Tyr Leu Trp Ser Cys Pro His Asn Gly Trp Leu
        435                 440                 445

Ser His Asn Cys Gln His Ser Glu Asp Ala Gly Val Ile Cys Ser Ala
    450                 455                 460

Ala His Ser Trp Ser Thr Pro Ser Pro Asp Thr Leu Pro Thr Ile Thr
465                 470                 475                 480

Leu Pro Ala Ser Thr Val Gly Ser Glu Ser Ser Leu Ala Leu Arg Leu
                485                 490                 495

Val Asn Gly Gly Asp Arg Cys Gln Gly Arg Val Glu Val Leu Tyr Arg
            500                 505                 510

Gly Ser Trp Gly Thr Val Cys Asp Asp Ser Trp Asp Thr Asn Asp Ala
        515                 520                 525

Asn Val Val Cys Arg Gln Leu Gly Cys Gly Trp Ala Met Leu Ala Pro
    530                 535                 540

Gly Asn Ala Arg Phe Gly Gln Gly Ser Gly Pro Ile Val Leu Asp Asp
545                 550                 555                 560

Val Arg Cys Ser Gly Asn Glu Ser Tyr Leu Trp Ser Cys Pro His Asn
                565                 570                 575

Gly Trp Leu Ser His Asn Cys Gly His Ser Glu Asp Ala Gly Val Ile
            580                 585                 590

Cys Ser Gly Pro Glu Ser Ser Leu Ala Leu Arg Leu Val Asn Gly Gly
        595                 600                 605

Asp Arg Cys Gln Gly Arg Val Glu Val Leu Tyr Arg Gly Ser Trp Gly
    610                 615                 620

Thr Val Cys Asp Asp Ser Trp Asp Thr Asn Asp Ala Asn Val Val Cys
625                 630                 635                 640

Arg Gln Leu Gly Cys Gly Trp Ala Met Ser Ala Pro Gly Asn Ala Arg
                645                 650                 655

Phe Gly Gln Gly Ser Gly Pro Ile Val Leu Asp Asp Val Arg Cys Ser
            660                 665                 670
```

```
Gly His Glu Ser Tyr Leu Trp Ser Cys Pro Asn Asn Gly Trp Leu Ser
        675                 680                 685
His Asn Cys Gly His His Glu Asp Ala Gly Val Ile Cys Ser Ala Ala
    690                 695                 700
Gln Ser Arg Ser Thr Pro Arg Pro Asp Thr Leu Ser Thr Ile Thr Leu
705                 710                 715                 720
Pro Pro Ser Thr Val Gly Ser Glu Ser Leu Thr Leu Arg Leu Val
                725                 730                 735
Asn Gly Ser Asp Arg Cys Gln Gly Arg Val Glu Val Leu Tyr Arg Gly
                740                 745                 750
Ser Trp Gly Thr Val Cys Asp Asp Ser Trp Asp Thr Asn Asp Ala Asn
            755                 760                 765
Val Val Cys Arg Gln Leu Gly Cys Gly Trp Ala Thr Ser Ala Pro Gly
770                 775                 780
Asn Ala Arg Phe Gly Gln Gly Ser Gly Pro Ile Val Leu Asp Asp Val
785                 790                 795                 800
Arg Cys Ser Gly His Glu Ser Tyr Leu Trp Ser Cys Pro His Asn Gly
                805                 810                 815
Trp Leu Ser His Asn Cys Gly His His Glu Asp Ala Gly Val Ile Cys
                820                 825                 830
Ser Val Ser Gln Ser Arg Pro Thr Pro Ser Pro Asp Thr Trp Pro Thr
    835                 840                 845
Ser His Ala Ser Thr Ala Gly Pro Glu Ser Ser Leu Ala Leu Arg Leu
850                 855                 860
Val Asn Gly Gly Asp Arg Cys Gln Gly Arg Val Glu Val Leu Tyr Arg
865                 870                 875                 880
Gly Ser Trp Gly Thr Val Cys Asp Asp Ser Trp Asp Thr Ser Asp Ala
                885                 890                 895
Asn Val Val Cys Arg Gln Leu Gly Cys Gly Trp Ala Thr Ser Ala Pro
            900                 905                 910
Gly Asn Ala Arg Phe Gly Gln Gly Ser Gly Pro Ile Val Leu Asp Asp
                915                 920                 925
Val Arg Cys Ser Gly Tyr Glu Ser Tyr Leu Trp Ser Cys Pro His Asn
930                 935                 940
Gly Trp Leu Ser His Asn Cys Gln His Ser Glu Asp Ala Gly Val Ile
945                 950                 955                 960
Cys Ser Ala Ala His Ser Trp Ser Thr Pro Ser Pro Asp Thr Leu Pro
                965                 970                 975
Thr Ile Thr Leu Pro Ala Ser Thr Val Gly Ser Glu Ser Leu Ala
                980                 985                 990
Leu Arg Leu Val Asn Gly Gly Asp Arg Cys Gln Gly Arg Val Glu Val
                995                 1000                1005
Leu Tyr Gln Gly Ser Trp Gly Thr Val Cys Asp Ser Trp Asp
    1010                1015                1020
Thr Asn Asp Ala Asn Val Val Cys Arg Gln Leu Gly Cys Gly Trp
        1025                1030                1035
Ala Met Ser Ala Pro Gly Asn Ala Arg Phe Gly Gln Gly Ser Gly
        1040                1045                1050
Pro Ile Val Leu Asp Asp Val Arg Cys Ser Gly His Glu Ser Tyr
        1055                1060                1065
Leu Trp Ser Cys Pro His Asn Gly Trp Leu Ser His Asn Cys Gly
        1070                1075                1080
His Ser Glu Asp Ala Gly Val Ile Cys Ser Ala Ser Gln Ser Arg
        1085                1090                1095
```

-continued

```
Pro Thr Pro Ser Pro Asp Thr Trp Pro Thr Ser His Ala Ser Thr
    1100                1105                1110
Ala Gly Ser Glu Ser Ser Leu Ala Leu Arg Leu Val Asn Gly Gly
    1115                1120                1125
Asp Arg Cys Gln Gly Arg Val Glu Val Leu Tyr Arg Gly Ser Trp
    1130                1135                1140
Gly Thr Val Cys Asp Asp Tyr Trp Asp Thr Asn Asp Ala Asn Val
    1145                1150                1155
Val Cys Arg Gln Leu Gly Cys Gly Trp Ala Met Ser Ala Pro Gly
    1160                1165                1170
Asn Ala Arg Phe Gly Gln Gly Ser Gly Pro Ile Val Leu Asp Asp
    1175                1180                1185
Val Arg Cys Ser Gly His Glu Ser Tyr Leu Trp Ser Cys Pro His
    1190                1195                1200
Asn Gly Trp Leu Ser His Asn Cys Gly His His Glu Asp Ala Gly
    1205                1210                1215
Val Ile Cys Ser Ala Ser Gln Ser Gln Pro Thr Pro Ser Pro Asp
    1220                1225                1230
Thr Trp Pro Thr Ser His Ala Ser Thr Ala Gly Ser Glu Ser Ser
    1235                1240                1245
Leu Ala Leu Arg Leu Val Asn Gly Gly Asp Arg Cys Gln Gly Arg
    1250                1255                1260
Val Glu Val Leu Tyr Arg Gly Ser Trp Gly Thr Val Cys Asp Asp
    1265                1270                1275
Tyr Trp Asp Thr Asn Asp Ala Asn Val Val Cys Arg Gln Leu Gly
    1280                1285                1290
Cys Ser Trp Ala Thr Ser Ala Pro Gly Asn Ala Arg Phe Gly Gln
    1295                1300                1305
Gly Ser Gly Pro Ile Val Leu Asp Asp Val Arg Cys Ser Gly His
    1310                1315                1320
Glu Ser Tyr Leu Trp Ser Cys Pro His Asn Gly Trp Phe Ser His
    1325                1330                1335
Asn Cys Gly His His Glu Asp Ala Gly Val Ile Cys Ser Ala Ser
    1340                1345                1350
Gln Ser Gln Pro Thr Pro Ser Pro Asp Thr Trp Pro Thr Ser His
    1355                1360                1365
Ala Ser Thr Ala Gly Ser Glu Ser Ser Leu Ala Leu Arg Leu Val
    1370                1375                1380
Asn Gly Gly Asp Arg Cys Gln Gly Arg Val Glu Val Leu Tyr Arg
    1385                1390                1395
Gly Ser Trp Gly Thr Val Cys Asp Asp Tyr Trp Asp Thr Asn Asp
    1400                1405                1410
Ala Asn Val Val Cys Arg Gln Leu Gly Cys Gly Trp Ala Thr Ser
    1415                1420                1425
Ala Pro Gly Asn Ala Arg Phe Gly Gln Gly Ser Gly Pro Ile Val
    1430                1435                1440
Leu Asp Asp Val Arg Cys Ser Gly His Glu Ser Tyr Leu Trp Ser
    1445                1450                1455
Cys Pro His Asn Gly Trp Leu Ser His Asn Cys Gly His His Glu
    1460                1465                1470
Asp Ala Gly Val Ile Cys Ser Ala Ser Gln Ser Gln Pro Thr Pro
    1475                1480                1485
Ser Pro Asp Thr Trp Pro Thr Ser Arg Ala Ser Thr Ala Gly Ser
```

-continued

```
            1490                1495                1500
Glu Ser Thr Leu Ala Leu Arg Leu Val Asn Gly Gly Asp Arg Cys
    1505                1510                1515
Arg Gly Arg Val Glu Val Leu Tyr Gln Gly Ser Trp Gly Thr Val
    1520                1525                1530
Cys Asp Asp Tyr Trp Asp Thr Asn Asp Ala Asn Val Val Cys Arg
    1535                1540                1545
Gln Leu Gly Cys Gly Trp Ala Met Ser Ala Pro Gly Asn Ala Gln
    1550                1555                1560
Phe Gly Gln Gly Ser Gly Pro Ile Val Leu Asp Asp Val Arg Cys
    1565                1570                1575
Ser Gly His Glu Ser Tyr Leu Trp Ser Cys Pro His Asn Gly Trp
    1580                1585                1590
Leu Ser His Asn Cys Gly His His Glu Asp Ala Gly Val Ile Cys
    1595                1600                1605
Ser Ala Ala Gln Ser Gln Ser Thr Pro Arg Pro Asp Thr Trp Leu
    1610                1615                1620
Thr Thr Asn Leu Pro Ala Leu Thr Val Gly Ser Glu Ser Ser Leu
    1625                1630                1635
Ala Leu Arg Leu Val Asn Gly Gly Asp Arg Cys Arg Gly Arg Val
    1640                1645                1650
Glu Val Leu Tyr Arg Gly Ser Trp Gly Thr Val Cys Asp Asp Ser
    1655                1660                1665
Trp Asp Thr Asn Asp Ala Asn Val Val Cys Arg Gln Leu Gly Cys
    1670                1675                1680
Gly Trp Ala Met Ser Ala Pro Gly Asn Ala Arg Phe Gly Gln Gly
    1685                1690                1695
Ser Gly Pro Ile Val Leu Asp Asp Val Arg Cys Ser Gly Asn Glu
    1700                1705                1710
Ser Tyr Leu Trp Ser Cys Pro His Lys Gly Trp Leu Thr His Asn
    1715                1720                1725
Cys Gly His His Glu Asp Ala Gly Val Ile Cys Ser Ala Thr Gln
    1730                1735                1740
Ile Asn Ser Thr Thr Thr Asp Trp Trp His Pro Thr Thr Thr Thr
    1745                1750                1755
Thr Ala Arg Pro Ser Ser Asn Cys Gly Gly Phe Leu Phe Tyr Ala
    1760                1765                1770
Ser Gly Thr Phe Ser Ser Pro Ser Tyr Pro Ala Tyr Tyr Pro Asn
    1775                1780                1785
Asn Ala Lys Cys Val Trp Glu Ile Glu Val Asn Ser Gly Tyr Arg
    1790                1795                1800
Ile Asn Leu Gly Phe Ser Asn Leu Lys Leu Glu Ala His His Asn
    1805                1810                1815
Cys Ser Phe Asp Tyr Val Glu Ile Phe Asp Gly Ser Leu Asn Ser
    1820                1825                1830
Ser Leu Leu Leu Gly Lys Ile Cys Asn Asp Thr Arg Gln Ile Phe
    1835                1840                1845
Thr Ser Ser Tyr Asn Arg Met Thr Ile His Phe Arg Ser Asp Ile
    1850                1855                1860
Ser Phe Gln Asn Thr Gly Phe Leu Ala Trp Tyr Asn Ser Phe Pro
    1865                1870                1875
Ser Asp Ala Thr Leu Arg Leu Val Asn Leu Asn Ser Ser Tyr Gly
    1880                1885                1890
```

```
Leu Cys Ala Gly Arg Val Glu Ile Tyr His Gly Gly Thr Trp Gly
1895                1900                1905

Thr Val Cys Asp Asp Ser Trp Thr Ile Gln Glu Ala Glu Val Val
1910                1915                1920

Cys Arg Gln Leu Gly Cys Gly Arg Ala Val Ser Ala Leu Gly Asn
1925                1930                1935

Ala Tyr Phe Gly Ser Gly Ser Gly Pro Ile Thr Leu Asp Asp Val
1940                1945                1950

Glu Cys Ser Gly Thr Glu Ser Thr Leu Trp Gln Cys Arg Asn Arg
1955                1960                1965

Gly Trp Phe Ser His Asn Cys Asn His Arg Glu Asp Ala Gly Val
1970                1975                1980

Ile Cys Ser Gly Asn His Leu Ser Thr Pro Ala Pro Phe Leu Asn
1985                1990                1995

Ile Thr Arg Pro Asn Thr Asp Tyr Ser Cys Gly Gly Phe Leu Ser
2000                2005                2010

Gln Pro Ser Gly Asp Phe Ser Ser Pro Phe Tyr Pro Gly Asn Tyr
2015                2020                2025

Pro Asn Asn Ala Lys Cys Val Trp Asp Ile Glu Val Gln Asn Asn
2030                2035                2040

Tyr Arg Val Thr Val Ile Phe Arg Asp Val Gln Leu Glu Gly Gly
2045                2050                2055

Cys Asn Tyr Asp Tyr Ile Glu Val Phe Asp Gly Pro Tyr Arg Ser
2060                2065                2070

Ser Pro Leu Ile Ala Arg Val Cys Asp Gly Ala Arg Gly Ser Phe
2075                2080                2085

Thr Ser Ser Ser Asn Phe Met Ser Ile Arg Phe Ile Ser Asp His
2090                2095                2100

Ser Ile Thr Arg Arg Gly Phe Arg Ala Glu Tyr Tyr Ser Ser Pro
2105                2110                2115

Ser Asn Asp Ser Thr Asn Leu Leu Cys Leu Pro Asn His Met Gln
2120                2125                2130

Ala Ser Val Ser Arg Ser Tyr Leu Gln Ser Leu Gly Phe Ser Ala
2135                2140                2145

Ser Asp Leu Val Ile Ser Thr Trp Asn Gly Tyr Tyr Glu Cys Arg
2150                2155                2160

Pro Gln Ile Thr Pro Asn Leu Val Ile Phe Thr Ile Pro Tyr Ser
2165                2170                2175

Gly Cys Gly Thr Phe Lys Gln Ala Asp Asn Asp Thr Ile Asp Tyr
2180                2185                2190

Ser Asn Phe Leu Thr Ala Ala Val Ser Gly Gly Ile Ile Lys Arg
2195                2200                2205

Arg Thr Asp Leu Arg Ile His Val Ser Cys Arg Met Leu Gln Asn
2210                2215                2220

Thr Trp Val Asp Thr Met Tyr Ile Ala Asn Asp Thr Ile His Val
2225                2230                2235

Ala Asn Asn Thr Ile Gln Val Glu Glu Val Gln Tyr Gly Asn Phe
2240                2245                2250

Asp Val Asn Ile Ser Phe Tyr Thr Ser Ser Ser Phe Leu Tyr Pro
2255                2260                2265

Val Thr Ser Arg Pro Tyr Tyr Val Asp Leu Asn Gln Asp Leu Tyr
2270                2275                2280

Val Gln Ala Glu Ile Leu His Ser Asp Ala Val Leu Thr Leu Phe
2285                2290                2295
```

| Val | Asp | Thr | Cys | Val | Ala | Ser | Pro | Tyr | Ser | Asn | Asp | Phe | Thr | Ser |
| | 2300 | | | | 2305 | | | | 2310 | | | | | |

| Leu | Thr | Tyr | Asp | Leu | Ile | Arg | Ser | Gly | Cys | Val | Arg | Asp | Asp | Thr |
| 2315 | | | | | 2320 | | | | | 2325 | | | | |

| Tyr | Gly | Pro | Tyr | Ser | Ser | Pro | Ser | Leu | Arg | Ile | Ala | Arg | Phe | Arg |
| | 2330 | | | | | 2335 | | | | 2340 | | | | |

| Phe | Arg | Ala | Phe | His | Phe | Leu | Asn | Arg | Phe | Pro | Ser | Val | Tyr | Leu |
| 2345 | | | | | 2350 | | | | | 2355 | | | | |

| Arg | Cys | Lys | Met | Val | Val | Cys | Arg | Ala | Tyr | Asp | Pro | Ser | Ser | Arg |
| | 2360 | | | | 2365 | | | | | 2370 | | | | |

| Cys | Tyr | Arg | Gly | Cys | Val | Leu | Arg | Ser | Lys | Arg | Asp | Val | Gly | Ser |
| 2375 | | | | | 2380 | | | | | 2385 | | | | |

| Tyr | Gln | Glu | Lys | Val | Asp | Val | Val | Leu | Gly | Pro | Ile | Gln | Leu | Gln |
| | 2390 | | | | 2395 | | | | | 2400 | | | | |

| Thr | Pro | Pro | Arg | Arg | Glu | Glu | Glu | Pro | Arg |
| 2405 | | | | | 2410 | | | | |

<210> SEQ ID NO 2
<211> LENGTH: 7242
<212> TYPE: DNA
<213> ORGANISM: Homo sapiens

<400> SEQUENCE: 2

```
atgggatct ccacagtcat ccttgaaatg tgtcttttat ggggacaagt tctatctaca    60
ggtgggtgga taccaaggac tacagactac gcttcactga ttccctcgga ggtgcccttg   120
gatccaactg tagcagaagg ttctccattt ccctcggagt cgaccctgga gtcaactgta   180
gcagaaggtt ctccgatttc cttggagtca accctggagt caactgtagc agaaggttct   240
ctgattccat cagagtcaac cctggagtca actgtagcag aaggatctga ttctggtttg   300
gccctgaggc tggtgaatgg agatggcagg tgtcagggcc gagtggagat cctataccga   360
ggctcctggg gcaccgtgtg tgatgacagc tgggacacca tgatgccaa cgtggtctgt   420
aggcagctgg gttgtggctg gccatgtca gctccaggaa atgcctggtt tggccagggc   480
tcaggaccca ttgccctgga tgatgtgcgc tgctcaggac acgaatccta cctgtggagc   540
tgcccccaca tggctggct ctcccataac tgtggccatg tgaagatgc tggtgttatc   600
tgctcagctg ccagcctca gtcaacactc aggccagaaa gttggcctgt caggatatca   660
ccacctgtac ccacagaagg atctgaatcc agtttggccc tgaggctggt gaatggaggc   720
gacaggtgtc gaggccgggt ggaggtccta taccgaggct cctggggcac cgtgtgtgat   780
gactactggg acaccaatga tgccaatgtg tgtcgcaggc agctgggctg ggctgggcc   840
atgtcagccc aggaaatgc ccagtttggc cagggctcag acccattgt cctggatgat   900
gtgcgctgct caggacacga gtcctacctg tggagctgcc ccacaatgg ctggctcacc   960
cacaactgtg ccatagtga agacgctggt gtcatctgct cagctcccca gtcccggccg  1020
acacccagcc cagatacttg gccgacctca catgcatcaa cagcaggacc tgaatccagt  1080
ttggccctga ggctggtgaa tggaggtgac aggtgtcagg gccgagtgga ggtcctatac  1140
cgaggctcct ggggcaccgt gtgtgatgat agctgggaca ccagtgacgc caatgtggtc  1200
tgccggcagc tgggctgtgg ctgggccacg tcagccccag gaaatgcccg gtttggccag  1260
ggttcaggac ccattgtcct ggatgacgtg cgctgctcag gctatgagtc ctacctgtgg  1320
agctgccccc acaatggctg gctctcccat aactgtcagc acagtgaaga cgctggtgtc  1380
atctgctcag ctgcccactc ctggtcgacg cccagtccag acacgttgcc gaccatcacc  1440
```

```
ttacctgcat cgacagtagg atctgaatcc agtttggccc tgaggctggt gaatggaggt    1500
gacaggtgtc agggccgagt ggaggtccta taccgaggct cctggggcac cgtgtgtgat    1560
gacagctggg acaccaatga tgccaatgtg gtctgcaggc agctgggctg tggctgggcc    1620
atgttggccc caggaaatgc ccggtttggt cagggctcag acccattgt cctggatgac     1680 gtgcgctgct cagggaatga gtcctacttg tggagctgcc cccacaatgg ctggctctcc    1740
cataactgtg gccatagtga agacgctggt gtcatctgct caggacctga atccagtttg    1800
gccctgaggc tggtgaatgg aggtgacagg tgtcagggcc gagtggaggt cctataccga    1860
ggctcttggg gcaccgtgtg tgatgacagc tgggacacca atgatgccaa tgtggtctgc    1920
aggcagctgg gctgtggctg gccatgtca gccccaggaa atgcccggtt tggtcagggc     1980
tcaggaccca ttgtcctgga tgatgtgcgc tgctcaggac atgagtccta cctgtggagc    2040
tgccccaaca atggctggct ctcccacaac tgtggccatc atgaagatgc tggtgtcatc    2100
tgctcagctg cccagtcccg gtcgacgccc aggccagaca cgttgtcgac catcacgtta    2160
cctccatcga cagtaggatc tgaatccagt ttgaccctga ggctggtgaa tggaagtgac    2220
aggtgtcagg gccgagtaga ggtcctatac cgaggctcct ggggcaccgt gtgtgatgac    2280
agctgggata ccaatgatgc caatgtagtc tgcaggcagc tgggctgtgg ctgggccacg    2340
tcggccccag gaaatgcccg gtttggccag ggctcaggac ccattgttct ggatgatgtg    2400
cgctgctcag acacgagtc ctacctgtgg agctgccccc acaatggctg gctctcccac     2460
aactgtggcc atcatgaaga tgctggtgtc atctgctcag tttcccagtc ccggccgaca    2520
cccagtccag atacttggcc gacctcacat gcatcaacag caggacctga atccagcttg    2580
gccctgaggc tggtgaatgg aggtgacagg tgtcagggcc gagtggaggt cctataccga    2640
ggctcctggg gcaccgtgtg tgatgatagc tgggacacca gtgacgccaa tgtggtctgc    2700
cggcagctgg gctgtggctg gccacgtca gccccaggaa atgcccggtt tggccagggt     2760
tcaggaccca ttgtcctgga tgacgtgcgc tgctcaggct atgagtccta cctgtggagc    2820
tgcccccaca atggctggct ctcccataac tgtcagcaca gtgaagacgc tggtgtcatc    2880
tgctcagctg cccactcctg gtcgacgccc agtccagaca cattgccgac catcaccttg    2940
cctgcatcga cagtaggatc tgaatccagt ttggccctga ggctggtgaa tggaggtgac    3000
aggtgtcagg gccgagtgga ggtcctatac caaggctcct ggggcaccgt gtgcgatgac    3060
agctgggaca ccaatgatgc caatgtcgtc tgcaggcaac tggctgtgg ctgggccatg     3120 tcagccccag gaaatgcccg gtttggtcag ggctcaggac ccattgtcct ggatgatgtg    3180
cgctgctcag acacgagtc ttacctgtgg agctgccccc acaatggctg gctctcccac     3240
aactgtggcc atagtgaaga cgctggtgtc atctgctcag cttcccagtc ccggccaaca    3300
cctagtccag acacttggcc aacctcacat gcatcaacag caggatctga atccagtttg    3360
gccctgaggc tggtgaatgg aggtgacagg tgtcagggcc gagtggaggt cctataccga    3420
ggctcctggg gcaccgtgtg tgatgactac tggacacca atgatgccaa tgtggttttgc     3480 aggcagctgg gctgtggctg gccatgtca gccccaggaa atgcccggtt tggccagggt     3540
tcaggaccca ttgtcctgga tgtgcgc tgctcaggac atgagtccta tctgtggagc        3600
tgcccccaca atggctggct ctcccacaac tgtggccatc atgaagacgc tggtgtcatc    3660
tgctcagctt cccagtccca gccgacaccc agcccagaca cttggccaac ctcacatgca    3720
tcaacagcag gatctgaatc cagtttggcc ctgaggctgg tgaatggagg tgacaggtgt    3780
cagggccgag tggaggtcct ataccgaggc tcctggggca ccgtgtgtga tgactactgg    3840
```

```
gacaccaatg atgccaatgt ggtttgcagg cagctgggct gtagctgggc cacgtcagcc    3900
ccaggaaatg cccggtttgg ccagggttca ggacccattg tcctggatga tgtgcgctgc    3960
tcaggacatg agtcctatct gtggagctgc ccccacaatg ctggttctc ccacaactgt     4020 ggccatcatg aagacgctgg tgtcatctgc tcagcttccc agtcccagcc gacacccagc    4080
ccagacactt ggccaacctc acatgcatca acagcaggat ctgaatccag tttggccctg    4140
aggctggtga atggaggtga caggtgtcag ggccgagtgg aggtcctata ccgaggctcc    4200 tgggcaccg tgtgtgatga ctactgggac accaatgatg ccaatgtggt ttgcaggcag     4260
ctgggctgtg gctgggccac gtcagcccca ggaaatgccc ggtttggcca gggttcagga    4320
cccattgtcc tggatgatgt gcgctgctca ggacatgagt cctatctgtg gagctgcccc    4380
cacaatggct ggctctccca caactgtggc catcatgaag acgctggtgt catctgctca    4440 gcttccagt cccagccgac acccagccca gacacttggc caacctctcg tgcatcaaca     4500
gcaggatctg aatccacttt ggccctgaga ctggtgaatg gaggtgacag gtgtcgaggc    4560
cgagtggagg tcctatacca aggctcctgg ggcaccgtgt gtgatgacta ctgggacacc    4620
aatgatgcca acgtggtctg caggcagctg gctgtggct gggccatgtc agccccagga     4680
aatgcccagt ttggccaggg ctcaggaccc attgtcctgg atgatgtgcg ctgctcagga    4740
cacgagtctt acctgtggag ctgcccccac aatggctggc tctcccacaa ctgtggccat    4800
catgaagatg ctggtgtcat ctgctcagct gctcagtccc agtcaacgcc caggccagat    4860
acttggctga ccaccaactt accggcattg acagtaggat ctgaatccag tttggctctg    4920
aggctggtga atggaggtga caggtgtcga ggccgagtgg aggtcctgta tcgaggctcc    4980
tggggaaccg tgtgtgatga cagctgggac accaatgatg ccaatgtggt ctgcaggcag    5040
ctgggctgtg gctgggccat gtcggcccca ggaaatgccc ggtttggcca gggctcagga    5100
cccattgtcc tggatgatgt gcgctgctca gggaatgagt cctacctgtg gagctgcccc    5160
cacaaaggct ggctcaccca caactgtggc catcacgaag acgctggtgt catctgctca    5220
gccacccaaa taaattctac tacgacagat tggtggcatc caacaactac aaccactgca    5280
agaccctctt caaattgtgg tggcttctta ttctatgcca gtgggacatt ctccagccca    5340
tcctaccctg catactaccc caacaatgct aagtgtgttt gggaaataga agtgaattct    5400
ggttatcgca taaacctggg cttcagtaat ctgaaattgg aggcacacca taactgcagt    5460
tttgattatg ttgaaatctt tgatggatca ttgaatagca gtctcctgct ggggaaaatc    5520
tgtaatgata ccaggcaaat atttacatct tcttacaacc gaatgaccat tcactttcga    5580
agtgacatca gtttccaaaa cactggcttt ttggcttggt ataactcctt cccaagcgat    5640
gccaccttga ggttggtcaa tttaaattca tcctatggtc tatgtgccgg gcgtgtagaa    5700
atttaccatg gtggcacctg ggggacagtt tgtgatgact cctggaccat tcaggaagct    5760
gaggtggtct gcagacagct agggtgtgga cgtgcagttt cagcccttgg aaatgcatat    5820
tttggctctg gctctggccc catcacccta gacgatgtag agtgctcagg gacggaatcc    5880
actctctggc agtgccggaa ccgaggctgg ttctcccaca actgtaatca tcgtgaagat    5940
gctggtgtca tctgctcagg aaaccatcta tcgacacctg ctcctttct caacatcacc    6000 cgtccaaaca cagattattc ctgcggaggc ttcctatccc aaccatcagg gactttcc      6060 agcccattct atcccgggaa ctatccaaac aatgccaagt gtgtgtggga cattgaggtg    6120
caaaacaact accgtgtgac tgtgatcttc agagatgtcc agcttgaagg tggctgcaac    6180
tatgattata ttgaagtttt cgatggcccc taccgcagtt cccctctcat tgctcgagtt    6240
```

```
tgtgatgggg ccagaggctc cttcacttct tcctccaact tcatgtccat tcgcttcatc    6300
agtgaccaca gcatcacaag gagagggttc cgggctgagt actactccag tccctccaat    6360
gacagcacca acctgctctg tctgccaaat cacatgcaag ccagtgtgag caggagctat    6420
ctccaatcct tgggcttttc tgccagtgac cttgtcattt ccacctggaa tggatactac    6480
gagtgtcggc cccagataac gccgaacctg tgatattca caattcccta ctcaggctgc    6540
ggcaccttca agcaggcaga caatgacacc atcgactatt ccaacttcct cacagcagct    6600
gtctcaggtg gcatcatcaa gaggaggaca gacctccgta ttcacgtcag ctgcagaatg    6660
cttcagaaca cctgggtcga caccatgtac attgctaatg acaccatcca cgttgctaat    6720
aacaccatcc aggtcgagga agtccagtat ggcaattttg acgtgaacat ttcctttttat   6780 acttcctcat ctttcttgta tcctgtgacc agccgcccct tactacgtgga cctgaaccag    6840 gacttgtacg ttcaggctga aatcctccat tctgatgctg tactgacctt gtttgtggac    6900
acctgcgtgg catcaccata ctccaatgac ttcacgtctt tgacttatga tctaatccgg    6960
agtggatgcg tgagggatga cacctacgga ccctactcct cgccgtctct tcgcattgcc    7020
cgcttccggt tcagggcctt ccacttcctg aaccgcttcc cctccgtgta cctgcgttgt    7080
aaaatggtgg tgtgcagagc gtatgacccc tcttcccgct gctaccgagg ctgtgtgttg    7140
aggtcgaaga gggatgtggg ctcctaccag gaaaaggtgg acgtcgtcct gggtcccatc    7200
cagctgcaga ccccccccacg ccgagaagag gagcctcggt ag                      7242

<210> SEQ ID NO 3
<211> LENGTH: 28
<212> TYPE: DNA
<213> ORGANISM: Dmbt1/KOcf1

<400> SEQUENCE: 3
gcactagtgg caaggtaaag gaggcaag                                         28

<210> SEQ ID NO 4
<211> LENGTH: 26
<212> TYPE: DNA
<213> ORGANISM: Dmbt1/KOcr1

<400> SEQUENCE: 4
tgtctagacc ttcaccgaac gactcc                                           26

<210> SEQ ID NO 5
<211> LENGTH: 20
<212> TYPE: DNA
<213> ORGANISM: Dmbt1/KOaf1

<400> SEQUENCE: 5
cccagtgtca gtgagcttag                                                  20

<210> SEQ ID NO 6
<211> LENGTH: 21
<212> TYPE: DNA
<213> ORGANISM: Dmbt1/KOar1

<400> SEQUENCE: 6
gctcaacaac tgctaccata c                                                21

<210> SEQ ID NO 7
<211> LENGTH: 23
<212> TYPE: DNA
<213> ORGANISM: Dmbt1/KObf1
```

```
<400> SEQUENCE: 7
cttttgtggg gtcaaattct gtc                                              23

<210> SEQ ID NO 8
<211> LENGTH: 19
<212> TYPE: DNA
<213> ORGANISM: Dmbt1/KObr1

<400> SEQUENCE: 8
ctgttggtcc cttgacctg                                                   19
```